United States Patent
Lieb et al.

(10) Patent No.: US 6,458,965 B1
(45) Date of Patent: Oct. 1, 2002

(54) ARYL PHENYL SUBSTITUTED CYCLIC KETOENOLS

(75) Inventors: Folker Lieb, Leverkusen; Reiner Fischer, Monheim; Alan Graff, Köln; Udo Schneider, Leverkusen; Thomas Bretshneider, Lohmar; Christoph Erdelen, Leichlingen; Wolfram Andersch, Bergisch Gladbach; Mark Wilhelm Drewes, Langenfeld, all of (DE); Markus Dollinger, Overland Park, KS (US); Ingo Wetcholowsky, Vinhedo (BR); Randy Allen Myers, Overland Park, KS (US)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/646,722

(22) PCT Filed: Mar. 18, 1999

(86) PCT No.: PCT/EP99/01787

§ 371 (c)(1),
(2), (4) Date: Jan. 2, 2001

(87) PCT Pub. No.: WO99/48869

PCT Pub. Date: Sep. 30, 1999

(30) Foreign Application Priority Data

Mar. 26, 1998 (DE) .......................... 198 13 354

(51) Int. Cl.$^7$ .................. C07D 209/54; C07D 209/96; A01N 43/36

(52) U.S. Cl. ................. 548/408; 548/544; 548/577; 504/287

(58) Field of Search ............... 548/408, 544, 548/577; 504/283

(56) References Cited

U.S. PATENT DOCUMENTS

| | | | |
|---|---|---|---|
| 4,104,043 A | 8/1978 | Durden, Jr. et al. | 71/107 |
| 4,175,135 A | 11/1979 | Haines | 424/311 |
| 4,209,432 A | 6/1980 | Roth | 260/29.2 M |
| 4,209,532 A | 6/1980 | Wheeler | 424/331 |
| 4,256,657 A | 3/1981 | Wheeler | 260/465 D |
| 4,256,658 A | 3/1981 | Wheeler | 260/465 D |
| 4,256,659 A | 3/1981 | Wheeler | 260/465 D |
| 4,257,858 A | 3/1981 | Wheeler | 204/158 R |
| 4,283,348 A | 8/1981 | Wheeler | 260/465 D |
| 4,303,669 A | 12/1981 | D'Silva | 424/282 |
| 4,338,122 A | 7/1982 | Wheeler | 71/122 |
| 4,351,666 A | 9/1982 | Koerwer | 71/106 |
| 4,409,153 A | 10/1983 | Hodakowski | 260/946 |
| 4,422,870 A | 12/1983 | Wheeler | 71/106 |
| 4,436,666 A | 3/1984 | Wheeler | 260/455 B |
| 4,526,723 A | 7/1985 | Wheeler et al. | 260/410.5 |
| 4,551,547 A | 11/1985 | Wheeler | 560/255 |
| 4,613,617 A | 9/1986 | Sousa et al. | |
| 4,632,698 A | 12/1986 | Wheeler | 71/106 |
| 4,659,372 A | 4/1987 | Wheeler | 71/106 |
| 4,925,868 A | 5/1990 | Terao et al. | 514/425 |
| 4,985,063 A | 1/1991 | Fischer et al. | 71/88 |
| 5,045,560 A | 9/1991 | Fischer et al. | 514/425 |
| 5,091,537 A | 2/1992 | Fischer et al. | 546/226 |
| 5,094,681 A | 3/1992 | Krämer et al. | 71/88 |
| 5,116,836 A | 5/1992 | Fischer et al. | 514/224.2 |
| 5,142,065 A | 8/1992 | Fischer et al. | 548/533 |
| 5,186,737 A | 2/1993 | Fischer et al. | 504/283 |
| 5,207,817 A | 5/1993 | Krämer et al. | 504/299 |
| 5,258,527 A | 11/1993 | Krauskopf et al. | 548/543 |
| 5,262,383 A | 11/1993 | Fischer et al. | 504/195 |
| 5,332,720 A | 7/1994 | Krüger et al. | 504/281 |
| 5,358,924 A | 10/1994 | Krüger et al. | 504/197 |
| 5,393,729 A | 2/1995 | Fischer et al. | 504/128 |
| 5,462,913 A | 10/1995 | Fischer et al. | 504/138 |
| 5,494,890 A | 2/1996 | Cederbaum et al. | 504/281 |
| 5,504,057 A | 4/1996 | Fischer et al. | 504/283 |
| 5,506,193 A | 4/1996 | Cederbaum et al. | 504/282 |
| 5,565,450 A | 10/1996 | Fischer et al. | 514/227.2 |
| 5,567,671 A | 10/1996 | Fischer et al. | 504/283 |
| 5,602,078 A | 2/1997 | Fischer et al. | 504/283 |
| 5,610,122 A | 3/1997 | Fischer et al. | 504/251 |
| 5,622,917 A | 4/1997 | Fischer et al. | 504/283 |
| 5,661,110 A | 8/1997 | Krüger et al. | 504/281 |
| 5,677,449 A | 10/1997 | Fischer et al. | 544/165 |
| 5,719,310 A | 2/1998 | Fischer et al. | 560/83 |
| 5,719,316 A | 2/1998 | Erdellen et al. | |
| 5,739,389 A | 4/1998 | Krüger et al. | 562/489 |
| 5,780,394 A | 7/1998 | Krüger et al. | 504/281 |
| 5,808,135 A | 9/1998 | Fischer et al. | 560/129 |
| 5,817,700 A | 10/1998 | Dube et al. | 514/768 |
| 5,830,826 A | 11/1998 | Fischer et al. | 504/195 |
| 5,840,661 A | 11/1998 | Fischer et al. | 504/348 |
| 5,945,444 A | 8/1999 | Fischer et al. | 514/445 |
| 5,977,029 A | 11/1999 | Fischer et al. | 504/292 |
| 5,994,274 A | 11/1999 | Fischer et al. | 504/282 |
| 6,057,352 A | 5/2000 | Brown et al. | 514/384 |
| 6,096,895 A | 8/2000 | Brown et al. | 548/110 |
| 6,110,872 A | 8/2000 | Lieb et al. | 504/284 |
| 6,114,374 A | 9/2000 | Lieb et al. | 514/424 |
| 6,150,304 A | 11/2000 | Fischer et al. | 504/309 |

FOREIGN PATENT DOCUMENTS

| | | |
|---|---|---|
| CA | 2220440 | 11/1996 |
| DE | 4431730 | 8/1995 |
| DE | 195 43 864 | 8/1996 |
| DE | 196 49 665 | 10/1997 |
| DE | 19649665 | 10/1997 |
| EP | 521334 | 4/1991 |
| EP | 442077 | 8/1991 |
| GB | 2266888 | 11/1993 |
| WO | 96/02539 | 2/1996 |
| WO | 9620196 | 7/1996 |
| WO | 96/20196 | 7/1996 |
| WO | 96/21652 | 7/1996 |
| WO | 9625395 | 8/1996 |
| WO | 96/25395 | 8/1996 |
| WO | 96/36229 | 11/1996 |
| WO | 96/36615 | 11/1996 |
| WO | 9714667 | 4/1997 |
| WO | 97/14667 | 4/1997 |
| WO | 9736868 | 10/1997 |

OTHER PUBLICATIONS

International Search Report for PCT EP99/01787 dated Aug. 23, 2001.
*Chem. Pharm Bull., 15 (8), (month unavailable), 1967, pp. 1120–122, Seikichi Suzuki, et al, "Studies on Antiviral Agents. $N^{*1}$ Biological Activity of Tenuazonic Acid Derivatives".

Liebigs Ann. Chem. (month unavailable), 1985, pp. 1095–1098, Roland Schmierer et al, "Cyclisierung von N–Acylalanin–und N–Acylglycinestern".

J. Chem. Soc. Perkin Trans. 1, (month unavailable), 1985, pp. 1567–1576, A. C. Campbell et al, "Synthesis of (E)–and (Z)–Pulvinones".

J. Heterocycl. Chem., 25 (5), Sep.–Oct., 1988, pp. 1301–1305, G. Zvilichovsky, "Crystal Structure, Dilociation and Zwitterion Formation in 2,6–Diaryl–1(3)–oxo–3(1)–hydroxy–5(7)–imino–7(5)–amino–1$H$, 5$H$–(3$H$, 7$H$)–pyrazolo[1,2–a]pyrazoles".

J. Heterocyclic Chem, 25, (5), Sep.–Oct., 1988, pp. 1307–1310, G. Zvilichovsky et al, "Acidity and Alkylation of 4–Phenyl–3,5–dihydroxy–pyrazole and Its Derivatives. C versus O and N Alkylation".

Zh. Obshch. Khem., 34 (7), (month unavailable), 1964, pp. 239–240, Z. I. Miroshnichenko et al, "Cyanine Dyes, Derivatives of 2–Methyl 4,5–(2',3'–Thionaphtheno)Thiazole".

Farmakol Toksikol (Moscow), 38 (2), (month unavailable), 1976, pp. 180–186, K. M. Lakin et al, "The Effect of Some Pyrazolone Derivatives on the Aggregation of Thrombocytes" (Abstract on p. 186).

Arch. Pharm, 309, (month unavailable) 1976, pp. 558–564, A. M. Chirazi et al, "Zur Synthese von Kawalactonderivaten".

Chem. Bec., 91 (month unavailable) 1958, p. 249, K.–H. Boltze et al, "Ringschlüsse mit Malonsäure–dichloriden".

Monatsh, 95 (month unavailable) 1964, pp. 147–155, E. Ziegler et al, "Synthesen von Heterocyclen, 52. Mitt.: Über Derivate des 2–Phenyl–4–hydroxy–[1,3–thiazinons–(6)][1]".

Heterocycl. Chem., Apr. 10, 1973, pp. 223–224, Roger Ketcham et al, "Synthesis of Heterocycles. 174 (1,2) Substituted Thiazines and Bisthiazinyls from Dithiooxamide and Trichlorophenyl Malonates".

Tetrahedron, vol. 48, No. 36 (month unavailable) 1992, pp. 7519–7526, J. Micklefield et al, "Alkylation and Acylation of 5–Phenylsulphonyl–and 5–Cyanobutyrolactones".

J. Chem. Soc. (C), (month unavailable), 1967, pp. 405–409, R. L. Edwards et al, "Constituents of the Higher Fungi. Part IV. Involutin, a Diphenylcyclopenteneone from *Pazillus involutus*(Oeder ex Fries)".

J. Economic Entomology, vol. 66, No. 2(month unavailable), 1973, pp. 584–586, A. A. Sousa et al, "Esters of 3–Hydroxy–2–Arylindones, a New Class of Acaricide[1]".

J. Org. Chem., vol. 44, No. 26 (month unavailable), 1979, pp. 4906–4912, T. N. Wheeler, "Novel Photochemical Synthesis of 2–Aryl–1,3–cyclohexanediones".

*Primary Examiner*—Mukund Shah
*Assistant Examiner*—Sudhaker B. Patel
(74) *Attorney, Agent, or Firm*—Joseph C. Gil; Raymond J. Harmuth

(57) ABSTRACT

The present invention relates to novel arylphenyl-substituted cyclic ketonols of the formula (I)

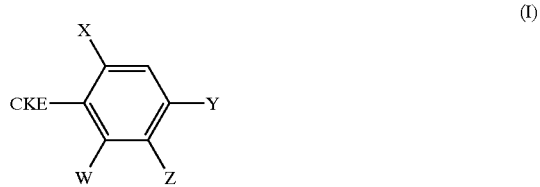

in which

X represents halogen, alkyl, alkoxy, alkenyloxy, alkylthio, alkylsulphinyl, alkylsulphonyl, halogenoalkyl, halogenoalkoxy, halogenoalkenyloxy, nitro, cyano or in each case optionally substituted phenyl, phenoxy, phenylthio, phenylalkoxy or phenylalkylthio, Y represents in each case optionally substituted cycloalkyl, aryl or hetaryl, W and Y independently of one another each represent hydrogen, halogen, alkyl, alkoxy, alkenyloxy, halogenoalkyl, halogenoalkoxy, halogenoalkenyloxy, nitro or cyano, CKE represents one of the groups

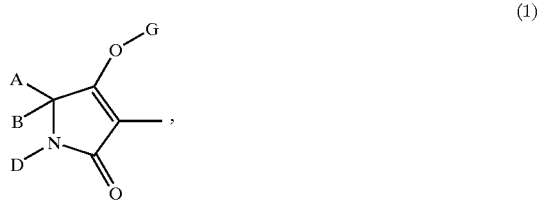

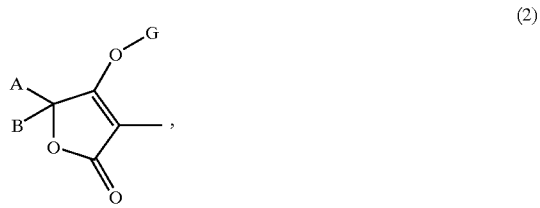

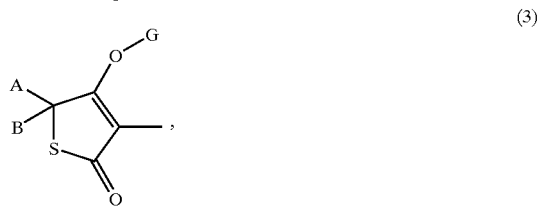

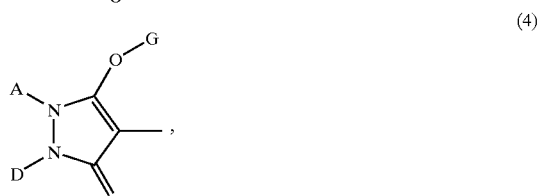

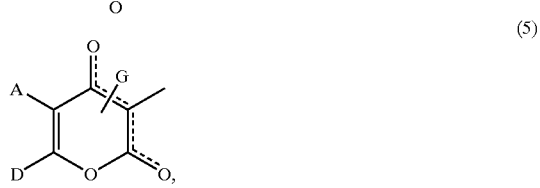

-continued
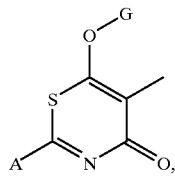
(6)
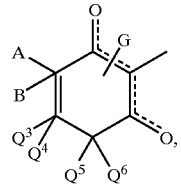
(8)
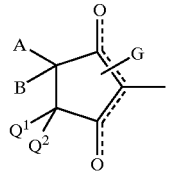
(7)
or
in which
A, B, D, G and $Q^1$ to $Q^6$ are each as defined in the description,
to a plurality of processes for their preparation and to their use as pesticides and herbicides.
12 Claims, No Drawings

ARYL PHENYL SUBSTITUTED CYCLIC KETOENOLS

The present invention relates to novel arylphenyl-substituted cyclic ketoenols, to a plurality of processes for their preparation and to their use as pesticides and herbicides.

Pharmaceutical properties of 3-acyl-pyrrolidine-2,4-diones have already been described (S. Suzuki et al. Chem. Pharm. Bull. 15 1120 (1967)). Furthermore, N-phenylpyrrolidine-2,4-dionies have been synthesized by R. Schmierer and H. Mildenberger (Liebigs Ann. Chem. 1985, 1095). A biological activity of these compounds has not been described.

EP-A-0 262 399 and GB-A-2 266 888 disclose compounds of a similar structure (3-aryl-pyrrolidine-2,4-diones) of which, however, no herbicidal, insecticidal or acaricidal activity his become known. Unsubstituted bicyclic 3-aryl-pyrrolidine-2,4-dione derivatives (EP-A-355 599 and EP-415 211) and substituted monocyclic 3-aryl-pyrrolidine-2,4-dione derivatives (EP-A-377 893 and EP-442 077) having herbicidal, insecticidal or acaricidal activity are known.

Also known are polycyclic 3-arylpyrrolidine-2,4-dione derivatives (EP-442 073) and 1H-arylpyrrolidine-dione derivatives (EP-456 063, EP-521 334, EP-596 298, EP-613 884, EP-613 885, WO 94/01 997, WO 95/26 954, WO 95/20 572, EP-A-0 668 267, WO 96/25 395, WO 96/35 664, WO 97/01 535, WO 97/02 243 and WO 97/36 868, DE-19 716 591).

It is known, that certain substituted $\Delta^3$-dihydrofuran-2-one derivatives have herbicidal properties (cf. DE-A-4 014 420). The synthesis of the tetronic acid derivatives used as starting materials (such as, for example, 3-(2-methylphenyl)-4-hydroxy-5-(4-fluorophenyl)-$\Delta^3$-dihydrofuran-2-one) is likewise described in DE-A-4 014 420. Compounds of a similar structure are known from the publication Campbell et al., J. Chem. Soc., Perkin Trans. 1, 1985, (8) 1567–76, without any insecticidal and/or acaricidal activity being mentioned. Furthermore, 3-aryl-$\Delta^3$-dihydrofuranone derivatives having herbicidal, acaricidal and insecticidal properties are known from EP-A-528 156, EP-A-0 647 637, WO 95/26 345, WO 96/20 196, WO 96/25 395, WO 96/35 664, WO 97/01 535, WO 97/02 243 and WO 97/36 868, DE-19 716 591. 3-Aryl-$\Delta^3$-dihydrothiophen-one derivatives are likewise known (WO 95/26 345, 96/25 395, WO 97/01 535, WO 97/02 243, WO 97/36 868, DE 19 716 591).

Also known from the literature are certain 3H-pyrazol-3-one derivatives, such as, for example, 1,2-diethyl-1,2-dihydro-5-hydroxy-4-phenyl-3H-pyrazol-3-one or [5-oxo-1,2-diphenyl-4-(p-sulphophenyl)-3-pyrazolin-3-yl]-oxy disodium salt, or p-(3-hydroxy-5-oxo-1,2-diphenyl-3-pyrazolin-4-yl)-benzenesulphonic acid (cf. J. Heterocycl. Chem., 25(5), 1301–1305, 1988 or J. Heterocycl. Chem., 25(5), 1307–1310, 1988 or Zh. Obshch. Khim., 34(7), 2397–2402, 1964). However, a biological activity of these compounds is not described.

Furthermore, it is known that the trisodium salt of 4,4',4"-(5-hydroxy-3-oxo-1H-pyrazol-1,2,4(3H)-triyl)-tris-benzenesulphonic acid has pharmacological properties (cf. Farmakol. Toksikol. (Moscow), 38(2), 180–186, 1976). However, it is not known to be used in crop protection.

Moreover, EP-508 126 and WO 92/16 510, WO 96/21 652 describe 4-arylpyrazolidin-3,5-dione derivatives having herbicidal, acaricidal and insecticidal properties. Additionally, 4-arylpyrazolidines have become known, of which fungicidal properties have been described (WO 96/36 229, WO 96/36 615, WO 96136 616, WO 96/36 633).

Certain phenyl-pyrone derivatives which are unsubstituted in the phenyl ring have already become known (cf. A. M. Chirazi, T. Kappe and E. Ziegler, Arch. Pharm. 309, 558 (1976) and K.-H. Boltze and K. Heidenbluth, Chem. Ber. 91, 2849), a possible use of these compounds as pesticides not being mentioned. Phenyl-pyrone derivatives which are substituted in the phenyl ring and have herbicidal, acaricidal and insecticidal properties are described in EP-A-588 137, WO 96/25 395, WO 96/35 664, WO 97/01 535, WO 97/02 243, WO 97/16 436, WO 97/19 941 and WO 97/36 868, DE-19 716 591.

Certain 5-phenyl-1,3-thiazine derivatives which are unsubstituted in the phenyl ring have already become known (cf. E. Ziegler and E. Steiner, Monatsh. 95, 147 (1964), R. Ketcham, T. Kappe and E. Ziegler, J. Heterocycl. Chem. 10, 223 (1973)), a possible use of these compounds as pesticides not being mentioned. 5-Phenyl-1,3-thiazine derivatives which are substituted in the phenyl ring and have herbicidal, acaricidal and insecticidal activity are described in WO 94/14 785, WO 96/02 539, WO 96/35 664, WO 97/01 535, WO 97/02 243, WO 97/02 243, WO 97/36 868.

It is known that certain substituted 2-arylcyclopentanediones have herbicidal and acaricidal properties (cf., for example, U.S. Pat. Nos. 4,283,348; 4,338,122; 4,436,666; 4,526,723; 4,551,547; 4,632,698; WO 96/01 798; WO 96/03 366 and also WO 97/14 667). Moreover, compounds of a similar structure are known: 3-hydroxy-5,5-dimethyl-2-phenylcyclopent-2-ene-1-one from the publication Micklefield et al., Tetrahedron, (1992), 7519–26 and the natural product involutine (–)-cis-5-(3,4-dihydroxyphenyl)-3,4-dihydroxy-2-(4-hydroxyphenyl)-cyclopent-2-ene-one from the publication Edwards et al., J. Chem. Soc. S, (1967), 405–9. An insecticidal or acaricidal activity is not described. Moreover, 2-(2,4,6-trimethylphenyl)-1,3-indanedione is known from the publication J. Economic Entomology, 66, (1973), 584 and German Offenlegungsschrift DE-2 361 084, with herbicidal and acaricidal activities being mentioned.

It is known that certain substituted 2-arylcyclohexanediones have herbicidal and acaricidal properties (U.S. Pat. Nos. 4,175,135, 4,209,432, 4,256,657, 4,256,658, 4,256,659, 4,257,858, 4,283,348, 4,303,669, 4,351,666, 4,409,153, 4,436,666, 4,526,723, 4,613,617, 4,659,372, DE-2 813 341, and also Wheeler, T. N., J. Org. Chem. 44, 4906 (1979)).

However, the activity and the activity spectrum of these compounds are, in particular at low application rates and concentrations, not always entirely satisfactory. Furthermore, the compatibility of these compounds with plants is not always satisfactory.

This invention, accordingly, provides novel compounds of the formula (I)

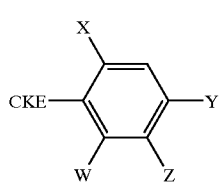

(I)

in which
X represents halogen, alkyl, alkoxy, alkenyloxy, alkylthio, alkylsulphinyl, alkylsulphonyl, halogenoalkyl, halogenoalkoxy, halogenoalkenyloxy, nitro, cyano or in each case optionally substituted phenyl, phenoxy, phenylthio, phenylalkoxy or phenylalkylthio, Z represents in each case optionally substituted cycloalkyl, aryl or hetaryl, W and Y independently of one another each represent hydrogen, halogen, alkyl, alkoxy, alkenyloxy, halogenoalkyl, halogenoalkoxy, halogenoalkenyloxy, nitro or cyano, CKE represents one of the groups

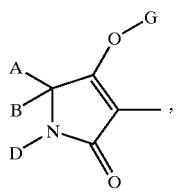
(1)

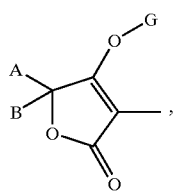
(2)

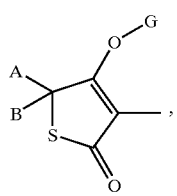
(3)

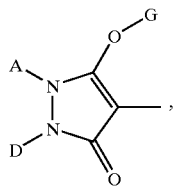
(4)

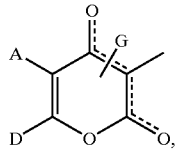
(5)

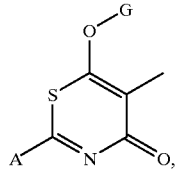
(6)

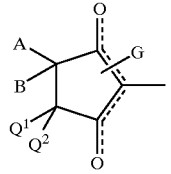 or
(7)

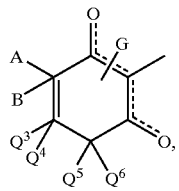
(8)

in which

A represents hydrogen, in each case optionally halogen-substituted alkyl, alkenyl, alkoxyalkyl, polyalkoxyalkyl, alkylthioalkyl, saturated or unsaturated, optionally substituted cycloalkyl in which optionally at least one ring atom is replaced by a heteroatom, or in each case optionally halogen-, alkyl-, halogenoalkyl-, alkoxy, halogenoalkoxy-, cyano- or nitro-substituted aryl, arylalkyl or hetaryl, B represents hydrogen, alkyl or alkoxyalkyl, or A and B together with the carbon atom to which they are attached represent a saturated or unsaturated unsubstituted or substituted cycle which optionally contains at least one heteroatom, D represents hydrogen or an optionally substituted radical selected from the series consisting of alkyl, alkenyl, alkinyl, alkoxyalkyl, polyalkoxyalkyl, alkylthioalkyl, saturated or unsaturated cycloalkyl in which one or more ring members are optionally replaced by heteroatoms, arylalkyl, aryl, hetarylalkyl or hetaryl or A and D together with the atoms to which they are attached represent a saturated or unsaturated ring which is unsubstituted or substituted in the A,D moiety and which optionally contains at least one (in the case where CKE=(4)) further heteroatom, or A and $Q^1$ together represent alkanediyl or alkenediyl, each of which is optionally substituted by in each case optionally substituted alkyl, hydroxyl, alkoxy, alkylthio, cycloalkyl, benzyloxy or aryl, or $Q^1$ represents hydrogen or alkyl, $Q^2$, $Q^4$, $Q^5$ and $Q^6$ independently of one another each represent hydrogen or alkyl, $Q^3$ represents hydrogen, alkyl, alkoxyalkyl, alkylthioalkyl, optionally substituted cycloalkyl (in which optionally one methylene group is replaced by oxygen or sulphur) or optionally substituted phenyl, or $Q^3$ and $Q^4$ together with the carbon atom to which they are attached represent a saturated or unsaturated unsubstituted or substituted ring which optionally contains a heteroatom, G represents hydrogen (a) or represents one of the groups

(b)

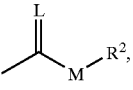
(c)

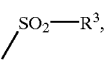
(d)

-continued

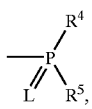

E or

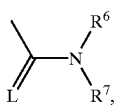

in which

E represents a metal ion or an ammonium ion,
L represents oxygen or sulphur,
M represents oxygen or sulphur,
$R^1$ represents tin each case optionally halogen-substituted alkyl, alkenlyl, alkoxyalkyl, alkylthioalkyl, polyalkoxyalkyl or optionally halogen-, alkyl- or alkoxy-substituted cycloalkyl which may be interrupted by at least one heteroatom, in each case optionally substituted phenyl, phenylalkyl, hetaryl, phenoxyalkyl or hetaryloxyalkyl,
$R^2$ represents in each case optionally halogen-substituted alkyl, alkenyl, alkoxyalkyl, polyalkoxyalkyl or represents in each case optionally substituted cycloalkyl, phenyl or benzyl,
$R^3$, $R^4$ and $R^5$ independently of one another each represent in each case optionally halogen-substituted alkyl, alkoxy, alkylamino, dialkylamino, alkylthio, alkenylthio, cycloalkylthio or represent in each case optionally substituted phenyl, benzyl, phenoxy or phenylthio, and
$R^6$ and $R^7$ independently of one another each represent hydrogen, in each case optionally halogen-substituted alkyl, cycloalkyl, alkenyl, alkoxy, alkoxyalkyl, represent optionally substituted phenyl, represent optionally substituted benzyl, or together with the nitrogen atom to which they are attached represent a cycle which is optionally interrupted by oxygen or sulphur.

Depending, inter alia, on the nature of the substituents, the compounds of the formula (I) can be present as geometrical and/or optical isomers or mixtures of isomers in varying compositions, which can be separated, if desired, in a customary manner. The present invention provides both the pure isomers and the isomer mixtures, their preparation and use and also compositions comprising them. In the following, for simplicity, however, compounds of the formula (I) are always referred to, although both pure compounds and, if appropriate, mixtures having different proportions of isomeric compounds are intended.

Including the meanings (1) to (8) of the group CKE, the following principal structures (I-1) to (I-8) result:

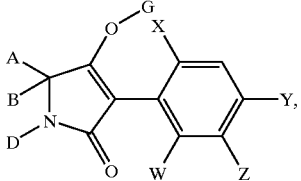
(I-1)

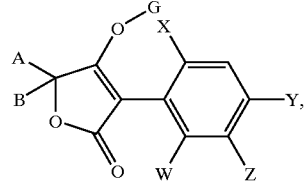
(I-2)

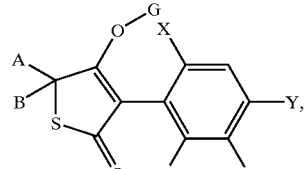
(I-3)

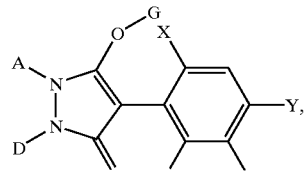
(I-4)

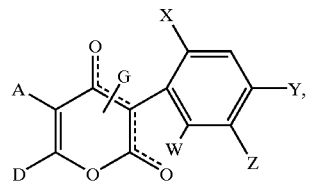
(I-5)

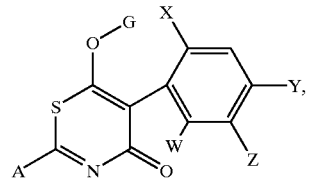
(I-6)

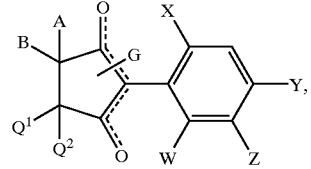
(I-7)

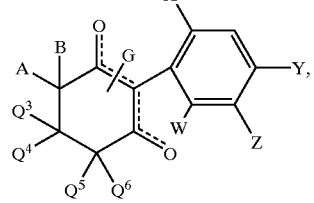
(I-8)

in which

A, B, D, G, $Q^1$, $Q^2$, $Q^3$, $Q^4$, $Q^5$, $Q^6$, W, X, Y and Z are each as defined above.

Including the various meanings (a), (b), (c), (d), (e), (f) and (g) of the group G, the following principal structures (I-1-a) to (I-1-g) result if CKE represents the group (1), (I-1-a):
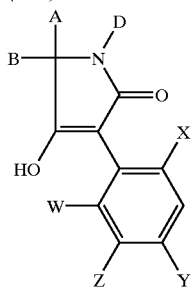
(I-1-b):
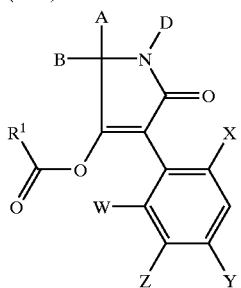
(I-1-c):
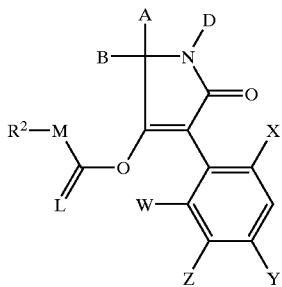
(I-1-d):
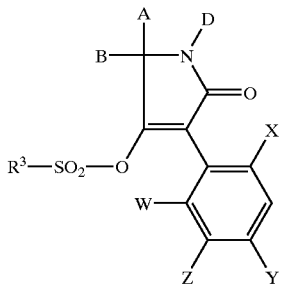
(I-1-e):
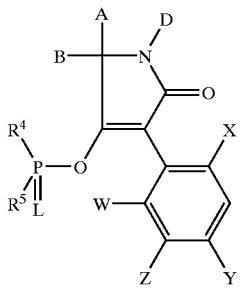
-continued
(I-1-f):
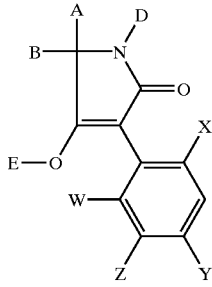
(I-1-g):
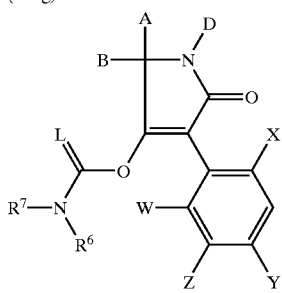
in which
A, B, D, E, L, M, W, X, Y, Z, $R^1$, $R^2$, $R^3$, $R^4$, $R^5$, $R^6$ and $R^7$ are each as defined above.
Including the various meanings (a), (b), (c), (d), (e), (f) and (g) of the group G, the following principal structures (I-2-a) to (I-2-g) result if CKE represents the group (2),
(I-2-a):
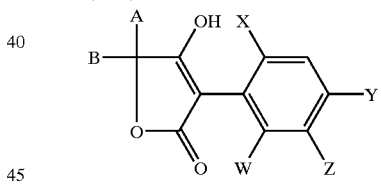
(I-2-b):
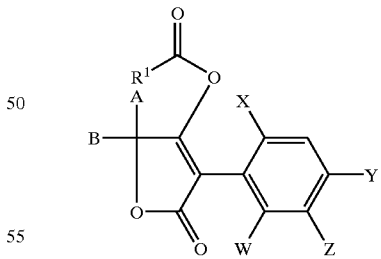
(I-2-c):
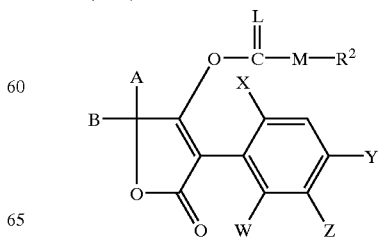

-continued (I-2-d):
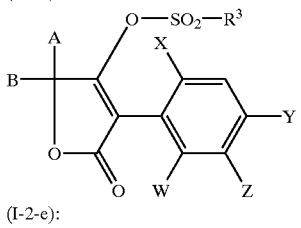

(I-2-e):
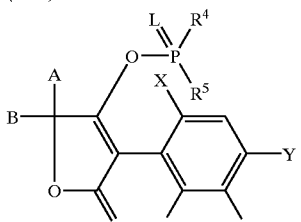

(I-2-f):
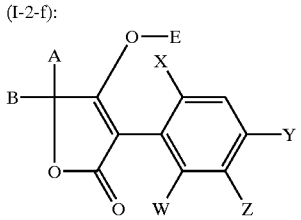

(I-2-g):
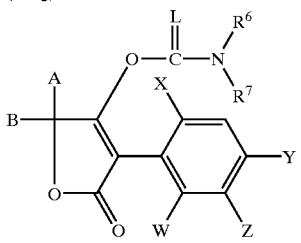

in which

A, B, E, L, M, W, X, Y, Z, $R^1$, $R^2$, $R^3$, $R^4$, $R^5$, $R^6$ and $R^7$ are each as defined above.

Including the various meanings (a), (b), (c), (d), (e), (f) and (g) of the group G, the following principal structures (I-3-a) to (I-3-g) result if CKE represents the group (3), (I-3-a):
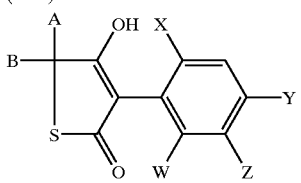

(I-3-b):
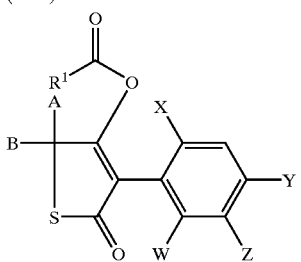

-continued (I-3-c):
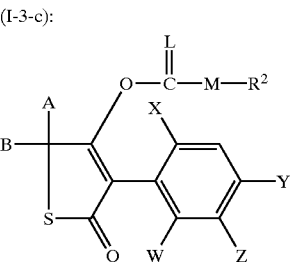

(I-3-d):
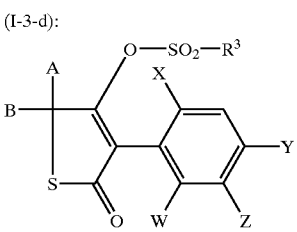

(I-3-e):
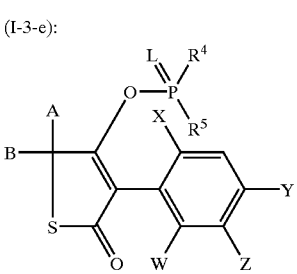

(I-3-f):
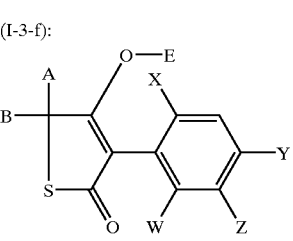

(I-3-g):
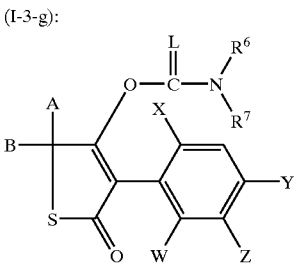

in which

A, B, E, L, M, W, X, Y, Z, $R^1$, $R^2$, $R^3$, $R^4$, $R^5$, $R^6$ and $R^7$ are each as defined above.

Including the various meanings (a), (b), (c), (d), (e), (f) and (g) of the group G, the following principal structures (I-4-a) to (I-4-g) result if CKE represents the group (4), (I-4-a):
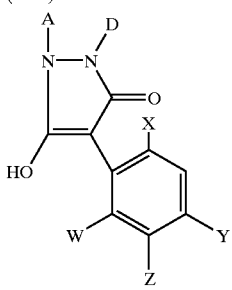

(I-4-b):
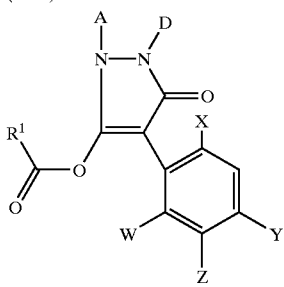

(I-4-c):
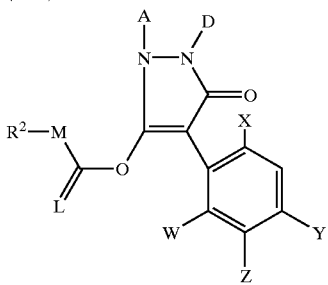

(I-4-d):
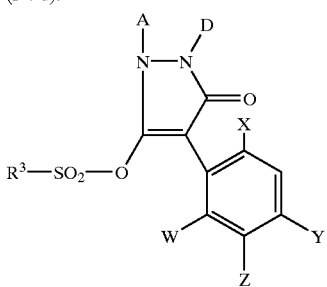

(I-4-e):
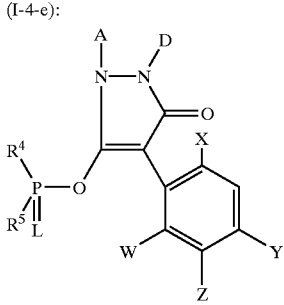

-continued (I-4-f):
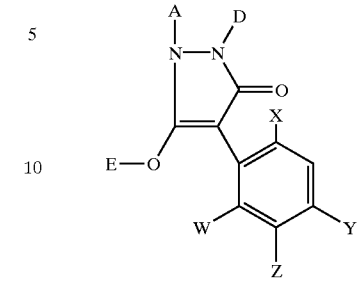

(I-4-g):
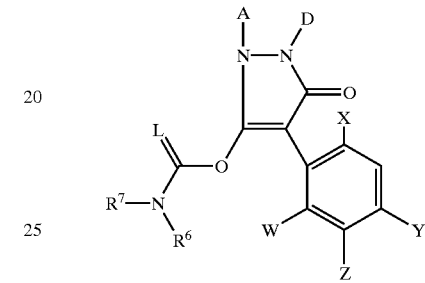

in which

A, D, E, L, M, W, X, Y, Z, $R^1$, $R^2$, $R^3$, $R^4$, $R^5$, $R^6$ and $R^7$ are each as defined above.

Depending on the position of the substituent G, the compounds of the formula (I-5) can be present in the two isomeric forms of the formulae (I-5-A) and (I-5-B), (I-5-A)
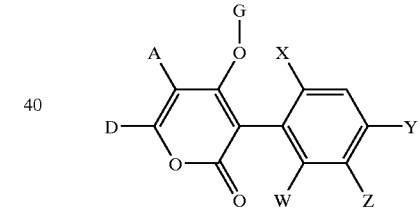

(I-5-B)
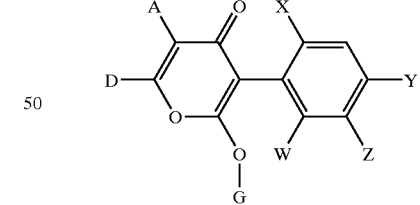

which is meant to be indicated by the dashed line in the formula (I-5).

The compounds of the formulae (I-5-A) and (I-5-B) can be present both as mixtures and in the form of their pure isomers. Mixtures of the compounds of the formulae (I-5-A) and (I-5-B) can be separated, if desired, in a manner known per se, by physical methods, for example by chromatographic methods.

For reasons of clarity, hereinbelow in each case only one of the possible isomers is given. This does not exclude that the compounds may, if appropriate, be present in the form of the isomer mixtures or in the respective other isomeric form.

Including the various meanings (a), (b), (c), (d), (e), (f) and (g) of the group G, the following principal structures (I-5-a) to (I-5-g) result if CKE represents the group (5), (I-5-a):
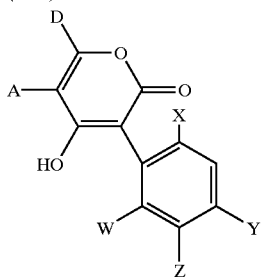

(I-5-b):
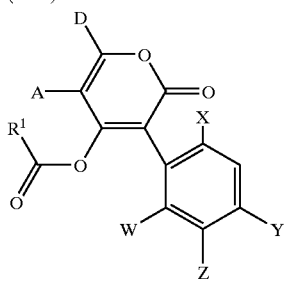

(I-5-c):
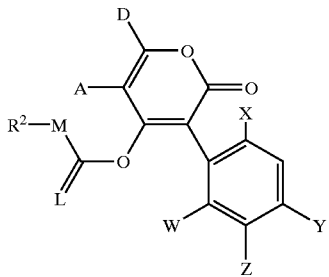

(I-5-d):
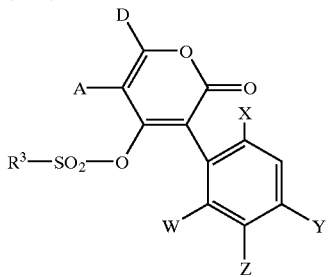

(I-5-e):
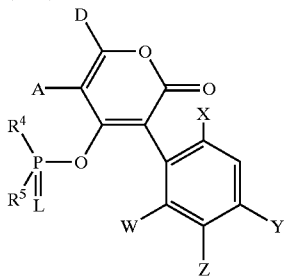

(I-5-f):
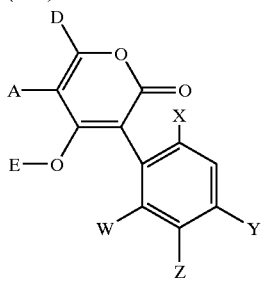

(I-5-g):
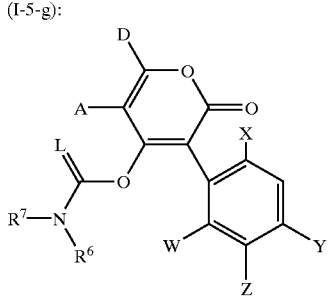

in which

A, D, E, L, M, W, X, Y, Z, $R^1$, $R^2$, $R^3$, $R^4$, $R^5$, $R^6$ and $R^7$ are each as defined above.

Including the various meanings (a), (b), (c), (d), (e), (f) and (g) of the group G, the following principal structures (I-6-a) to (I-6-g) result if CKE represents the group (6), (I-6-a):
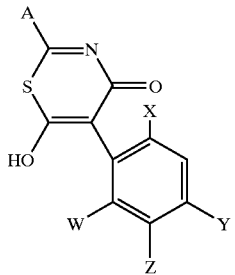

(I-6-b):
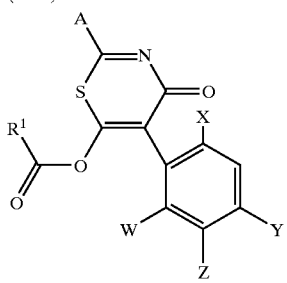

(I-6-c):
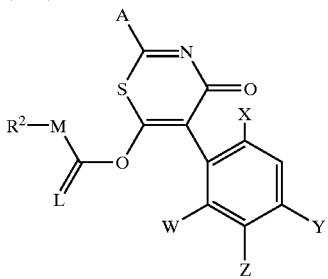

(I-6-d):
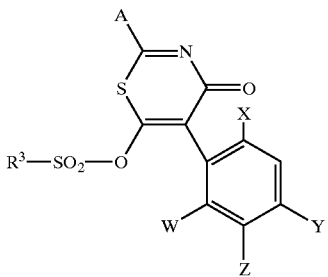

(I-6-e):
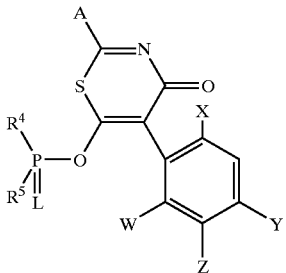

(I-6-f):
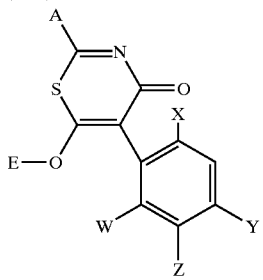

(I-6-g):
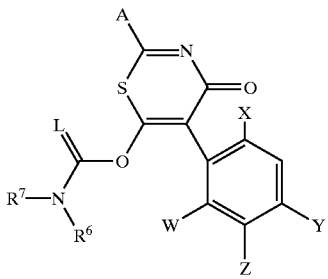

in which

A, E, L, M, W, X, Y, Z, $R^1$, $R^2$, $R^3$, $R^4$, $R^5$, $R^6$ and $R^7$ are each as defined above.

Depending on the position of the substituent G, the compounds of the formula (I-7) can be present in the two isomeric forms of the formulae (I-7-A) and (I-7-B), (I-7-A):
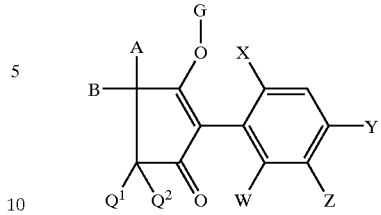

(I-7-B):
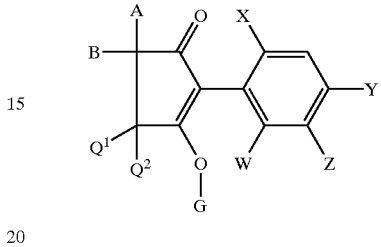

which is meant to be indicated by the dashed line in the formula (I).

The compounds of the formulae (I-7-A) and (I-7-B) can be present both as mixtures and in the form of their pure isomers. Mixtures of the compounds of the formulae (I-7-A) and (I-7-B) can be separated, if desired, by physical methods, for example by chromatographic methods.

For reasons of clarity, hereinbelow in each case only one of the possible isomers is given. This does not exclude that the compounds may, if appropriate, be present in the form of the isomer mixtures or in the respective other isomeric form.

Including the various meanings (a), (b), (c), (d), (e), (f) and (g) of the group G, the following principal structures (I-7-a) to (I-7-g) result:

(I-7-a):
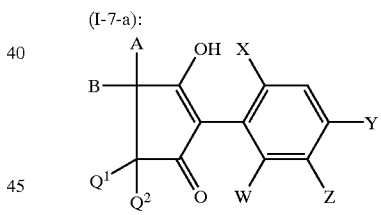

(I-7-b):
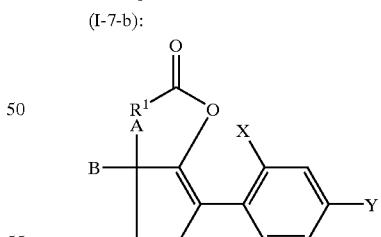

(I-7-c):
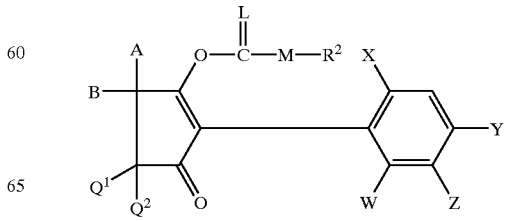

-continued (I-7-d):
(I-7-e):
(I-7-f):
(I-7-g):

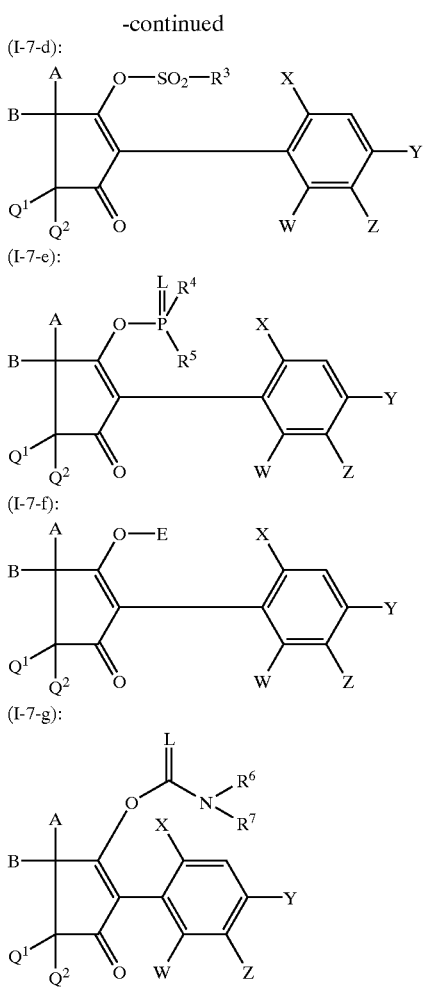

in which

A, B, Q$^1$, Q$^2$, E, L, M, W, X, Y, Z, R$^1$, R$^2$, R$^3$, R$^4$, R$^5$, R$^6$ and R$^7$ are each as defined above.

Depending on the position of the substituent G, the compounds of the formula (I-8) can be present in the two isomeric forms of the formulae (I-8-A) and (I-8-B)

(I-8-A)

(I-8-B)

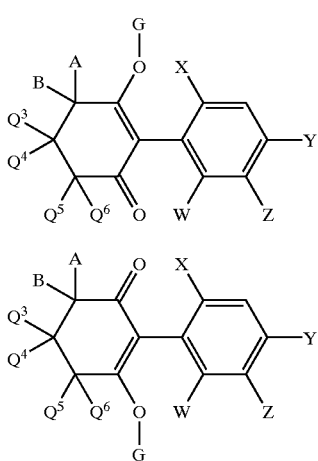

which is meant to be indicated by the dashed line in the formula (I-8).

The compounds of the formulae (I-8-A) and (I-8-B) can be present both as mixtures and in the form of their pure isomers. Mixtures of the compounds of the formulae (I-8-A) and (I-8-B) can be separated, if desired, by physical methods, for example by chromatographic methods.

For reasons of clarity, hereinbelow in each case only one of the possible isomers is given. This takes into account that the relevant compound may, if appropriate, be present as an isomer mixture or in the respective other isomeric form.

Including the various meanings (a), (b), (c), (d), (e), (f) and (g) of the group G, the following principal structures (I-8-a) to (I-8-g) result:

(I-8-a):
(I-8-b):
(I-8-c):
(I-8-d):

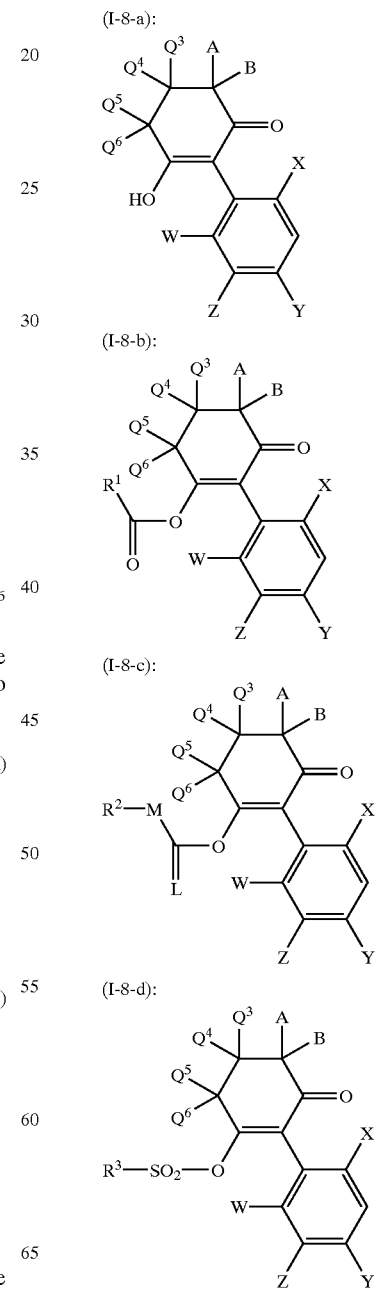

-continued (I-8-e):

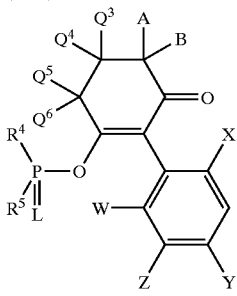

(I-8-f):

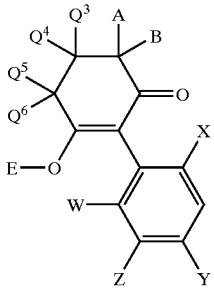

(I-8-g):

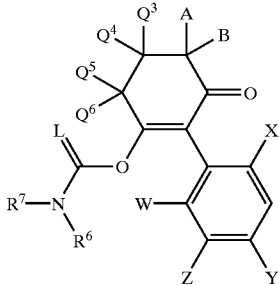

in which

A, B, E, L, M, $Q^3$, $Q^4$, $Q^5$, $Q^6$, W, X, Y, Z, $R^1$, $R^2$, $R^3$, $R^4$, $R^5$, $R^6$ and $R^7$ are each as defined above.

Furthermore, it has been found that the novel compounds of the formula (I) are obtained by one of the processes described below:

(A) Substituted 3-phenylpyrrolidine-2,4-diones or their enols of the formula (I-1-a)

(I-1-a)

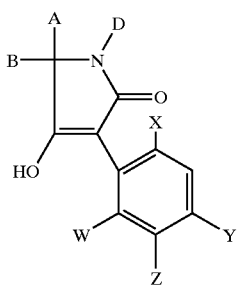

in which

A, B, D, W, X, Y and Z are each as defined above are obtained when

N-acylamino acid esters of the formula (II)

(II)

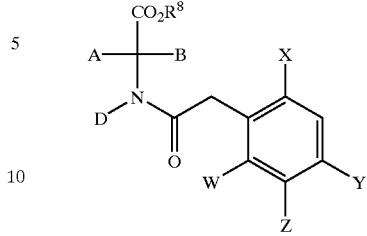

in which

A, B, D, W, X, Y and Z are each as defined above and $R^8$ represents alkyl (preferably $C_1$–$C_6$-alkyl)

are condensed intramolecularly in the presence of a diluent and in the presence of a base.

(B) Moreover, it has been found that substituted 3-phenyl-4-hydroxy-$\Delta^3$-dihydrofuranone derivatives of the formula (I-2-a)

(I-2-a)

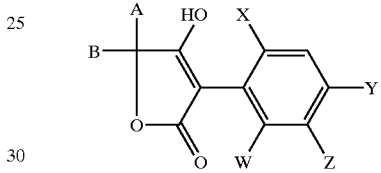

in which

A, B, W, X, Y and Z are each as defined above are obtained when carboxylic esters of the formula (III)

(III)

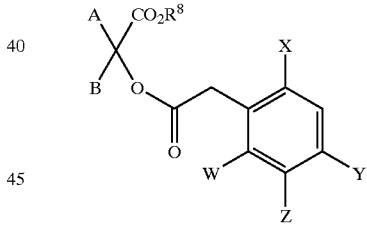

in which

A, B, W, X, Y, Z and $R^8$ are each as defined above are condensed intramolecularly in the presence of a diluent and in the presence of a base.

(C) Furthermore, it has been found that substituted 3-phenyl-4-hydroxy-$\Delta^3$-dihydrothiophenone derivatives of the formula (I-3-a)

(I-3-a)

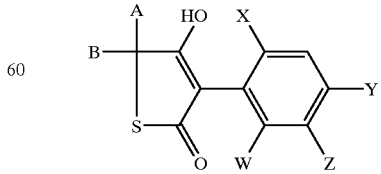

in which

A, B, W, X, Y and Z are each as defined above are obtained when

β-ketocarboxylic esters of the formula (IV)

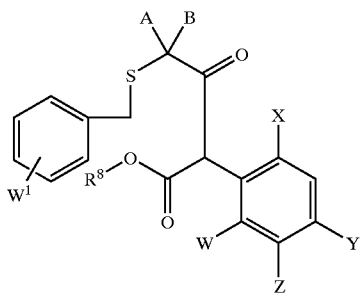

in which

A, B, W, X, Y, Z and $R^8$ are each as defined above and $W^1$ represents hydrogen, halogen, alkyl (preferably $C_1$–$C_6$-alkyl) or alkoxy (preferably $C_1$–$C_8$-alkoxy)

are cyclized intramolecularly, if appropriate in the presence of a diluent and in the presence of an acid.

(D) Furthermore, substituted 3-hydroxyl-4-phenyl-5-oxo-pyrazolines of the formula (I-4-a)

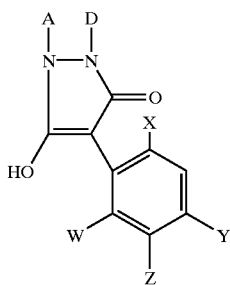

in which

A, D, W, X, Y and Z are each as defined above are obtained when (α) halogenocarbonyl ketenes of the formula (V)

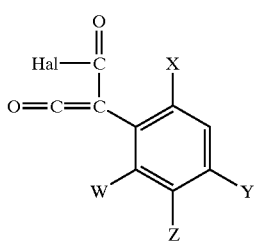

in which

W, X, Y and Z are each as defined above and

Hal represents halogen (in particular chlorine or bromine)

or (β) malonic acid derivatives of the formula (VI)

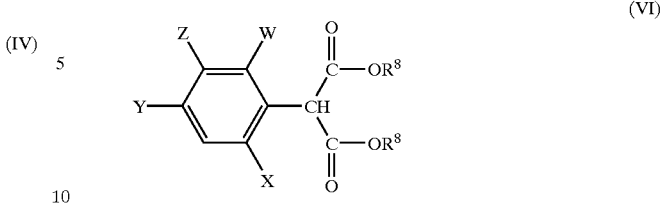

in which $R^8$, W, X, Y and Z are each as defined above are reacted with hydrazines of the formula (VII)

A—NH—NH—D    (VII)

in which

A and D are each as defined above if appropriate in the presence of a diluent and if appropriate in the presence of a base.

(E) Furthermore, it has been found that the novel substituted 3-phenylpyrone derivatives of the formula (I-5-a)

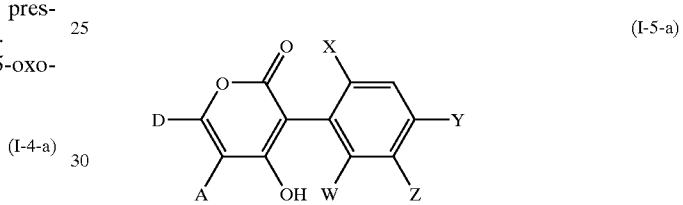

in which

A, D, W, X, Y and Z are each as defined above are obtained when carbonyl compounds of the formula (VIII)

in which

A and D are each as defined above or their silyl enol ethers of the formula (VIIIa)

in which

A, D and $R^8$ are each as defined above are reacted with ketene acid halides of the formula (V)

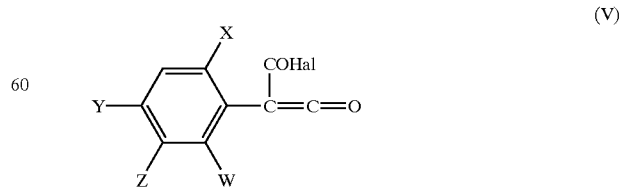

in which

W, X, Y and Z are each as defined above and

Hal represents halogen (preferably represents chlorine or bromine), if appropriate in the presence of a diluent and if appropriate in the presence of an acid acceptor.

Furthermore, it has been found (F) that the novel substituted phenyl-1,3-thiazine derivatives of the formula (I-6-a)

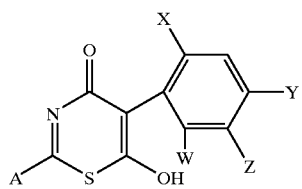
(I-6-a)

in which

A, W, X, Y and Z are each as defined above are obtained when thioamides of the formula (IX)

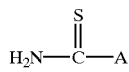
(IX)

in which

A is as defined above are reacted with ketene acid halides of the formula (V)

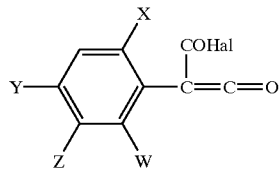
(V)

in which

Hal, W, X, Y and Z are each as defined above, if appropriate in the presence of a diluent and if appropriate in the presence of an acid acceptor.

Furthermore, it has been found (G) at compounds of the formula (I-7-a)

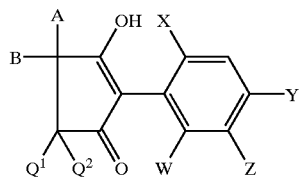
(I-7-a)

in which

A, B, $Q^1$, $Q^2$, W, X, Y and Z are each as defined above, are obtained when ketocarboxylic esters of the formula (X)

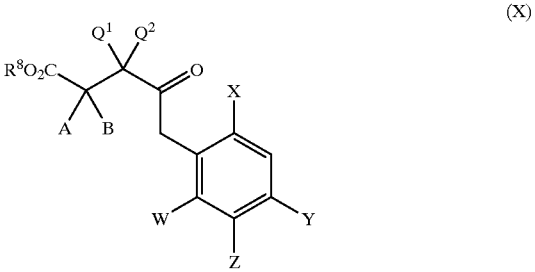
(X)

in which

A, B, $Q^1$, $Q^2$, W, X, Y and Z are each as defined above and $R^8$ represents alkyl (in particular $C_1$–$C_8$-alkyl)

are cyclized intramolecularly, if appropriate in the presence of a diluent and in the presence of a base.

Moreover, it has been found (H) that compounds of the formula (I-8-a)

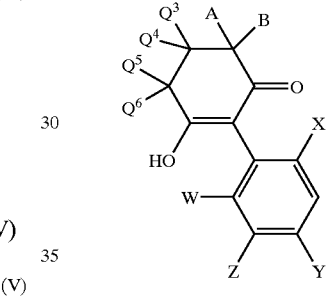
(I-8-a)

in which

A, B, $Q^3$, $Q^4$, $Q^5$, $Q^6$, W, X, Y and Z are each as defined above are obtained when 6-aryl-5-keto-hexanoic esters of the formula (XI)

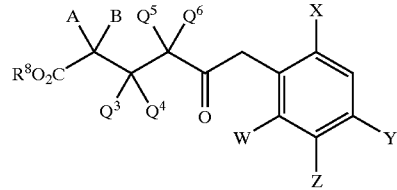
(XI)

in which

A, B, $Q^3$, $Q^4$, $Q^5$, $Q^6$, W, X, Y and Z are each as defined above and $R^8$ represents alkyl (preferably $C_1$–$C_6$-alkyl)

are condensed intramolecularly in the presence of a diluent and in the presence of a base; or (I) that compounds of the formulae (I-1-a) to (I-8-a) shown above in which A, B, D, $Q^1$, $Q^2$, $Q^3$, $Q^4$, $Q^5$, $Q^6$, W, X, Y and Z are each as defined above are obtained when compounds of the formula (I-1'-a) to (I-8'-a),

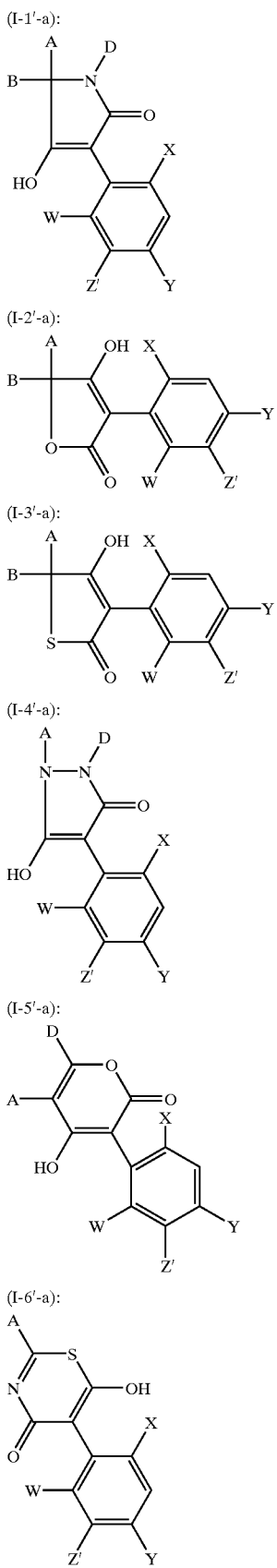

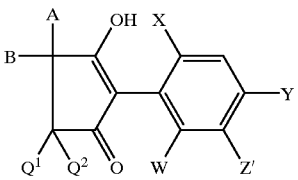

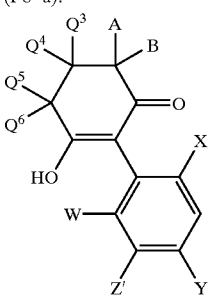

in which
A, B, D, Q, $Q^2$, $Q^3$, $Q^4$, $Q^5$, $Q^6$, W, X and Y are each as defined above and
Z' represents chlorine, bromine or iodine, preferably represents bromine,
are reacted with boronic acids of the formula (XII)

in which
Z is as defined above
in the presence of a solvent, a base and a catalyst, suitable catalysts being, in particular, palladium complexes.

Moreover, it has been found
Moreover, it has been found (J) that the compounds of the formulae (I-1-b) to (I-8-b) shown above in which A, B, D, $Q^1$, $Q^2$, $Q^3$, $Q^4$, $Q^5$, $Q^6$, $R^1$, W, X, Y and Z are each as defined above are obtained when compounds of the formulae (I-1-a) to (I-8-a) shown above in which A, B, D, $Q^1$, $Q^2$, $Q^3$, $Q^4$, $Q^5$, $Q^6$, W, X, Y and Z are each as defined above are in each case (α) reacted with acyl halides of the formula (XIII)

in which
$R^1$ is as defined above and
Hal represents halogen (in particular chlorine or bromine)
or (β) reacted with carboxylic anhydrides of the formula (XIV)

in which
$R^1$ is as defined above,
if appropriate in the presence of a diluent and if appropriate in the presence of an acid binder;

(K) that the compounds of the formulae (I-1-c) to (I-8-c) shown above in which A, B, D, $Q^1$, $Q^2$, $Q^3$, $Q^4$, $Q^5$, $Q^6$, $R^2$, M, W, X, Y and Z are each as defined above and L represents oxygen are obtained when compounds of the formulae (I-1-a) to (I-8-a) shown above in which A, B, D, $Q^1$, $Q^2$, $Q^3$, $Q^4$, $Q^5$, $Q^6$, W X, Y and Z are each as defined above are in each case reacted with chloroformic esters or chloroformic thioesters of the formula (XV)

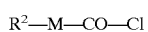

$$R^2—M—CO—Cl \quad (XV)$$

in which $R^2$ and M are each as defined above, if appropriate in the presence of a diluent and if appropriate in the presence of an acid binder;

(L) that compounds of the formulae (I-1-c) to (I-8-c) shown above in which A, B, D, $Q^1$, $Q^2$, $Q^3$, $Q^4$, $Q^5$, $Q^6$, $R^2$, M, W, X, Y and Z are each as defined above and L represents sulphur are obtained when compounds of the formulae (I-1-a) to (I-8-a) shown above in which A, B, D, $Q^1$, $Q^2$, $Q^3$, $Q^4$, $Q^5$, $Q^6$, W, X, Y and Z are each as defined above are in each case reacted with chloromonothioformic esters or chlorodithioformic esters of the formula (XVI)

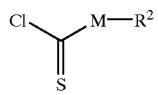
(XVI)

in which

M and $R^2$ are each as defined above if appropriate in the presence of a diluent and if appropriate in the presence of an acid binder and (M) that compounds of the formulae (I-1-d) to (I-8-d) shown above in which A, B, D, $Q^1$, $Q^2$, $Q^3$, $Q^4$, $Q^5$, $Q^6$, $R^3$, W, X, Y and Z are each as defined above are obtained when compounds of the formulae (I-1-a) to (I-8-a) shown above in which A, B, D, $Q^1$, $Q^2$, $Q^3$, $Q^4$, $Q^5$, $Q^6$, W, X, Y and Z are each as defined above are in each case reacted with sulphonyl chlorides of the formula (XVII)

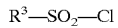

$$R^3—SO_2—Cl \quad (XVII)$$

in which $R^3$ is as defined above, if appropriate in the presence of a diluent and if appropriate in the presence of an acid binder, (N) that compounds of the formulae (I-1-c) to (I-8-e) shown above in which A, B, D, L, $Q^1$, $Q^2$, $Q^3$, $Q^4$, $Q^5$, $Q^6$, $R^4$, $R^5$, W, X, Y and Z are each as defined above are obtained when compounds of the formulae (I-1-a) to (I-8-a) shown above in which A, B, D, $Q^1$, $Q^2$, $Q^3$, $Q^4$, $Q^5$, $Q^6$, W, X, Y and Z are each as defined above are in each case reacted with phosphorus compounds of the formula (XVIII)

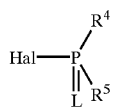
(XVIII)

in which

L, $R^4$ and $R^5$ are each as defined above and

Hal represents halogen (in particular chlorine or bromine), if appropriate in the presence of a diluent and if appropriate in the presence of an acid binder, (O) that compounds of the formulae (I-1-f) to (I-8-f) shown above in which A, B, D, E, $Q^1$, $Q^2$, $Q^3$, $Q^4$, $Q^5$, $Q^6$, W, X, Y and Z are each as defined above are obtained when compounds of the formulae (I-1-a) to (I-8-a) in which A, B, D, $Q^1$, $Q^2$, $Q^3$, $Q^4$, $Q^5$, $Q^6$, V, X, Y and Z are each as defined above in each case reacted with metal compounds or amines of the formulae (XIX) or (XX)

$$Me(OR^{10})_t \quad (XIX)$$

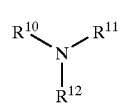
(XX)

in which

Me represents a mono- or divalent metal (preferably an alkali metal or alkaline earth metal, such as lithium, sodium, potassium, magnesium or calcium), t represents the number 1 or 2 and $R^{10}$, $R^{11}$, $R^{12}$ independently of one another each represent hydrogen or alkyl (preferably $C_1$–$C_8$-alkyl), if appropriate in the presence of a diluent, (P) that compounds of the formulae (I-1-g) to (I-8-g) shown above in which A, B, D, L, $Q^1$, $Q^2$, $Q^3$, $Q^4$, $Q^5$, $Q^6$, $R^6$, $R^7$, W, X, Y and Z are each as defined above are obtained when compounds of the formulae (I-1-a) to (I-8-a) shown above in which A, B, D, $Q^1$, $Q^2$, $Q^3$, $Q^4$, $Q^5$, $Q^6$, W, X, Y and Z are each as defined above are in each case (α) reacted with isocyanates or isothiocyanates of the formula (XXI)

$$R^6—N=C=L \quad (XXI)$$

in which $R^6$ and L are each as defined above if appropriate in the presence of a diluent and if appropriate in the presence of a catalyst, or (β) reacted with carbamoyl chlorides or thiocarbamoyl chlorides of the formula (XXII)

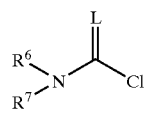
(XXII)

in which

L, $R^6$ and $R^7$ are each as defined above if appropriate in the presence of a diluent and if appropriate in the presence of an acid binder.

Furthermore, it has been found that the novel compounds of the formula (I) have very good activity as preferably as insecticides, acaricides and also as herbicides.

The formula (I) provides a general definition of the compounds according to the invention. Preferred substituents or ranges of the radicals listed in the formulae mentioned hereinabove and hereinbelow are illustrated below:

X preferably represents halogen, $C_1$–$C_6$-alkyl, $C_1$–$C_6$-halogenoalkyl, $C_1$–$C_6$-alkoxy, $C_3$–$C_6$-alkenyloxy, $C_1$–$C_6$-alkylthio, $C_1$–$C_6$-alkylsulphinyl, $C_1$–$C_6$-alkylsulphonyl, $C_1$–$C_6$-halogenoalkoxy, $C_3$–$C_6$-halogenoalkenyloxy, nitro, cyano or in each case optionally halogen-, $C_1$–$C_6$-alkyl-, $C_1$–$C_6$-alkoxy-, $C_1$–$C_4$-hatogenoalkyl-, $C_1$–$C_4$-halogenoalkoxy-, nitro- or cyano-substituted phenyl, phenoxy, phenylthio, benzyloxy or benzylthio.

Z preferably represents one of the radicals

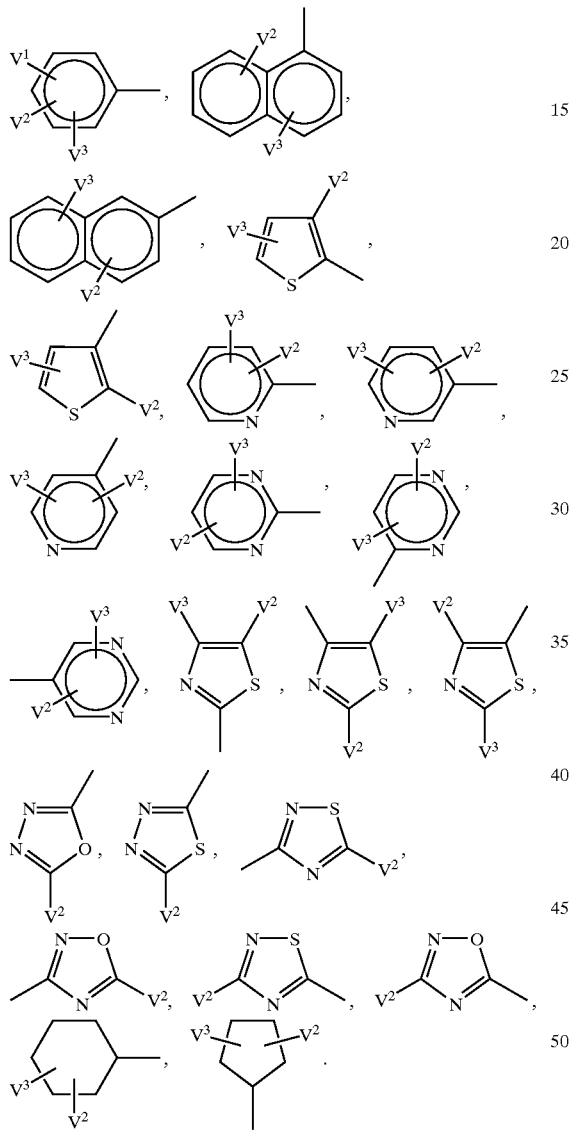

$V^1$ preferably represents hydrogen, halogen, $C_1$–$C_{12}$-alkyl, $C_1$–$C_6$-alkoxy, $C_1$–$C_6$-alkylthio, $C_1$–$C_6$-alkylsulphinyl, $C_1$–$C_6$-alkylsulphonyl, $C_1$–$C_4$-halogenoalkyl, $C_1$–$C_4$-halogenoalkoxy, nitro, cyano or phenyl, phenoxy, phenoxy-$C_1$–$C_4$-alkyl, phenyl-$C_1$–$C_4$-alkoxy, phenylthio-$C_1$–$C_4$-alkyl or phenyl-$C_1$–$C_4$-alkylthio, each of which is optionally mono- or polysubstituted by halogen, $C_1$–$C_6$-alkyl, $C_1$–$C_6$-alkoxy, $C_1$–$C_4$-halogenoalkyl, $C_1$–$C_4$-halogenoalkoxy, nitro or cyano.

$V^2$ and $V^3$ independently of one another each preferably represent hydrogen, halogen, $C_1$–$C_6$-alkyl, $C_1$–$C_6$-alkoxy, $C_1$–$C_4$-halogenoalkyl or $C_1$–$C_4$-halogenoalkoxy.

W and Y independently of one another each preferably represent hydrogen, halogen, $C_1$–$C_6$-alkyl, $C_1$–$C_6$-halogenoalkyl, $C_1$–$C_6$-alkoxy, $C_1$–$C_6$-halogenoalkoxy, nitro or cyano.

CKE preferably represents one of the groups

(1)

(2)

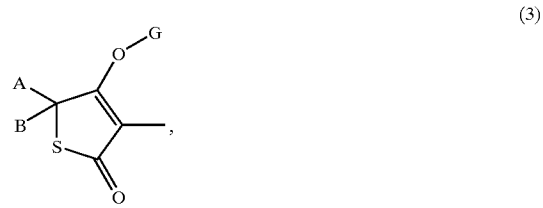
(3)

(4)

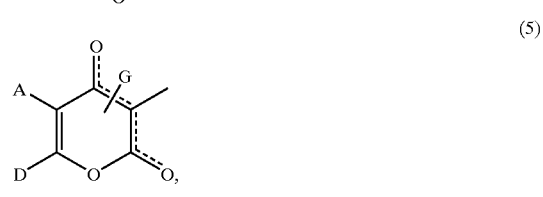
(5)

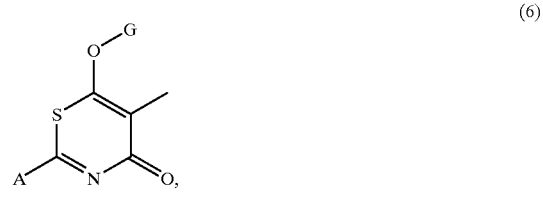
(6)

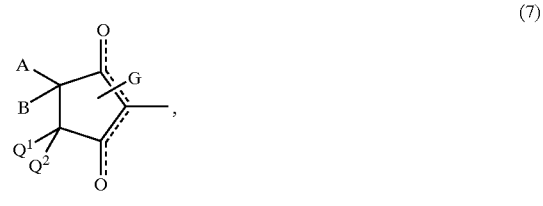
(7)

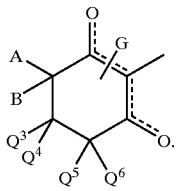

(8)

A preferably represents hydrogen or in each case optionally halogen-substituted $C_1$–$C_{12}$-alkyl, $C_3$–$C_8$-alkenyl, $C_1$–$C_{10}$-alkoxy-$C_1$–$C_8$-alkyl, poly-$C_1$–$C_8$-alkoxy-$C_1$–$C_8$-alkyl, $C_1$–$C_{10}$-alkylthio-$C_1$–$C_6$-alkyl, optionally halogen-, $C_1$–$C_6$-alkyl, $C_1$–$C_6$-alkoxy-substituted $C_3$–$C_8$-cycloalkyl in which optionally one or two not directly adjacent ring members are replaced by oxygen and/or sulphur or represents in each case optionally halogen-, $C_1$–$C_6$-alkyl-, $C_1$–$C_6$-halogenoalkyl-, $C_1$–$C_6$-alkoxy-, $C_1$–$C_6$-halogenoalkoxy-, cyano- or nitro-substituted $C_6$- or $C_{10}$-aryl (phenyl or naphthyl), hetaryl having 5 or 6 ring atoms (for example furanyl, pyridyl, imidazolyl, triazolyl, pyrazolyl, pyrimidyl, thiazolyl or thienyl) or $C_6$- or $C_{10}$-aryl-$C_1$–$C_6$-alkyl (phenyl- $C_1$–$C_6$-alkyl or naphthyl-$C_1$–$C_6$-alkyl).

B preferably represents hydrogen, $C_1$–$C_{12}$-alkyl or $C_1$–$C_8$-alkoxy-$C_1$–$C_6$-alkyl or A, B and the carbon atom to which they are attached preferably represent saturated $C_3$–$C_{10}$-cycloalkyl or unsaturated $C_5$–$C_{10}$-cycloalkyl in which optionally one ring member is replaced by oxygen or sulphur and which are optionally mono- or disubstituted by $C_1$–$C_8$-alkyl, $C_3$–$C_{10}$-cycloalkyl, $C_1$–$C_8$-halogenoalkyl, $C_1$–$C_8$-alkoxy, $C_1$–$C_8$-alkylthio, halogen or phenyl or A, B and the carbon atom to which they are attached preferably represent $C_3$–$C_6$-cycloalkyl which is substituted by an alkylenediyl group which optionally contains one or two not directly adjacent oxygen and/or sulphur atoms, or by an alkylenedioxyl group or by an alkylenedithioyl group which, together with the carbon atom to which it is attached, forms a further five- to eight-membered ring, or A, B and the carbon atom to which they are attached preferably represent $C_3$–$C_8$-cycloalkyl or $C_5$–$C_8$-cycloalkenyl, in which two substituents together with the carbon atoms to which they are attached represent in each case optionally $C_1$–$C_6$-alkyl-, $C_1$–$C_6$-alkoxy- or halogen-substituted $C_2$–$C_6$-alkanediyl, $C_2$–$C_6$-alkenediyl or $C_4$–$C_6$-alkanedienediyl in which optionally one methylene group is replaced by oxygen or sulphur.

D preferably represents hydrogen, in each case optionally halogen-substituted $C_1$–$C_{12}$-alkyl, $C_3$–$C_8$-alkenyl, $C_3$–$C_8$-alkinyl, $C_1$–$C_{10}$-alkoxy-$C_2$–$C_9$-alkyl, poly-$C_1$–$C_8$-alkoxy-$C_2$–$C_8$-alkyl, $C_1$–$C_{10}$-alkylthio-$C_2$–$C_8$-alkyl, optionally halogen-, $C_1$–$C_4$-alkyl-, $C_1$–$C_4$-alkoxy- or $C_1$–$C_4$-halogenoalkyl-substituted $C_3$–$C_8$-cycloalkyl in which optionally one ring member is replaced by oxygen or sulphur or in each case optionally halogen-, $C_1$–$C_6$-alkyl-, $C_1$–$C_6$-halogenoalkyl-, $C_1$–$C_6$-alkoxy-, $C_1$–$C_6$-halogenoalkoxy-, cyano- or nitro-substituted phenyl, hetaryl having 5 or 6 ring atoms (for example furanyl, imidazolyl, pyridyl, thiazolyl, pyrazolyl, pyrimidyl, pyrrolyl, thienyl or triazolyl), phenyl-$C_1$–$C_6$-alkyl or hetaryl-$C_1$–$C_6$-alkyl having 5 or 6 ring atoms (for example furanyl-, imidazolyl-, pyridyl-, thiazolyl-, pyrazolyl-, pyrimidyl-, pyrrolyl-, thienyl- or triazolyl- $C_1$–$C_6$-alkyl), or A and D together preferably represent in each case optionally substituted $C_3$–$C_6$-alkanediyl or $C_3$–$C_6$-alkenediyl in which optionally one methylene group is replaced by oxygen or sulphur, possible substituents in each case being:

halogen, hydroxyl, mercapto or in each case optionally halogen-substituted $C_1$–$C_{10}$-alkyl, $C_1$–$C_6$-alkoxy, $C_1$–$C_6$-alkylthio, $C_3$–$C_7$-cycloalkyl, phenyl or benzyloxy, or a further $C_3$–$C_6$-alkanediyl group, $C_3$–$C_6$-alkenediyl group or a butadienyl group which is optionally substituted by $C_1$–$C_6$-alkyl or in which optionally two adjacent substituents together with the carbon atoms to which they are attached form a further saturated or unsaturated ring having 5 or 6 ring atoms (in the case of the compound of the formula (I-1), A and D, together with the atoms to which they are attached, then represent, for example, the groups AD-1 to AD-10 mentioned further below) which ring may contain oxygen or sulphur, or which may optionally contain one of the groups below

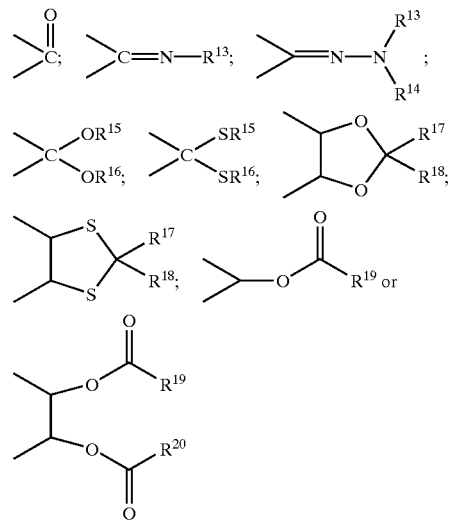

or

A and $Q^1$ together preferably represent $C_3$–$C_6$-alkanediyl or $C_4$–$C_6$-alkenediyl, each of which is optionally mono- or disubstituted by identical or different substituents selected from the group consisting of halogen, hydroxyl; $C_1$–$C_{10}$-alkyl, $C_1$–$C_6$-alkoxy, $C_1$–$C_6$-alkylthio, $C_3$–$C_7$-cycloalkyl, each of which is optionally mono- to trisubstituted by identical or different halogens; and benzyloxy and phenyl, each of which is optionally mono- to trisubstituted by identical or different substituents selected from the group consisting of halogen, $C_1$–$C_6$-alkyl or $C_1$–$C_6$-alkoxy, and which furthermore optionally contains one of the groups below

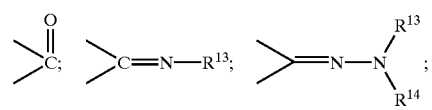

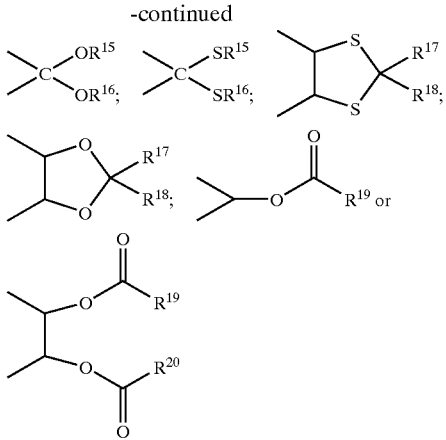

or is bridged by a $C_1$–$C_2$-alkanediyl group or by an oxygen atom, or $Q^1$ preferably represents hydrogen or $C_1$–$C_4$-alkyl.

$Q^2$, $Q^4$, $Q^5$ and $Q^6$ independently of one another each preferably represent hydrogen or $C_1$–$C_4$-alkyl.

$Q^3$ preferably represents hydrogen, $C_1$–$C_6$-alkyl, $C_1$–$C_6$-alkoxy-$C_1$–$C_2$-alkyl, $C_1$–$C_6$-alkylthio-$C_1$–$C_2$-alkyl, optionally $C_1$–$C_4$-alkyl- or $C_1$–$C_4$-alkoxy-substituted $C_3$–$C_8$-cycloalkyl in which optionally one methylene group is replaced by oxygen or sulphur or optionally halogen-, $C_1$–$C_4$-alkyl-, $C_1$–$C_4$-alkoxy-, $C_1$–$C_2$-halogenoalkyl-, $C_1$–$C_2$-halogenoalkoxy-, cyano- or nitro-substituted phenyl, or $Q^3$ and $Q^4$ together with the carbon atom to which they are attached preferably represent an optionally $C_1$–$C_4$-alkyl-, $C_1$–$C_4$-alkoxy- or $C_1$–$C_2$-halogenoalkyl-substituted $C_3$–$C_7$-ring in which optionally one ring member is replaced by oxygen or sulphur.

G preferably represents hydrogen (a) or represents one of the groups

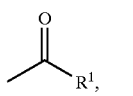 (b)

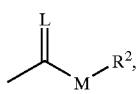 (c)

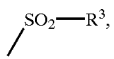 (d)

(e)

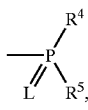

E or (f)

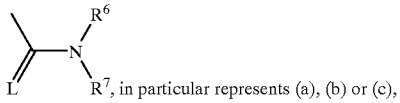 (g)

$R^7$, in particular represents (a), (b) or (c), in which
E represents a metal ion or an ammonium ion,
L represents oxygen or sulphur and
M represents oxygen or sulphur.

$R^1$ preferably represents in each case optionally halogen-substituted $C_1$–$C_{20}$-alkyl, $C_2$–$C_{20}$-alkenyl, $C_1$–$C_8$-alkoxy-$C_1$–$C_8$-alkyl, $C_1$–$C_8$-alkylthio-$C_1$–$C_8$-alkyl, poly-$C_1$–$C_8$-alkoxy-$C_1$–$C_8$-alkyl or optionally halogen-, $C_1$–$C_6$-alkyl- or $C_1$–$C_6$-alkoxy-substituted $C_3$–$C_8$-cycloalkyl in which optionally one or more (preferably not more than two) not directly adjacent ring members are replaced by oxygen and/or sulphur, represents optionally halogen-, cyano, nitro-, $C_1$–$C_6$-alkyl-, $C_1$–$C_6$-alkoxy-, $C_1$–$C_6$-halogenoalkyl-, $C_1$–$C_6$-halogenoalkoxy-, $C_1$–$C_6$-alkylthio- or $C_1$–$C_6$-alkylsulphonyl-substituted phenyl, represents optionally halogen-, nitro-, cyano-, $C_1$–$C_6$-alkyl-, $C_1$–$C_6$-alkoxy-, $C_1$–$C_6$-halogenoalkyl- or $C_1$–$C_6$-halogenoalkoxy-substituted phenyl-$C_1$–$C_6$-alkyl, represents optionally halogen- or $C_1$–$C_6$-alkyl-substituted 5- or 6-membered hetaryl (for example pyrazolyl, thiazolyl, pyridyl, pyrimidyl, furanyl or thienyl), represents optionally halogen- or $C_1$–$C_6$-alkyl-substituted phenoxy-$C_1$–$C_6$-alkyl or represents optionally halogen-, amino- or $C_1$–$C_6$-alkyl-substituted 5- or 6-membered hetaryloxy-$C_1$–$C_6$-alkyl (for example pyridyloxy-$C_1$–$C_6$-alkyl, pyrimidyloxy-$C_1$–$C_6$-alkyl or thiazolyloxy-$C_1$–$C_6$-alkyl).

$R^2$ preferably represents in each case optionally halogen-substituted $C_1$–$C_{20}$-alkyl, $C_2$–$C_{20}$-alkenyl, $C_1$–$C_8$-alkoxy-$C_2$–$C_8$-alkyl, poly-$C_1$–$C_8$-alkoxy-$C_2$–$C_8$-alkyl, represents optionally halogen-, $C_1$–$C_6$-alkyl- or $C_1$–$C_6$-alkoxy-substituted $C_3$–$C_8$-cycloalkyl or represents in each case optionally halogen-, cyano-, nitro-, $C_1$–$C_6$-alkyl-, $C_1$–$C_6$-alkoxy-, $C_1$–$C_6$-halogenoalkyl- or $C_1$–$C_6$-halogenoalkoxy-substituted phenyl or benzyl.

$R^3$ preferably represents optionally halogen-substituted $C_1$–$C_8$-alkyl or represents in each case optionally halogen-, $C_1$–$C_6$-alkyl-, $C_1$–$C_6$-alkoxy-, $C_1$–$C_4$-halogenoalkyl-, $C_1$–$C_4$-halogenoalkoxy-, cyano- or nitro-substituted phenyl or benzyl.

$R^4$ and $R^5$ independently of one another each preferably represent in each case optionally halogen-substituted $C_1$–$C_8$-alkyl, $C_1$–$C_8$-alkoxy, $C_1$–$C_8$-alkylamino, di-($C_1$–$C_8$-alkyl)amino, $C_1$–$C_8$-alkylthio, $C_2$–$C_8$-alkenylthio, $C_3$–$C_7$-cycloalkylthio or represent in each case optionally halogen-, nitro-, cyano-, $C_1$–$C_4$-alkoxy-, $C_1$–$C_4$-halogenoalkoxy-, $C_1$–$C_4$-alkylthio-, $C_1$–$C_4$-halogenoalkylthio-, $C_1$–$C_4$-alkyl- or $C_1$–$C_4$-halogen alkyl-substituted phenyl, phenoxy or phenylthio.

$R^6$ and $R^7$ independently of one another each preferably represent hydrogen, represent in each case optionally halogen-substituted $C_1$–$C_8$-alkyl, $C_3$–$C_8$-cycloalkyl, $C_1$–$C_8$-alkoxy, $C_3$–$C_8$-alkenyl, $C_1$–$C_8$-alkoxy-$C_1$–$C_8$-alkyl, represent optionally halogen-, $C_1$–$C_8$-halogenoalkyl-, $C_1$–$C_8$-alkyl- or $C_1$–$C_8$-alkoxy-substituted phenyl, optionally halogen-, $C_1$–$C_8$-alkyl-, $C_1$–$C_8$-halogenoalkyl- or $C_1$–$C_8$-alkoxy-substituted benzyl or together represent an optionally $C_1$–$C_4$-alkyl-substituted $C_3$–$C_6$-alkylene radical in which optionally one methylene group is replaced by oxygen or sulphur.

$R^{13}$ preferably represents hydrogen, represents in each case optionally halogen-substituted $C_1$–$C_8$-alkyl or $C_1$–$C_8$-alkoxy, represents optionally halogen-, $C_1$–$C_4$-alkyl- or $C_1$–$C_4$-alkoxy-substituted $C_3$–$C_8$-cycloalkyl in which optionally one methylene group is replaced by oxygen or sulphur, or represents in each case optionally halogen-, $C_1-C_6$-alkyl-, $C_1-C_6$-alkoxy-, $C_1-C_4$-halogenoalkyl-, $C_1-C_4$-halogenoalkoxy-, nitro- or cyano-substituted phenyl, phenyl-$C_1-C_4$-alkyl or phenyl-$C_1-C_4$-alkoxy.

$R^{14}$ preferably represents hydrogen or $C_1-C_8$-alkyl, or $R^{13}$ and $R^{14}$ together preferably represent $C_4-C_6$-alkanediyl.

$R^{15}$ and $R^{16}$ are identical or different and each preferably represent $C_1-C_6$-alkyl, or $R^{15}$ and $R^{16}$ together preferably represent a $C_2-C_4$-alkanediyl radical which is optionally substituted by $C_1-C_6$-alkyl, $C_1-C_6$-halogenoalkyl or by optionally halogen-, $C_1-C_6$-alkyl-, $C_1-C_4$-halogenoalkyl-, $C_1-C_6$-alkoxy-, $C_1-C_4$-halogenoalkoxy-, nitro- or cyano-substituted phenyl.

$R^{17}$ and $R^{18}$ independently of one another each preferably represent hydrogen, represent optionally halogen-substituted $C_1-C_8$-alkyl or represent optionally halogen-, $C_1-C_6$-alkyl-, $C_1-C_6$-alkoxy-, $C_1-C_4$-halogenoalkyl-, $C_1-C_4$-halogenoalkoxy-, nitro- or cyano-substituted phenyl, or $R^{17}$ and $R^{18}$ together with the carbon atom to which they are attached preferably represent a carbonyl group or represent optionally halogen-, $C_1-C_4$-alkyl- or $C_1-C_4$-alkoxy-substituted $C_5-C_7$-cycloalkyl in which optionally one methylene group is replaced by oxygen or sulphur.

$R^{19}$ and $R^{20}$ independently of one another each preferably represent $C_1-C_{10}$-alkyl, $C_2-C_{10}$-alkenyl, $C_1-C_{10}$-alkoxy, $C_1-C_{10}$-alkylamino, $C_3-C_{10}$-alkenylamino, di-($C_1-C_{10}$-alkyl)amino or di-($C_3-C_{10}$-alkenyl)amino.

In the preferred radical definitions, halogen represents fluorine, chlorine, bromine and iodine and in particular represents fluorine, chlorine and bromine.

X particularly preferably represents fluorine, chlorine, bromine, $C_1-C_4$-alkyl, $C_1-C_4$-alkoxy, $C_3-C_4$-alkenyloxy, $C_1-C_4$-halogenoalkyl, $C_1-C_4$-halogenoalkoxy, $C_3-C_4$-halogenoalkenyloxy, nitro or cyano.

Z particularly preferably represents one of the radicals

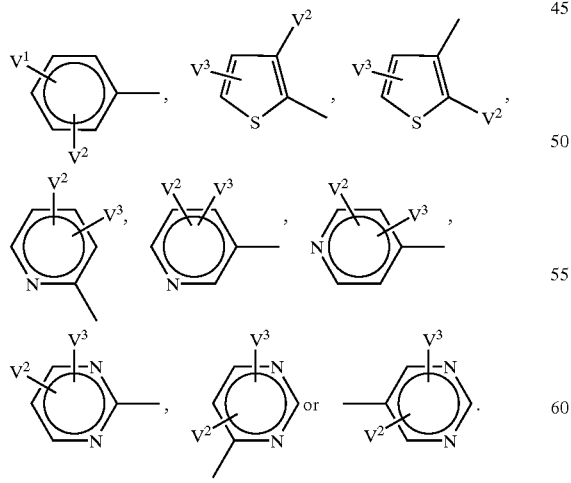

$V^1$ particularly preferably represents hydrogen, fluorine, chlorine, bromine, $C_1-C_6$-alkyl, $C_1-C_4$-alkoxy, $C_1-C_2$-halogenoalkyl, $C_1-C_2$-halogenoalkoxy, nitro, cyano or phenyl, phenoxy, phenoxy-$C_1-C_2$-alkyl, phenyl-$C_1-C_2$-alkoxy, phenylthio-$C_1-C_2$-alkyl or phenyl-$C_1-C_2$-alkylthio, each of which is optionally mono- or disubstituted by fluorine, chlorine, bromine, $C_1-C_4$-alkyl, $C_1-C_4$-alkoxy, $C_1-C_2$-halogenoalkyl, $C_1-C_2$-halogenoalkoxy, nitro or cyano.

$V^2$ and $V^3$ independently of one another each particularly preferably represent hydrogen, fluorine, chlorine, bromine, $C_1-C_4$-alkyl, $C_1-C_4$-alkoxy, $C_1-C_2$-halogenoalkyl or $C_1-C_2$-halogenoalkoxy.

W and Y independently of one another each particularly preferably represent hydrogen, fluorine, chlorine, bromine, $C_1-C_4$-alkyl, $C_1-C_4$-halogenoalkyl, $C_1-C_4$-alkoxy or $C_1-C_4$-halogenoalkoxy.

CKE particularly preferably represents one of the groups

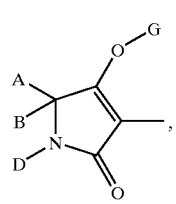

(1)

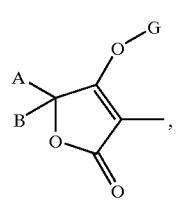

(2)

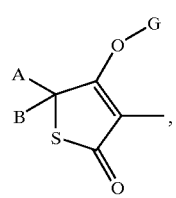

(3)

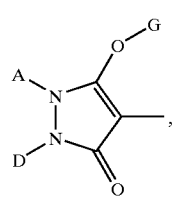

(4)

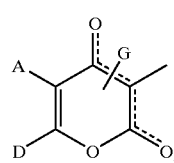

(5)

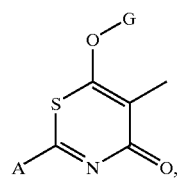

(6)

-continued

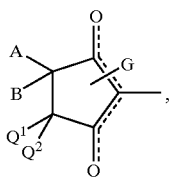
(7)

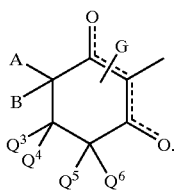
(8)

A particularly preferably represents hydrogen or represents in each case optionally fluorine- or chlorine-substituted $C_1$–$C_{10}$-alkyl, $C_1$–$C_8$-alkoxy-$C_1$–$C_6$-alkyl, optionally fluorine-, chlorine-, $C_1$–$C_4$-alkyl- or $C_1$–$C_4$-alkoxy-substituted $C_3$–$C_7$-cycloalkyl in which optionally one ring member is replaced by oxygen or sulphur or (but not in the case of the compounds of the formulae (I-5), (I-7) and (I-8)) in each case optionally fluorine-, chlorine-, bromine-, $C_1$–$C_4$-alkyl-, $C_1$–$C_4$-halogenoalkyl-, $C_1$–$C_4$-alkoxy- or $C_1$–$C_4$-halogenoalkoxy-substituted phenyl, furanyl, pyridyl, imidazolyl, triazolyl, pyrazolyl, pyrimidyl, thiazolyl, thienyl or phenyl-$C_1$–$C_4$-alkyl.

B particularly preferably represents hydrogen or $C_1$–$C_6$-alkyl, or

A, B and the carbon atom to which they are attached particularly preferably represent saturated or unsaturated $C_5$–$C_7$-cycloalkyl in which optionally one ring member is replaced by oxygen or sulphur and which is optionally monosubstituted by $C_1$–$C_6$-alkyl, $C_5$–$C_8$-cycloalkyl, $C_1$–$C_3$-halogenoalkyl, $C_1$–$C_6$-alkoxy, fluorine, chlorine or phenyl, or A, B and the carbon atom to which they are attached particularly preferably represent $C_5$–$C_6$-cycloalkyl which is substituted by an alkylenediyl group which optionally contains one or two not directly adjacent oxygen or sulphur atoms or by an alkylenedioxyl group or by an alkylenedithiol group which, together with the carbon atom to which it is attached, forms a further five- or six-membered ring, or A, B and the carbon atom to which they are attached particularly preferably represent $C_3$–$C_6$-cycloalkyl or $C_5$–$C_6$-cycloalkenyl in which two substituents together with the carbon atoms to which they are attached represent in each case optionally $C_1$–$C_5$-alkyl-, $C_1$–$C_5$-alkoxy-, fluorine-, chlorine- or bromine-substituted $C_2$–$C_4$-alkanediyl or $C_2$–$C_4$-alkenediyl, in which optionally one methylene group is replaced by oxygen or sulphur, or represent butadienediyl.

D particularly preferably represents hydrogen, represents in each case optionally fluorine- or chlorine-substituted $C_1$–$C_{10}$-alkyl, $C_3$–$C_6$-alkenyl, $C_1$–$C_8$-alkoxy-$C_2$–$C_6$-alkyl or $C_1$–$C_8$-alkylthio-$C_2$–$C_6$-alkyl, represents optionally fluorine-, chlorine-, $C_1$–$C_4$-alkyl-, $C_1$–$C_4$-alkoxy- or $C_1$–$C_2$-halogenoalkyl-substituted $C_3$–$C_7$-cycloalkyl in which optionally one methylene group is replaced by oxygen or sulphur or (but not in the case of the compounds of the formulae (I-1) and (I-4)) represents in each case optionally fluorine-, chlorine-, bromine-, $C_1$–$C_4$-alkyl-, $C_1$–$C_4$-halogenoalkyl-, $C_1$–$C_4$-alkoxy- or $C_1$–$C_4$-halogenoalkoxy-substituted phenyl, furanyl, imidazolyl, pyridyl, thiazolyl, pyrazolyl, pyrimidyl, pyrrolyl, thienyl, triazolyl or phenyl-$C_1$–$C_4$-alkyl, or A and D together particularly preferably represent optionally substituted $C_3$–$C_5$-alkanediyl in which one methylene group may be replaced by a carbonyl group, oxygen or sulphur, possible substituents being hydroxyl, $C_1$–$C_6$-alkyl or $C_1$–$C_4$-alkoxy, or A and D (in the case of the compounds of the formula (I-1)) together with the atoms to which they are attached represent one of the groups AD-1 to AD-10:

AD-1
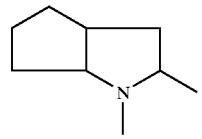

AD-2
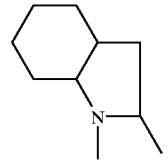

AD-3
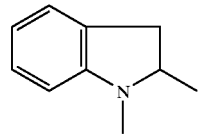

AD-4
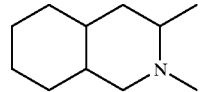

AD-5
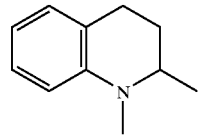

AD-6
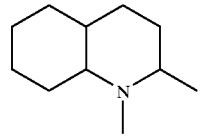

AD-7
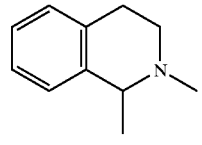

AD-8
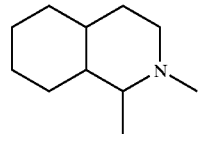

-continued

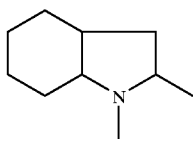
AD-9

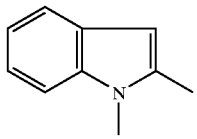
AD-10

A and $Q^1$ together particularly preferably represent $C_3$–$C_4$-alkanediyl or $C_3$–$C_4$-alkenediyl, each of which is optionally mono- or disubstituted by identical or different substituents selected from the group consisting of fluorine, chlorine, hydroxyl, and $C_1$–$C_8$-alkyl and $C_1$–$C_4$-alkoxy, each of which is optionally mono- to trisubstituted by fluorine, or $Q^1$ particularly preferably represents hydrogen.

$Q^2$ particularly preferably represents hydrogen.

$Q^4$, $Q^5$ and $Q^6$ independently of one another each particularly preferably represent hydrogen or $C_1$–$C_3$-alkyl.

$Q^3$ particularly preferably represents hydrogen, $C_1$–$C_4$-alkyl, $C_1$–$C_4$-alkoxy-$C_1$–$C_2$-alkyl, $C_1$–$C_4$-alkylthio-$C_1$–$C_2$-alkyl or optionally methyl- or methoxy-substituted $C_3$–$C_6$-cycloalkyl in which optionally one methylene group is replaced by oxygen or sulphur, or $Q^3$ and $Q^4$ together with the carbon atom to which they are attached particularly preferably represent an optionally $C_1$–$C_4$-alkyl- or $C_1$–$C_4$-alkoxy-substituted saturated $C_5$–$C_6$-ring in which optionally one ring member is replaced by oxygen or sulphur.

G particularly preferably represents hydrogen (a) or particularly preferably represents one of the groups

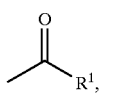 (b)

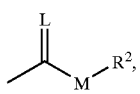 (c)

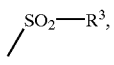 (d)

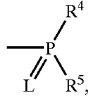 (e)

E or (f)

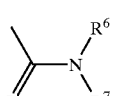, in particular represents (a), (b) or (c), (g)

in which
E represents a metal ion or an ammonium ion,
L represents oxygen or sulphur and
M represents oxygen or sulphur.

$R^1$ particularly preferably represents in each case optionally fluorine- or chlorine-substituted $C_1$–$C_{16}$-alkyl, $C_2$–$C_{16}$-alkenyl, $C_1$–$C_6$-alkoxy-$C_1$–$C_6$-alkyl, $C_1$–$C_6$-alkylthio-$C_1$–$C_6$-alkyl, poly-$C_1$–$C_6$-alkoxy-$C_1$–$C_6$-alkyl or optionally fluorine-, chlorin-, $C_1$–$C_5$-alkyl- or $C_1$–$C_5$-alkoxy-substituted $C_3$–$C_7$-cycloalkyl in which optionally one or two not directly adjacent ring members are replaced by oxygen and/or sulphur, represents optionally fluorine-, chlorine-, bromine-, cyano-, nitro-, $C_1$–$C_4$-alkyl-, $C_1$–$C_4$-alkoxy-, $C_1$–$C_3$-hatogenoalkyl-, $C_1$–$C_3$-halogenoalkoxy-, $C_1$–$C_4$-alkylthio- or $C_1$–$C_4$-alkylsulphonyl-substituted phenyl, represents optionally fluorine-, chlorine-, bromine-, $C_1$–$C_4$-alkyl-, $C_1$–$C_4$-alkoxy-, $C_1$–$C_3$-halogenoalkyl- or $C_1$–$C_3$-halogenoalkoxy-substituted phenyl-$C_1$–$C_4$-alkyl, represents in each case optionally fluorine-, chlorine-, bromine- or $C_1$–$C_4$-alkyl-substituted pyrazolyl, thiazolyl, pyridyl, pyrimidyl, furanyl or thienyl, represents optionally fluorine-, chlorine-, bromine- or $C_1$–$C_4$-alkyl-substituted phenoxy-$C_1$–$C_3$-alkyl or represents in each case optionally fluorine-, chlorine-, bromine-, amino- or $C_1$–$C_4$-alkyl-substituted pyridyloxy-$C_1$–$C_3$-alkyl, pyrimidyloxy-$C_1$–$C_3$-alkyl or thiazolyloxy-$C_1$–$C_3$-alkyl.

$R^2$ particularly preferably represents in each case optionally fluorine-substituted $C_1$–$C_{16}$-alkyl, $C_2$–$C_{16}$-alkenyl, $C_1$–$C_6$-alkoxy-$C_2$–$C_6$-alkyl or poly-$C_1$–$C_6$-alkoxy-$C_2$–$C_6$-alkyl, represents optionally fluorine-, chlorine-, $C_1$–$C_4$-alkyl- or $C_1$–$C_4$-alkoxy-substituted $C_3$–$C_7$-cycloalkyl or represents in each case optionally fluorine-, chlorine-, bromine-, cyano-, nitro, -$C_1$–$C_4$-alkyl-, $C_1$–$C_3$-alkoxy-, $C_1$–$C_3$-halogenoalkyl- or $C_1$–$C_3$-halogenoalkoxy-substituted phenyl or benzyl.

$R^3$ particularly preferably represents optionally fluorine-substituted $C_1$–$C_6$-alkyl or particularly preferably represents in each case optionally fluorine-, chlorine-, bromine-, $C_1$–$C_4$-alkyl-, $C_1$–$C_4$-alkoxy-, $C_1$–$C_3$-halogenoalkyl-, $C_1$–$C_3$-halogenoalkoxy-, cyano- or nitro-substituted phenyl or benzyl.

$R^4$ and $R^5$ independently of one another each particularly preferably represent $C_1$–$C_6$-alkyl, $C_1$–$C_6$-alkoxy, $C_1$–$C_6$-alkylamino, di-($C_1$–$C_6$-alkyl)amino, $C_1$–$C_6$-alkylthio, $C_3$–$C_4$-alkenylthio, $C_3$–$C_6$-cycloalkylthio or represent in each case optionally fluorine-, chlorine-, bromine-, nitro-, cyano-, $C_1$–$C_3$-alkoxy-, $C_1$–$C_3$-halogenoalkoxy-, $C_1$–$C_3$-alkylthio-, $C_1$–$C_3$-halogenoalkylthio-, $C_1$–$C_3$-alkyl- or $C_1$–$C_3$-halogenoalkyl-substituted phenyl, phenoxy or phenylthio.

$R^6$ and $R^7$ independently of one another each particularly preferably represent hydrogen, $C_1$–$C_6$-alkyl, $C_3$–$C_6$-cycloalkyl, $C_1$–$C_6$-alkoxy, $C_3$–$C_6$-alkenyl, $C_1$–$C_6$-alkoxy-$C_1$–$C_6$-alkyl, represent optionally fluorine-, chlorine-, bromine-, $C_1$–$C_3$-halogenoalkyl-, $C_1$–$C_4$-alkyl- or $C_1$–$C_4$-alkoxy-substituted phenyl, represent optionally fluorine-, chlorine-, bromine-, $C_1$–$C_4$-alkyl-, $C_1$–$C_3$-halogenoalkyl- or $C_1$–$C_4$-alkoxy-substituted benzyl, or together represent an optionally methyl- or ethyl-substituted $C_4$–$C_5$-alkylene radical in which optionally one methylene group is replaced by oxygen or sulphur.

In the particularly preferred radical definitions, halogen represents fluorine, chlorine, bromine and iodine, in particular represents fluorine, chlorine and bromine.

X very particularly preferably represents fluorine, chlorine, methyl, ethyl, propyl, iso-propyl, methoxy, ethoxy, propoxy, iso-propoxy, trifluoromethyl, difluoromethoxy, trifluoromethoxy, nitro or cyano.

Z very particularly preferably represents one of the radicals

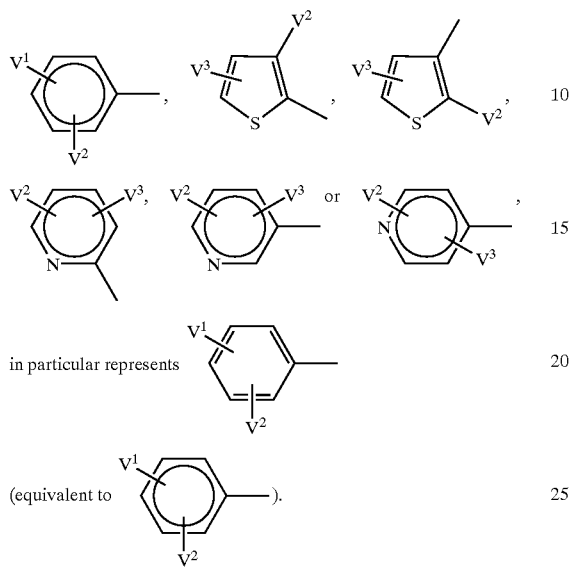

in particular represents (equivalent to ).

V¹ very particularly preferably represents hydrogen, fluorine, chlorine, bromine, methyl, ethyl, n-propyl, iso-propyl, n-butyl, iso-butyl, tert-butyl, methoxy, ethoxy, n-propoxy, iso-propoxy, trifluoromethyl, trifluoromethoxy, nitro, cyano or phenyl which is optionally monosubstituted by fluorine, chlorine, methyl, methoxy, trifluoromethyl or trifluoromethoxy.

V² and V³ independently of one another each very particularly preferably represent hydrogen, fluorine, chlorine, methyl, ethyl, n-propyl, iso-propyl, methoxy, ethoxy, trifluoromethyl or trifluoromethoxy.

W and Y independently of one another each very particularly preferably represent hydrogen, fluorine, chlorine, methyl, ethyl, n-propyl, methoxy, ethoxy or propoxy.

CKE very particularly preferably represents one of the groups (1)

(2)

(3)

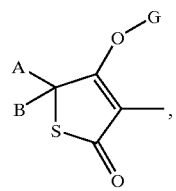

(4)

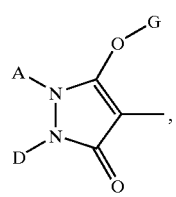

(5)

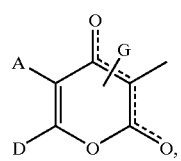

(6)

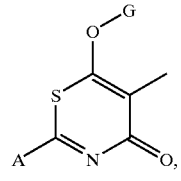

(7)

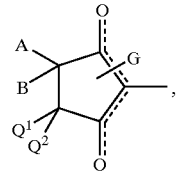

(8)

A very particularly preferably represents hydrogen or represents in each case optionally fluorine-substituted $C_1$–$C_8$-alkyl or $C_1$–$C_6$-alkoxy-$C_1$–$C_4$-alkyl, optionally fluorine-, methyl-, ethyl- or methoxy-substituted $C_3$–$C_6$-cycloalkyl in which optionally one ring member is replaced by oxygen or sulphur or (but not in the case of the compounds of the formulae (I-5), (I-7) and (I-8)) represents in each case optionally fluorine-, chlorine-, bromine-, methyl-, ethyl-, n-propyl-, iso-propyl-, methoxy-, ethoxy-, trifluoromethyl-, trifluoromethoxy-, cyano- or nitro-substituted phenyl or benzyl.

B very particularly preferably represents hydrogen or $C_1$–$C_4$-alkyl, or

A, B and the carbon atom to which they are attached very particularly preferably represent saturated $C_5$–$C_6$-cycloalkyl in which optionally one ring member is replaced by oxygen or sulphur and which is optionally monosubstituted by methyl, ethyl, propyl, isopropyl, butyl, iso-butyl, sec-butyl, tert-butyl, trifluoromethyl, methoxy, ethoxy, propoxy, iso-propoxy, butoxy, iso-butoxy, sec-butoxy, tert-butoxy, fluorine or chlorine, or A, B and the carbon atom to which they are attached very particularly preferably represent $C_5$–$C_6$-cycloalkyl or $C_5$–$C_6$-cycloalkenyl in which two substituents together with the carbon atoms to which they are attached represent $C_2$–$C_4$ alkanediyl or $C_2$–$C_4$-alkenediyl in which in each case optionally one methylene group is replaced by oxygen or sulphur, or represent butadienediyl D very particularly preferably represents hydrogen, represents in each case optionally fluorine- or chlorine-substituted $C_1$–$C_8$-alkyl, $C_3$–$C_4$-alkenyl, $C_1$–$C_6$-alkoxy-$C_2$–$C_4$-alkyl, $C_1$–$C_4$-alkylthio-$C_2$–$C_4$-alkyl or $C_3$–$C_6$-cycloalkyl in which optionally one methylene group is replaced by oxygen or sulphur or (but not in the case of the compounds of the formulae (I-1) and (I-4)) represents in each case optionally fluorine-, chlorine-, methyl-, ethyl-, n-propyl-, iso-propyl-, methoxy-, ethoxy-, trifluoromethyl- or trifluoromethoxy-substituted phenyl, furanyl, pyridyl, thienyl or benzyl, or A and D together very particularly preferably represent optionally substituted $C_3$–$C_4$-alkanediyl in which optionally one carbon atom is replaced by sulphur and which is optionally substituted by hydroxyl, methyl, ethyl, methoxy or ethoxy, or A and D (in the case of the compounds of the formula (I-1)) together with the atoms to which they are attached represent one of the following groups AD:

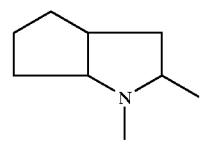

AD-1

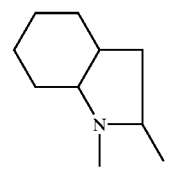

AD-2

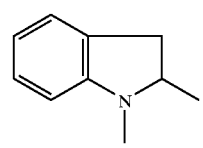

AD-3

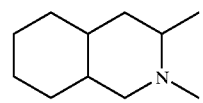

AD-4

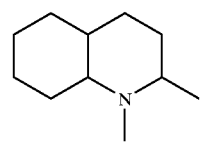

AD-6

-continued

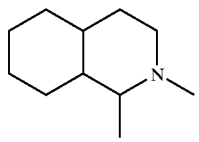

AD-8

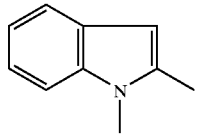

AD-10

A and $Q^1$ together very particularly preferably represent $C_3$–$C_4$-alkanediyl or butenediyl, each of which is optionally mono- or disubstituted by fluorine, hydroxyl, methyl or methoxy, or $Q^1$ very particularly preferably represents hydrogen.

$Q^2$ very particularly preferably represents hydrogen.

$Q^4$, $Q^5$ and $Q^6$ independently of one another each very particularly preferably represent hydrogen, methyl or ethyl.

$Q^3$ very particularly preferably represents hydrogen, methyl, ethyl or $C_3$–$C_6$-cycloalkyl in which optionally one methylene group is replaced by oxygen or sulphur, or $Q^3$ and $Q^4$ together with the carbon to which they are attached very particularly preferably represent an optionally methyl- or methoxy-substituted saturated $C_5$–$C_6$-ring in which optionally one ring member is replaced by oxygen or sulphur.

G very particularly preferably represents hydrogen (a) or represents one of the groups

(b)

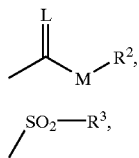

(c)

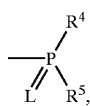

(d)

(e)

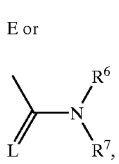

(f)

E or (g)

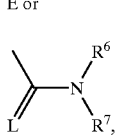

, in particular represents (a), (b) or (c), in which

E represents a metal ion or an ammonium ion,

L represents oxygen or sulphur and

M represents oxygen or sulphur.

$R^1$ very particularly preferably represents in each case optionally fluorine- or chlorine-substituted $C_1$–$C_{14}$-alkyl, $C_2$–$C_{14}$-alkenyl, $C_1$–$C_4$-alkoxy-$C_1$–$C_6$-alkyl, $C_1$–$C_4$-alkylthio-$C_1$–$C_6$-alkyl, poly-$C_1$–$C_4$-alkoxy-$C_1$–$C_4$-alkyl or optionally fluorine-, chlorine-, methyl-, ethyl-, propyl-, i-propyl-, butyl-, i-butyl-, tert-butyl-, methoxy-, ethoxy-, n-propoxy- or iso-propoxy-substituted $C_3$–$C_6$-cycloalkyl in which optionally one or two not directly adjacent ring members are replaced by oxygen and/or sulphur, represents optionally fluorine-, chlorine-, bromine-, cyano-, nitro-, methyl-, ethyl-, n-propyl-, 1-propyl-, methoxy-, ethoxy-, trifluoromethyl-, trifluoromethoxy-, methylthio-, ethylthio-, methylsulphonyl- or ethylsulphonyl-substituted phenyl, represents optionally fluorine-, chlorine-, bromine-, methyl-, ethyl-, n-propyl-, i-propyl-, methoxy-, ethoxy-, trifluoromethyl- or trifluoromethoxy-substituted benzyl, represents in each case optionally fluorine-, chlorine-, bromine-, methyl- or ethyl-substituted furanyl, thienyl, pyridyl, pyrimidyl, thiazolyl or pyrazolyl, represents optionally fluorine-, chlorine-, methyl- or ethyl-substituted phenoxy-$C_1$–$C_2$-alkyl or represents in each case optionally fluorine-, chlorine-, amino-, methyl- or ethyl-substituted pyridyloxy-$C_1$–$C_2$-alkyl, pyrimidyloxy-$C_1$–$C_2$-alkyl or thiazolyloxy-$C_1$–$C_2$-alkyl.

$R^2$ very particularly preferably represents in each case optionally fluorine-substituted $C_1$–$C_{14}$-alkyl, $C_2$–$C_{14}$-alkenyl, $C_1$–$C_4$-alkoxy-$C_2$–$C_6$-alkyl or poly-$C_1$–$C_4$-alkoxy-$C_2$–$C_6$-alkyl, represents optionally fluorine-, chlorine-, methyl-, ethyl-, n-propyl-, isopropyl- or methoxy-substituted $C_3$–$C_6$-cycloalkyl, or represents in each case optionally fluorine-, chlorine-, cyano-, nitro-, methyl-, ethyl-, n-propyl-, i-propyl-, methoxy-, ethoxy-, trifluoromethyl- or trifluoromethoxy-substituted phenyl or benzyl.

$R^3$ very particularly preferably represents in each case optionally fluorine-substituted methyl, ethyl, n-propyl, isopropyl or in each case optionally fluorine-, chlorine-, bromine-, methyl-, tert-butyl-, methoxy-, trifluoromethyl-, trifluoromethoxy-, cyano- or nitro-substituted phenyl or benzyl.

$R^4$ and $R^5$ independently of one another each very particularly preferably represent $C_1$–$C_4$-alkyl, $C_1$–$C_4$-alkoxy, $C_1$–$C_4$-alkylamino, di-($C_1$–$C_4$-alkyl)amino, $C_1$–$C_4$-alkylthio or represent in each case optionally fluorine-, chlorine-, bromine-, nitro-, cyano-, $C_1$–$C_2$-, alkoxy-, $C_1$–$C_2$-fluoroalkoxy-, $C_1$–$C_2$-alkylthio-, $C_1$–$C_2$-fluoroalkylthio- or $C_1$–$C_3$-alkyl-substituted phenyl, phenoxy or phenylthio.

$R^6$ and $R^7$ independently of one another each very particularly preferably represent hydrogen, represent $C_1$–$C_4$-alkyl, $C_3$–$C_6$-cycloalkyl, $C_1$–$C_4$-alkoxy, $C_3$–$C_4$-alkenyl, $C_1$–$C_4$-alkoxy-$C_1$–$C_4$-alkyl, represent optionally fluorine-, chlorine-, bromine-, trifluoromethyl-, methyl- or methoxy-substituted phenyl, represent optionally fluorine-, chlorine-, bromine-, methyl-, trifluoromethyl- or methoxy-substituted benzyl, or together represent a $C_5$–$C_6$-alkylene radical in which optionally one methylene group is replaced by oxygen or sulphur.

The abovementioned general or preferred radical definitions or illustrations can be combined with each other as desired, i.e. including combinations between the respective ranges and preferred ranges. They apply both to the end products and, correspondingly, to the precursors and intermediates.

Preference according to the invention is given to the compounds of the formula (I) which contain a combination of the meanings listed above as being preferred (preferable).

Particular preference according to the invention is given to the compounds of the formula (I) which contain a combination of the meanings listed above as being particularly preferred.

Very particular preference according to the invention is given to the compounds of the formula (I) which contain a combination of the meanings listed above as being very particularly preferred.

Saturated or unsaturated hydrocarbon radicals such as alkyl or alkenyl may in each case be straight-chain or branched as far as this is possible, including in combination with heteroatoms, such as, for example, in alkoxy.

Unless stated otherwise, optionally substituted radicals may be mono- or polysubstituted, and in the case of polysubstitutions the substituents may be identical or different.

Besides the compounds mentioned in the Preparation Examples, the following compounds of the formula (I-1-a) may be specifically mentioned:

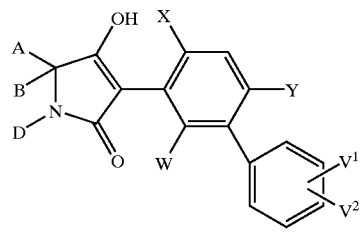

TABLE 1

| W = H; X = CH₃, Y = H, V¹ = H, V² = H. | | |
|---|---|---|
| A | B | D |
| $CH_3$ | H | H |
| $C_2H_5$ | H | H |
| $C_3H_7$ | H | H |
| i-$C_3H_7$ | H | H |
| $C_4H_9$ | H | H |
| i-$C_4H_9$ | H | H |
| s-$C_4H_9$ | H | H |
| t-$C_4H_9$ | H | H |
| $CH_3$ | $CH_3$ | H |
| $C_2H_5$ | $CH_3$ | H |
| $C_3H_7$ | $CH_3$ | H |
| i-$C_3H_7$ | $CH_3$ | H |
| $C_4H_9$ | $CH_3$ | H |
| i-$C_4H_9$ | $CH_3$ | H |
| s-$C_4H_9$ | $CH_3$ | H |
| t-$C_4H_9$ | $CH_3$ | H |
| $C_2H_5$ | $C_2H_5$ | H |
| $C_3H_7$ | $C_3H_7$ | H |
| cyclopropyl | $CH_3$ | H |
| cyclopentyl | $CH_3$ | H |
| cyclohexyl | $CH_3$ | H |
| —(CH₂)₂— | | H |
| —(CH₂)₄— | | H |
| —(CH₂)₅— | | H |

TABLE 1-continued

W = H; X = CH₃, Y = H, V¹ = H, V² = H.

| A | B | D |
|---|---|---|
|  | —(CH₂)₆— | H |
|  | —(CH₂)₇— | H |
|  | —(CH₂)₂—O—(CH₂)₂— | H |
|  | —CH₂—O—(CH₂)₃— | H |
|  | —(CH₂)₂—S—(CH₂)₂— | H |
|  | —CH₂—CHCH₃—(CH₂)₃— | H |
|  | —(CH₂)₂—CHCH₃—(CH₂)₂— | H |
|  | —(CH₂)₂—CHC₂H₅—(CH₂)₂— | H |
|  | —(CH₂)₂—CHC₃H₇—(CH₂)₂— | H |
|  | —(CH₂)₂—CHi-C₃H₇—(CH₂)₂— | H |
|  | —(CH₂)₂—CHOCH₃—(CH₂)₂— | H |
|  | —(CH₂)₂—CHOC₂H₅—(CH₂)₂— | H |
|  | —(CH₂)₂—CHOC₃H₇—(CH₂)₂— | H |
|  | —(CH₂)₂—CHi-C₃H₇—(CH₂)₂— | H |
|  | —(CH₂)₂—C(CH₃)₂—(CH₂)₂— | H |
|  | —CH₂—(CHCH₃)₂—(CH₂)₂— | H |
|  | —CH₂—CH—(CH₂)₂—CH— with —CH₂— bridge | H |
|  | —CH₂—CH—CH—CH₂— with —(CH₂)₄— bridge | H |
|  | —CH₂—CH—CH—(CH₂)₂— with —(CH₂)₃— bridge | H |
|  | indane-diyl | H |
|  | tetralin-diyl | H |
|  | —(CH₂)₃— | H |
|  | —(CH₂)₄— | H |
|  | —CH₂—CHCH₃—CH₂— | H |
|  | —CH₂—CH₂—CHCH₃— | H |
|  | —CH₂—CHCH₃—CHCH₃— | H |
|  | —CH₂—S—CH₂— | H |
|  | —CH₂—S—(CH₂)₂— | H |
|  | —(CH₂)₂—S—CH₂— | H |
|  | —CH₂—CH—CH— with —(CH₂)₃— bridge | H |
| H | CH₃ | H |
| H | CH₂H₅ | H |
| H | C₃H₇ | H |
| H | i-C₃H₇ | H |
| H | cyclopropyl | H |
| H | cyclopentylmethyl | H |
| H | cyclohexyl | H |
| CH₃ | CH₃ | H |
| CH₃ | C₂H₅ | H |
| CH₃ | C₃H₇ | H |
| CH₃ | i-C₃H₇ | H |
| CH₃ | cyclopropyl | H |
| CH₃ | cyclopentylmethyl | H |
| CH₃ | cyclohexyl | H |
| C₂H₅ | CH₃ | H |
| C₂H₅ | C₂H₅ | H |

Table 2: A, B and D are each as given in Table 1 W=H; X=CH₃; Y=C₃; V¹=H; V²=H.
Table 3: A, B and D are each as given in Table 1 W=C₃; X=C₃; Y=CH₃; V¹=H; V²=H.
Table 4: A, B and D are each as given in Table 1 W=H; X=CH₃; Y=H; V¹=4-Cl; V²=H.
Table 5: A, B and D are each as given in Table 1 W=H; X=CH₃; Y=CH₃; V¹=4-Cl; V²=H.
Table 6: A, B and D are each as given in Table 1 W=CH₃; X=CH₃; Y=CH₃; V¹=4-Cl; V²=H.
Table 7: A, B and D are each as given in Table 1 W=H; X=CH₃; Y=H; V¹=3-Cl; V²=H.
Table 8: A, B and D are each as given in Table 1 W=H; X=CH₃; Y=CH₃; V¹=3-Cl; V²=H.
Table 9: A, B and D are each as given in Table 1 W=CH₃; X=CH₃; Y=C₃; V¹=3-Cl; V²=H.
Table 10: A, B and D are each as given in Table 1 W=H; X=CH₃; Y=H; V¹=2-Cl; V²=4-Cl.
Table 11: A, B and D are each as given in Table 1 W=H; X=CH₃; Y=CH₃; V¹=2-Cl; V²=4-Cl.
Table 12: A, B and D are each as given in Table 1 W=CH₃; X=CH₃; Y=CH₃; V¹=2-Cl; V²=4-Cl.
Table 13: A, B and D are each as given in Table 1 W=H; X=C₃; Y=H; V¹=4-CF₃; V²=H.
Table 14: A, B and D are each as given in Table 1 W=H; X=CH₃; Y=CH₃; V¹4-CF₃; V²=H.
Table 15: A, B and D are each as given in Table 1 W=CH₃; X=CH₃; Y=C₃; V¹=4-CF₃; V²=H.
Table 16: A, B and D are each as given in Table 1 W=H; X=CH₃; Y=H; V¹=4-CH₃; V²=H.
Table 17: A, B and D are each as given in Table 1 W=H; X=CH₃; Y=CH₃; V¹=4-CH₃; V²=H.
Table 18: A, B and D are each as given in Table 1 W=CH₃; X=CH₃; Y=CH₃; V¹=4-CH₃; V²=H.
Table 19: A, B and D are each as given in Table 1 W=H; X=CH₃; Y=H; V¹=4-OCH₃; V²=H.
Table 20: A, B and D are each as given in Table 1 W=H; X=CH₃; Y=CH₃; V¹=4-OCH₃; V²=H.
Table 21: A, B and D are each as given in Table 1 W=CH₃; X=CH₃; Y=CH₃; V¹=4-OCH₃; V²=H.

Besides the compounds mentioned in the Preparation Examples, the following compounds of the formula (I-2-a) may be specifically mentioned:

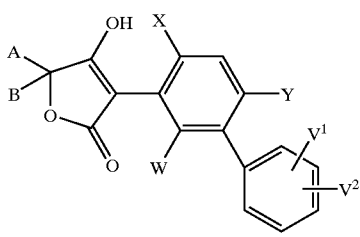

TABLE 22

| W = H; X = CH₃, Y = H, V¹ = H, V₂ = H. | |
|---|---|
| A | B |
| CH₃ | H |
| C₂H₅ | H |
| C₃H₇ | H |
| i-C₃H₇ | H |
| C₄H₉ | H |
| i-C₄H₉ | H |
| s-C₄H₉ | H |
| t-C₄H₉ | H |
| CH₃ | CH₃ |
| C₂H₅ | CH₃ |
| C₃H₇ | CH₃ |
| i-C₃H₇ | CH₃ |
| C₄H₉ | CH₃ |
| i-C₄H₉ | CH₃ |
| s-C₄H₉ | CH₃ |
| t-C₄H₉ | CH₃ |
| C₂H₅ | C₂H₅ |
| C₃H₇ | C₃H₇ |
| △ (cyclopropyl) | CH₃ |
| cyclopentyl-CH | CH₃ |
| cyclohexyl-CH | CH₃ |
| —(CH₂)₂— | |
| —(CH₂)₄— | |
| —(CH₂)₅— | |
| —(CH₂)₆— | |
| —(CH₂)₇— | |
| —(CH₂)₂—O—(CH₂)₂— | |
| —CH₂—O—(CH₂)₃— | |
| —(CH₂)₂—S—(CH₂)₂— | |
| —CH₂—CHCH₃—(CH₂)₃— | |
| —(CH₂)₂—CHCH₃—(CH₂)₂— | |
| (CH₂)₂—CHC₂H₅—(CH₂)₂— | |
| —(CH₂)₂—CHC₃H₇—(CH₂)₂— | |
| —(CH₂)₂—CHi-C₃H₇—(CH₂)₂— | |
| —(CH₂)₂—CHOCH₃—(CH₂)₂— | |
| —(CH₂)₂—CHOC₂H₅—(CH₂)₂— | |
| —(CH₂)₂—CHOC₃H₇—(CH₂)₂— | |
| —(CH₂)₂—CHi-C₃H₇—(CH₂)₂— | |
| —(CH₂)₂—C(CH₃)₂—(CH₂)₂— | |
| —CH₂—(CHCH₃)₂—(CH₂)₂— | |
| —CH₂—CH—(CH₂)₂—CH— with —CH₂— bridge | |
| —CH₂—CH—CH—CH₂— with —(CH₂)₄— bridge | |

TABLE 22-continued

| W = H; X = CH₃, Y = H, V¹ = H, V₂ = H. | |
|---|---|
| A | B |
| —CH₂—CH—CH—(CH₂)₂— with —(CH₂)₃— bridge | |
| indane fused | |
| tetrahydronaphthalene fused | |

Table 23: A and B are each as given in Table 22 W=H; X=CH₃; Y=CH₃; V²=H.

Table 24: A and B are each as given in Table 22 W=CH₃; X=CH₃; Y=CH₃; V¹=H; V²=H.

Table 25: A and B are each as given in Table 22 W=H; X=CH₃; Y=H; V¹=4-Cl; V²=H.

Table 26: A and B are each as given in Table 22 W=H; X=CH₃; Y=CH₃; V¹=4-Cl; V²=H.

Table 27: A and B are each as given in Table 22 W=CH₃; X=CH₃; Y=CH₃; V¹=4-Cl; V²=H.

Table 28: A and B are each as given in Table 22 W=H; X=CH₃; Y=H; V¹=3-Cl; V²=H.

Table 29: A and B are each as given in Table 22 W=H; X=CH₃; Y=CH₃; V¹=3-Cl; V²=H.

Table 30: A and B are each as given in Table 22 W=CH₃; X=CH₃; Y=CH₃; V¹=3-Cl; V²=H.

Table 31: A and B are each as given in Table 22 W=H, X=CH₃; Y=H; V¹=4-CF₃; V²=H.

Table 32: A and B are each as given in Table 22 W=H; X=CH₃; Y=CH₃; V¹=4-CF₃; V²=H.

Table 33: A and B are each as given in Table 22 W=CH₃; X=CH₃; Y=CH₃; V¹=4-CF₃; V²=H.

Table 34: A and B are each as given in Table 22 W=H; X=CH₃; Y=H; V¹=2-Cl; V²=4-Cl.

Table 35: A and B are each as given in Table 22 W=H; X=CH₃; Y=CH₃; V¹=2-Cl; V²=4-Cl.

Table 36: A and B are each as given in Table 22 W=CH₃; X=CH₃; Z=CH₃; V¹=2-Cl; V¹=4-Cl.

Table 37: A and B are each as given in Table 22 W=H; X=CH₃; Y=H; V¹=4-CH₃; V²=H.

Table 38: A and B are each as given in Table 22 W=H; X=CH₃; Y=CH₃; V¹=4-CH₃; V²=H.

Table 39: A and B are each as given in Table 22 W=CH₃; X=CH₃; Y=CH₃; V¹=4-CH₃; V²=H.

Table 40: A and B are each as given in Table 22 W=H; X=CH₃; Y=H; V¹=4-OCH₃; V²=H.

Table 41: A and B are each as given in Table 22 W=H; X=CH₃; Y=CH₃; V¹=4-OCH₃; V²=H.

Table 42: A and B are each as given in Table 22 W=CH₃; X=CH₃; Y=CH₃; V¹=4-OCH₃; V²=H.

Using, in accordance with process (A), ethyl N-[(6-methyl-3-phenyl)-phenylacetyl]-1-amino-cyclohexane-carboxylate as starting material, the course of the process according to the invention can be represented by the following equation:

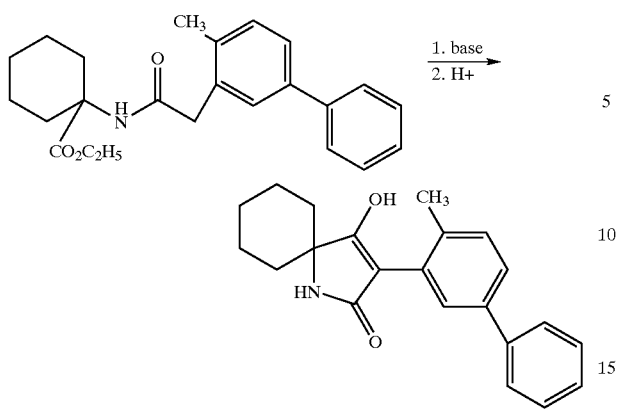

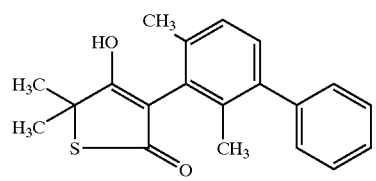

Using, for example in accordance with process (D-α), chlorocarbonyl 3-[(6-methyl-3-(4-methyl)-phenyl)-phenyl] ketene and 1,2-diazacyclopentane as starting materials, the course of the process according to the invention can be represented by the following equation:

Using, in accordance with process (B), ethyl (B) O-[(2-chloro-5-(4-chloro)-phenyl)-phenylacetyl]-2-hydroxyisobutyrate, the course of the process according to the invention can be represented by the following equation:

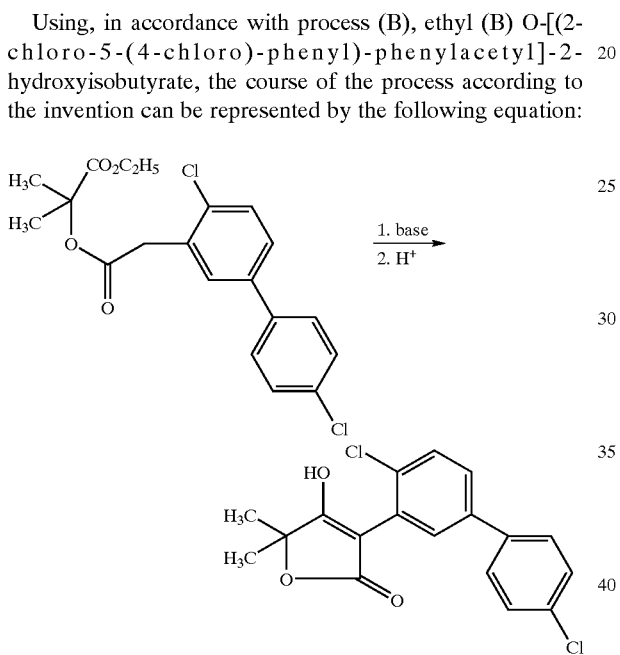

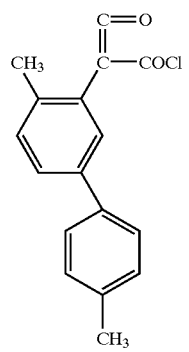

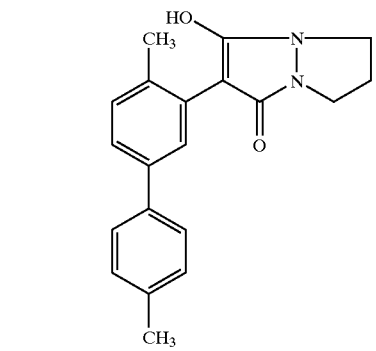

Using, in accordance with process (C), ethyl 2-[(2,6-dimethyl-3-phenyl)-phenyl]-4(4-methoxy)-benzylmercapto-4-methyl-3-oxo-valerate, the course of the process according to the invention can be represented by the following equation:

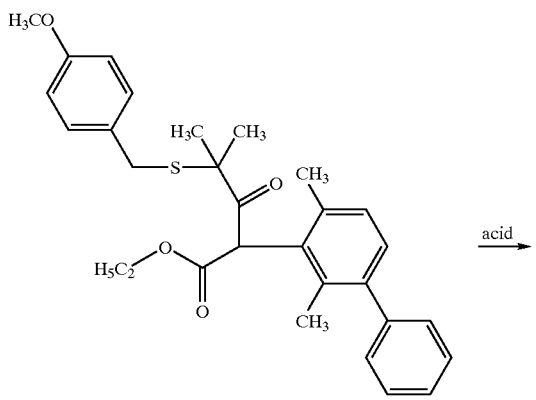

Using, for example in accordance with process (D-β), diethyl 3-[6-methyl-3-(3-chloro-phenyl)]-phenylmalonate and 1,2-diazacyclopentane as starting materials, the course of the process according to the invention can be represented by the followling equation:

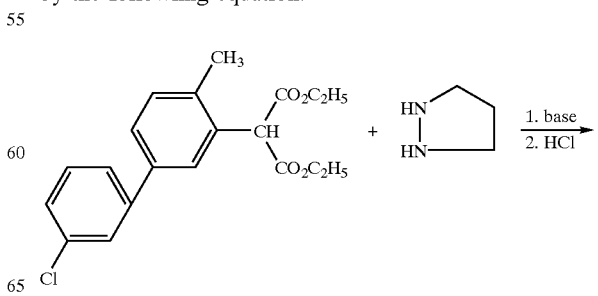

-continued

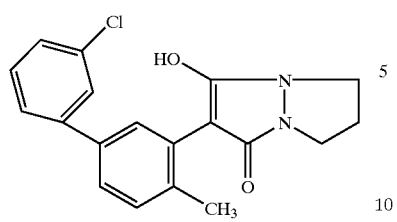

Using, for example in accordance with process (E), chlorocarbonyl 2-[(2,6-dimethyl-3-(4-trifluoromethoxyphenyl))-phenyl]ketene and acetone as starting materials, tie course of the process according to the invention can be represented by the following equation:

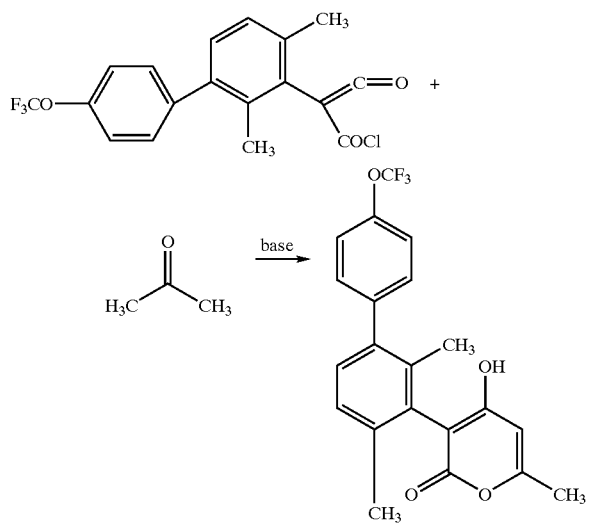

Using, for example in accordance with process (F), chlorocarbonyl 2-[(2,4,6-trimethyl-3-phenyl)-phenyl]ketene and thiobenzamide as starting materials, the course of the process according to the invention can be represented by the following equation:

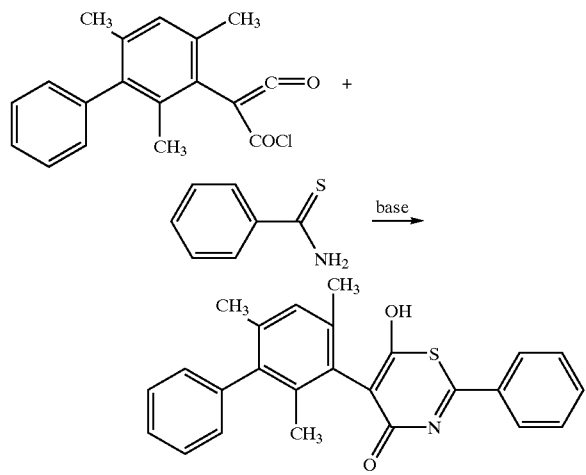

Using, in accordance with process (G), ethyl 5-[(6-methyl-3-phenyl)-phenyl]-2,3-tetramethylene-4-oxo-valerate, the course of the process according to the invention can be represented by the following equation:

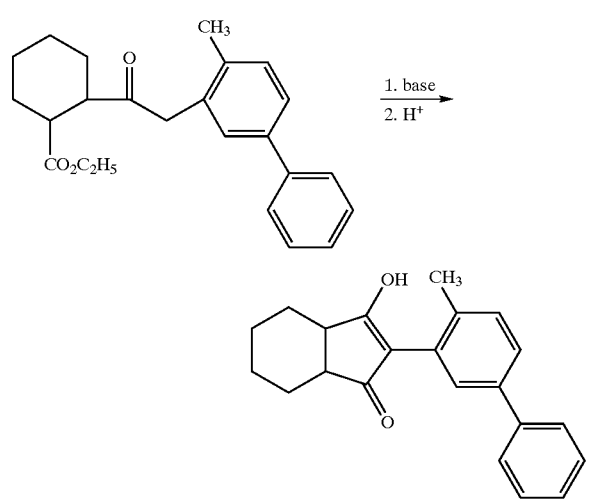

Using, in accordance with process (H), ethyl 5-[(2,4,6-trimethyl-3-phenyl)-phenyl]-2,2-dimethyl-5-oxo-hexanoate, the course of the process according to the invention can be represented by the following equation:

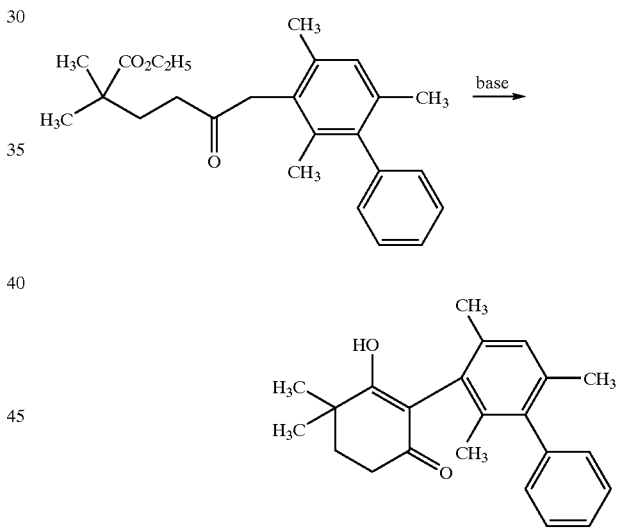

Using, in accordance with process (1), 3-[(2,6-dimethyl-3-bromo)-phenyl]-4,4-(penta-methylene)-pyrrolidine-2,4-dione and 4-chlorophenylboronic acid as starting materials, the course of the reaction can be represented by the following scheme:

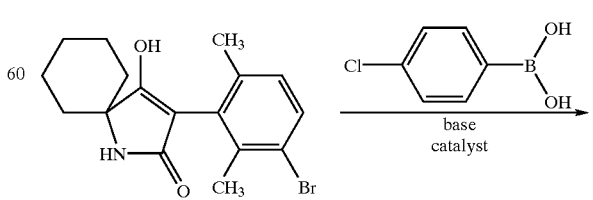

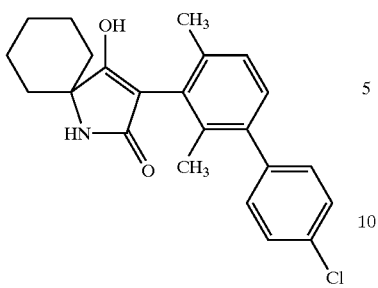

Using, in accordance with process (Jα), 3-[(2-chloro-5-(3-chlorophenyl))-phenyl]-5,5-dimethylpyrrolidine-2,4-dione and pivaloyl chloride as starting materials, the course of the process according to the invention can be represented by the following equation:

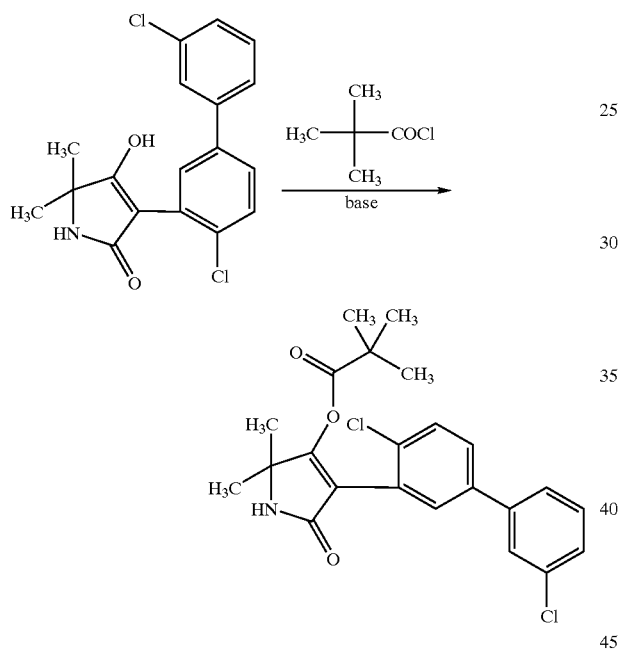

Using, in accordance with process (J), (variant β), 3-[(6-methyl-3-(4-methoxy-phenyl))-phenyl]-4-hydroxy-5-phenyl-$\Delta^3$-dihydrofuran-2-one and acetic anhydride as starting materials, the course of the process according to the invention can be represented by the following equation:

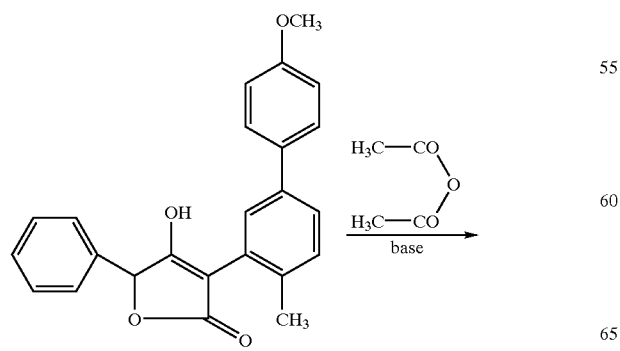

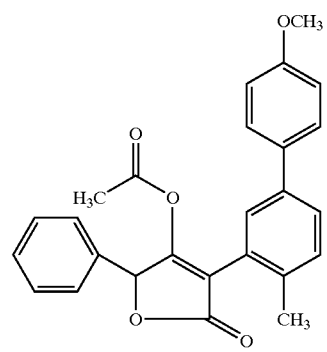

Using, in accordance with process (K), 8-[(2,6-dimethyl-3-phenyl)-phenyl]-1,6-diaza-bicyclo-(4.3.0$^{1.6}$)-nonane-7,9-dione and ethoxyethyl chloroformate as starting materials, the course of the process according to the invention can be represented by the following equation:

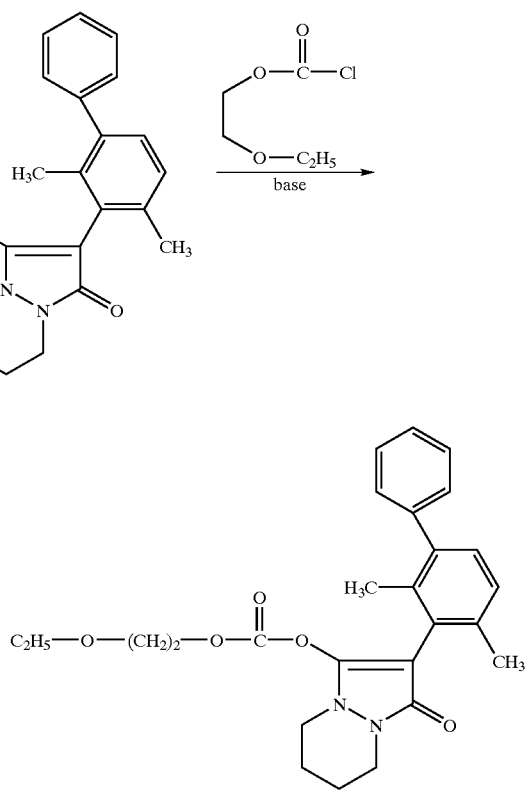

Using, in accordance with process (L), 3-[(2-chloro-5-(4-fluoro-phenyl))-phenyl]-4-hydroxy-5-methyl-6-(3-pyridyl)-pyrone and methyl chloromonothioformate as starting materials, the course of the reaction can be represented as follows:

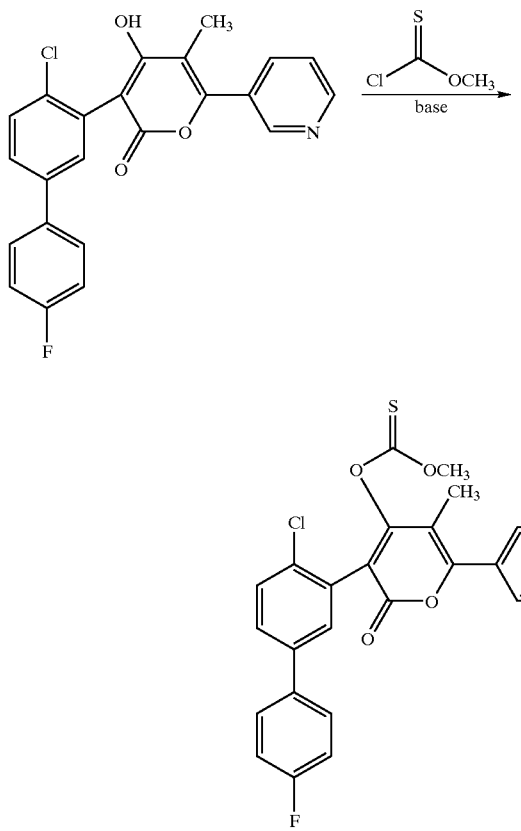

Using, in accordance with process (N), 2-[(6-methyl-3-phenyl)-phenyl]-4-hydroxy-5,5-dimethyl-$\Delta^3$-dihydrofuran-2-one and 2,2,2-trifluoroethyl methanethiophosphonyl chloride as starting materials, the course of the reaction can be represented by the following equation:

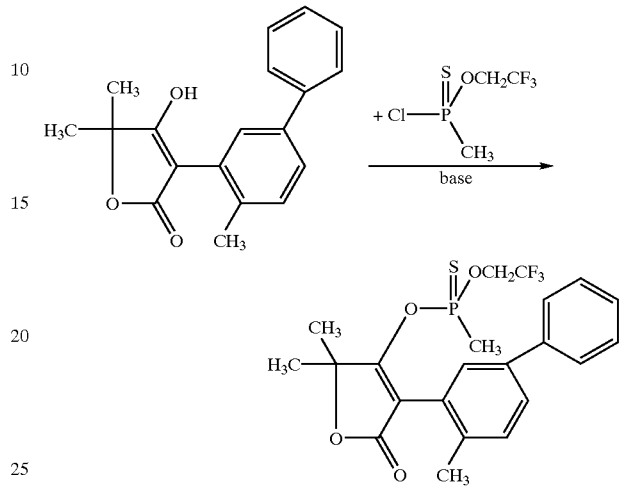

Using, in accordance with process (O), 3-[(2-trifluoromethyl-5-(4-trifluoromethyl-phenyl))-phenyl]-5-cyclopropyl-5-methyl-pyrrolidine-2,4-dione and NaOH as components, the course of the process according to the invention can be represented by the followling equation:

Using, in accordance with process (M), 2-[(2,4,6-trimethyl-3-(4-methyl-phenyl))-phenyl]-5,5-pentamethylene-pyrrolidine-2,4-dione and methanesulphonyl chloride as starting materials, the course of the reaction can be represented by the following equation:

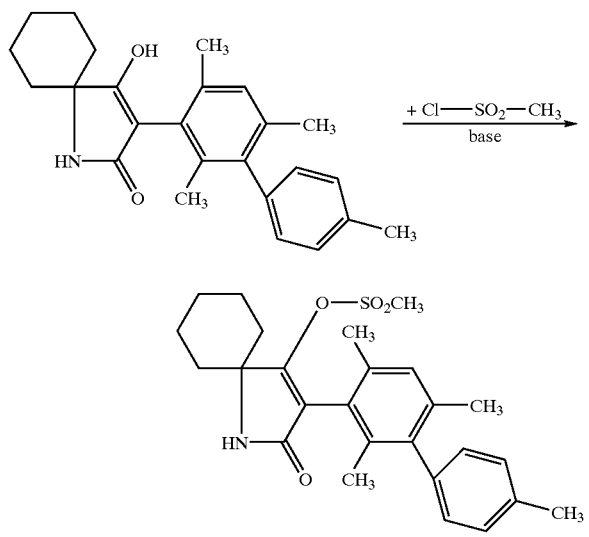

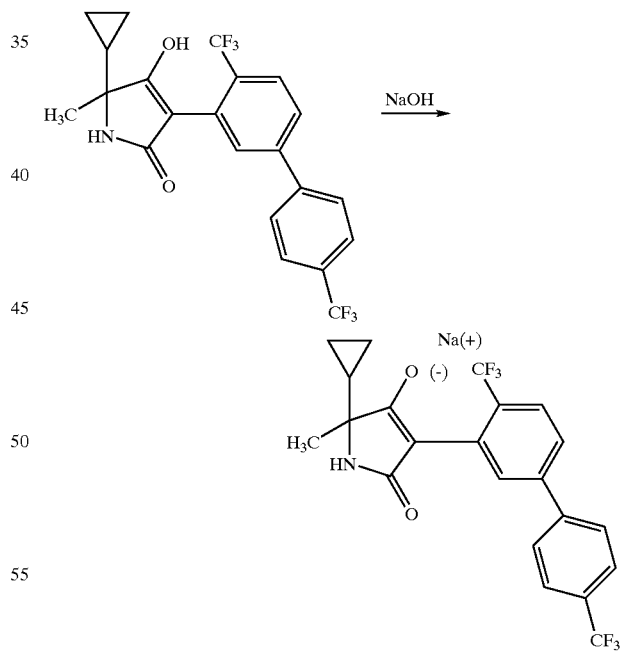

Using, in accordance with process (P) (variant α) 3-[(2-methyl-5-(3-trifluoromethyl-phenyl))-phenyl]-4-hydroxy-5-tetramethylene-$\Delta^3$-dihydro-furan-2-one and ethyl isocyanate as starting materials, the course of the reaction can be represented by the following equation:

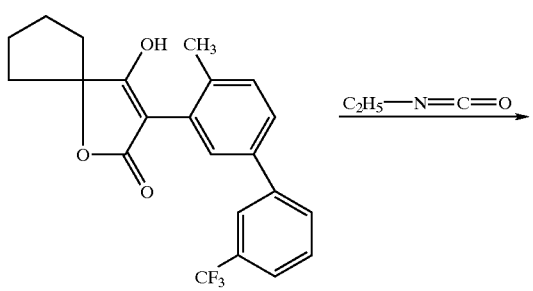
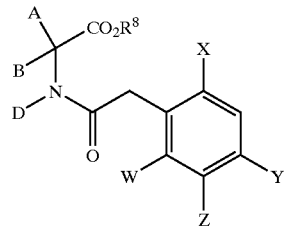

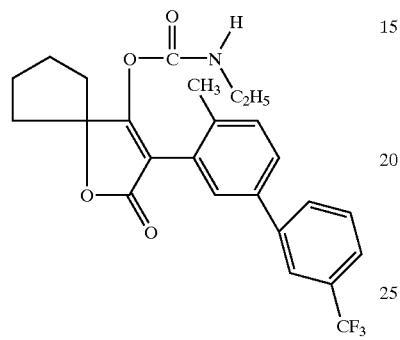

Using, in accordance with process (P) (variant β) 3-[(2-chloro-5-phenyl)-phenyl]-5-methyl-pyrrolidine-2,4-dione and dimethylcarbamoyl chloride as starting materials, the course of the reaction can be represented by the following scheme:

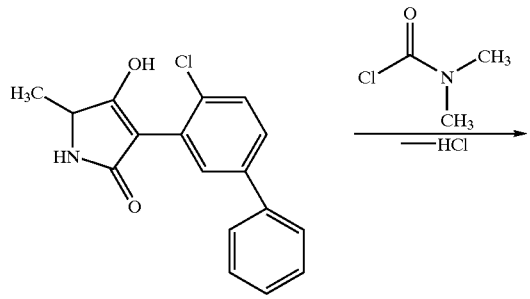

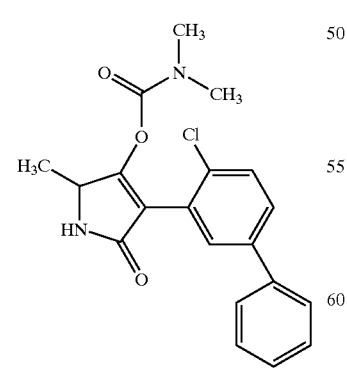

The compounds of the formula (II)

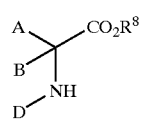

(II)

in which
A, B, D, W, X, Y, Z and $R^8$ are each as defined above which are required as starting materials in the process (a) according to the invention
are novel.

The acylamino acid esters of the formula (II) are obtained, for example, when amino acid derivatives of the formula (XXIII)

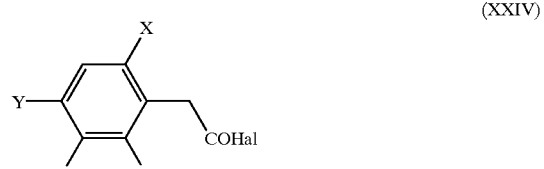

(XXIII)

in which
A, B, $R^8$ and D are each as defined above are acylated with substituted phenylacetyl halides of the formula (XXIV)

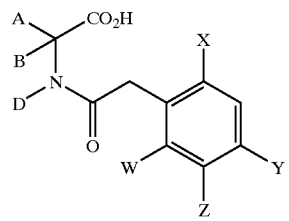

(XXIV)

in which
W, X, Y, and Z are each as defined above and
Hal represents chlorine or bromine
(Chem Reviews 52, 237–416 (1953); Bhattacharya, Indian J. Chem. 6 341–5, 1968)
or when acylamino acids of the formula (XXV)

(XXV)

in which

A, B, D, V, X, Y and Z are each as defined above are esterified (Chem. Ind. (London) 1568 (1968)).

The compounds of the formula (XXV)

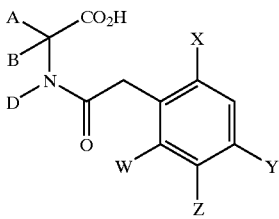
(XXV)

in which

A, B, D, W, X, Y and Z are each as defined above
are novel.

The compounds of the formula (XXV) are obtained when amino acids of the formula (XXVI)

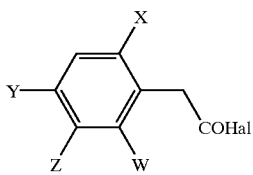
(XXVI)

in which

A, B and D are each as defined above are acylated with substituted phenylacetyl halides of the formula (XXIV)

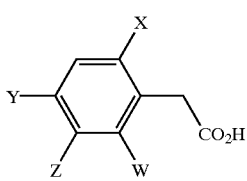
(XXIV)

in which

W, X, Y and Z are each as defined above and

Hal represents chlorine or bromine, for example according to Schotten-Baumann (Organikum, VEB Deutscher Verlag der Wissenschaften, Berlin 1977, p. 505).

The compounds of the formula (XXIV) are novel. They can be prepared by processes which are known in principle (see, for example, H. Henecka, Houben-Weyl, Methoden der Organischen Chemie, Vol. 8, p. 467–469 (1952)).

The compounds of the formula (XXIV) are obtained, for example, by reaching substituted phenylacetic acids of the formula (XXVII).

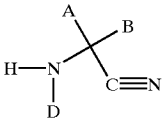
(XXVII)

in which

W, X, Y and Z are each as defined above with halogenating agents (for example thionyl chloride, thionyl bromide, oxalyl chloride, phosgene, phosphorus trichloride, phosphorus tribromide or phosphorus pentachloride), if appropriate in the presence of a diluent (for example optionally chlorinated aliphatic or aromatic hydrocarbons such as toluene or methylene chloride), at temperatures from −20° C. to 150° C., preferably from −10° C. to 100° C.

Some of the compounds of the formulae (XXIII) and (XXVI) are known, and/or they can be prepared by known processes (see, for example, Compagnon, Miocque Ann. Chim. (Paris) [14]5, p. 11–22, 23–27 (1970)).

The substituted cyclic aminocarboxylic acids of the formula (XXVIa) in which A and B form a ring are generally obtainable by the Bucherer-Bergs synthesis or by the Strecker synthesis and are in each case obtained in different isomer forns. Thus, under the conditions of the Bucherer-Bergs synthesis, the isomers (for simplicity called β below) in which the radicals R and the carboxyl group are equatorial are predominantly obtained, while under the conditions of the Strecker synthesis the isomers (for simplicity called α below) in which the amino group and the radicals R are equatorial are predominantly obtained.

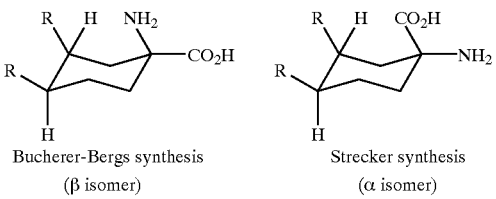

Bucherer-Bergs synthesis     Strecker synthesis (β isomer)     (α isomer)

(L. Munday, J. Chem. Soc. 4372 (1961); J. T. Eward, C. Jitrangeri, Can. J. Chem. 53, 3339(1975).

Furthermore, the starting materials of the formula (II)

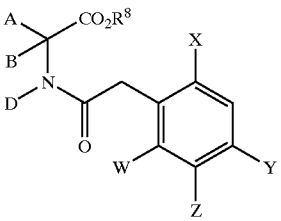
(II)

in which

A, B, D, W, X, Y, Z and $R^8$ are each as defined above used in the above process (A) can be prepared when aminonitriles of the formula (XXVIII)

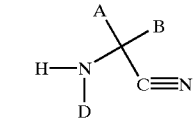
(XXVIII)

in which

A, B and D are each as defined above are reacted with substituted phenylacetyl halides of the formula (XXIV)

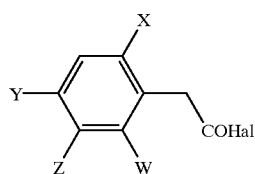

(XXIV)

in which

W, X, Y, Z and Hal are each as defined above to give compounds of the formula (XXIX)

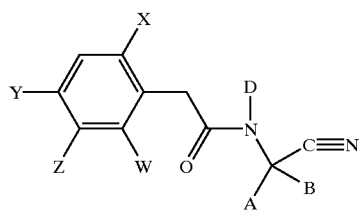

(XXIX)

in which

A, B, D, X, X, Y and Z are each as defined above and these are subsequently subjected to acidic alcoholysis.

The compounds of the formula (XXIX) are likewise novel.

The compounds of the formula (III)

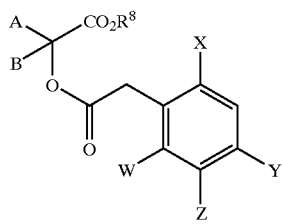

(III)

in which

A, B, W, X, Y, Z and $R^8$ are each as defined above required as starting materials in the process (B) according to the invention are novel.

They can be prepared by methods known in principle.

Thus, the compounds of the formula (III), for example, are obtained when 2-hydroxycarboxylic esters of the formula (XXX)

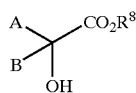

(XXX)

in which

A, B and $R^8$ are each as defined above are acylated with substituted phenylacetyl halides of the formula (XXIV)

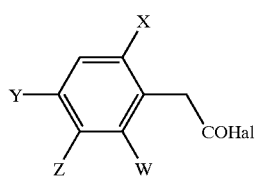

(XXIV)

in which

W, X, Y, Z and Hal are each as defined above (Chem. Reviews 52, 237–416 (1953) and the applications intially cited).

Furthermore, compounds of the formula (III) are obtained when substituted phenylacetic acids of the formula (XXVII)

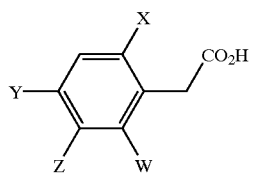

(XXVII)

in which

W, X, Y and Z are each as defined above are alkylated with α-halogenocarboxylic esters of the formula (XXXI)

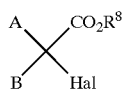

(XXXI)

in which

A, B and $R^8$ are each as defined above and

Hal represents chlorine or bromine.

The compounds of the formula (XXVII) are novel.

The compounds of the formula (XXXI) are commercially available.

The compounds of the formula (XXVII)

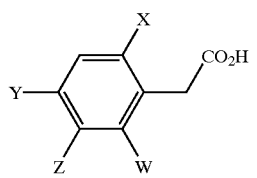

(XXVII)

in which

W, X, Y and Z are each as defined above are obtained, for example,

α) when compounds of the formula (XXVII-a)

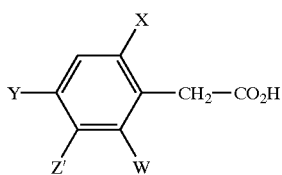
(XXVII-a)

in which
X and Y are each as defined above
Z' represents chlorine or bromine, preferably represents bromine,
are reacted with boronic acids of the formula (XII)

(XII)

in which
Z is as defined above
in the presence of a solvent, a base and a catalyst (preferably a palladium complex, such as, for example, tetrakis (triphenylphosphine)-palladium)
or
β) when phenylacetic esters of the formula (XXXII)

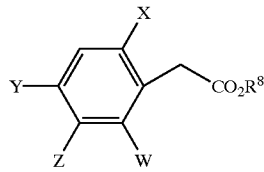
(XXXII)

in which
W, X, Y, Z and $R^8$ are each as defined above
are hydrolysed under generally known standard conditions in the presence of acids or bases, in the presence of a solvent, or
γ) when phenylacetic acids of the formula (XXVII-b)

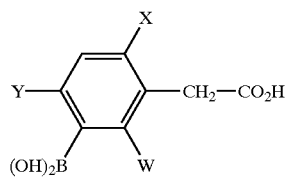
(XXVII-b)

in which
W, X and Z are each as defined above
are reacted with halogen compounds of the formula (XXXIII), Z—Hal    (XXXIII)

in which
Z is as defined above and
Hal represents chlorine, bromine or iodine, preferably bromine and iodine,
in the presence of a solvent, a base and a catalyst (preferably one of the abovementioned palladium complexes).

Some of the compounds of the formulae (XII) and (XXXIII) are known, some of them are commercially available, or they can be prepared by processes known in principle. Some of the phenylacetic acids of the formula (XXVII-a) are known from WO 97/01535, WO 97/36 868 and WO 98/05 638, or they can be prepared by the processes described therein.

The compounds of the formulae (XXVII-b) and (XXXII) are novel.

The compounds of the formula (XXVII-b)

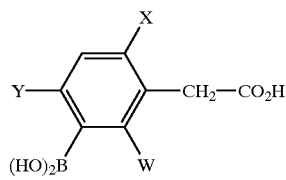
(XXVII-b)

in which
W, X and Y are each as defined above
are obtained, for example, when phenylacetic acids of the formula (XXVII-a)

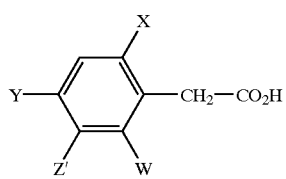
(XXVII-a)

in which
W, X, Y and Z' are each as defined above
are reacted with lithium compounds of the formula (XXXIV)

Li—$R^{21}$    (XXXIV)

in which
$R^{21}$ represents $C_1$–$C_8$-alkyl or phenyl, preferably represents n-$C_4H_9$,
and boronic esters of the formula (XXXV)

$B(OR^8)_3$    (XXXV)

in which
$R^8$ is as defined above
in the presence of a diluent.
The compounds of the formulae (XXXIV) and (XXXV) are commercially available compounds.
The compounds of the formula (XXXII)

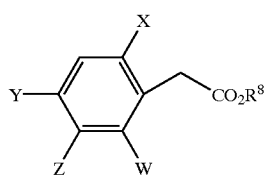
(XXXII)

in which
W, X, Y, Z and $R^8$ are each as defined above
are obtained, for example, when phenylacetic esters of the formula (XXXII-a)

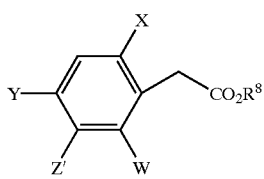
(XXXII-a)

in which

R⁸, W, Y and Z' are each as defined above are reacted with boronic acids of the formula (XII)

(XII)

in which

Z is as defined above in the presence of a solvent, a base and a catalyst (preferably one of the abovementioned palladium complexes).

Some of the phenylacetic esters of the formula (XXXII-a) are known from the applications WO 97/01535, WO 97/36868 and WO 98/0563, or they can be prepared by the processes described therein.

The compounds of the formula (IV)

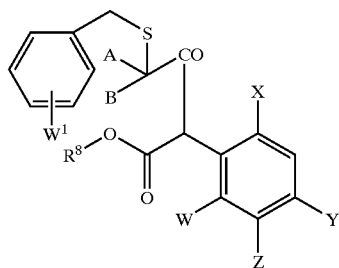
(IV)

in which

A, B, W, W¹, X, Y, Z and R⁸ are each as defined above
required as starting materials in the above process (C) are novel.

They can be prepared by methods known in principle.

The compounds of the formula (IV) are obtained, for example, when substituted phenylacetic esters of the formula (XXXII)

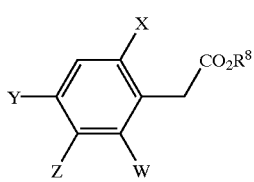
(XXXII)

in which

W, X, Y, R⁸ and Z are each as defined above
are acylated with 2-benzylthio-carbonyl halides of the formula (XXXVI)

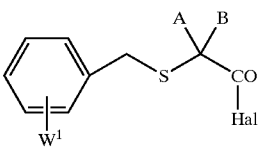
(XXXVI)

in which

A, B and W¹ are each as defined above and

Hal represents halogen (in particular chlorine or bromine)

in the presence of strong bases (see, for example, M. S. Chambers, E. J. Thomas, D. J. Williams, J. Chem. Soc. Chem. Commun., (1987), 1228).

The compounds of the formula (XXXII) are novel. Compounds of the formula (XXXII) are also obtained when compounds of the formula (XXVII)

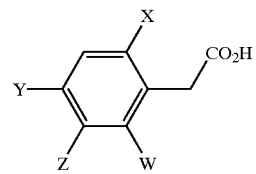
(XXVII)

in which

W, X, Y and Z are each as defined above are esterified in the presence of alcohols and dehydrating agents (for example conc. sulphuric acid), or when alcohols are acylated with compounds of the formula (XXIV)

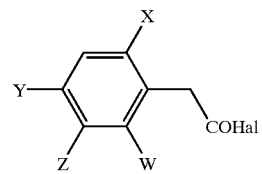
(XXVI)

in which

W, X, Y, Z and Hal are each as defined above (Chem. Reviews 52, 237–416 (1953)).

Some of the benzylthio-carbonyl halides of the formula (XXXVI) are known and/or they can be prepared by known processes (J. Antibiotics (1983), 26, 1589).

The halogenocarbonyl ketenes of the formula (V) required as starting materials in the above processes (D), (E) and (F) are novel. They can be prepared by methods which are known in principle (cf., for example, Org. Prep. Proced. Int., 7, (4), 155–158, 1975 and DE 1 945 703). Thus, for example, the compounds of the formula (V)

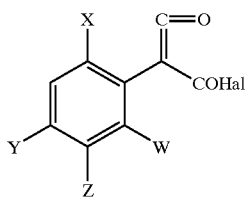

(V)

in which

W, X, Y and Z are each as defined above and

Hal represents chlorine or bromine are obtained when substituted phenylmalonic acids of the formula (XXXVII)

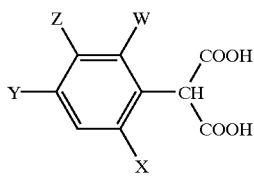

(XXXVII)

in which

W, X, Y and Z are each as defined above are reacted with acyl halides, such as, for example, thionyl chloride, phosphorus(V) chloride, phosphorus(III) chloride, oxalyl chloride, phosgene or thionyl bromide, if appropriate in the presence of catalysts, such as, for example, dimethylformamide, methyl-steryl-formamide or triphenylphosphine and if appropriate in the presence of bases such as, for example, pyridine or triethylamine.

The substituted phenylmalonic acids of the formula (XXXVII) are novel. They can be prepared by known processes in a simple manner (cf., for example, Organikum, VEB Deutscher Verlag der Wissenschaften, Berlin 1977, p. 517 ff, EP-A-528 156, WO 97/36868, WO 97/01535 and WO 98/05638).

Thus, phenylmalonic acids of the formula (XXXVII)

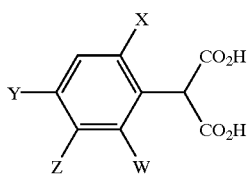

(XXXVII)

in which

W, X, Y and Z are each as defined above are obtained when phenylmalonic esters of the formula (VI)

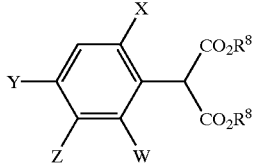

(VI)

in which

W, X, Y, Z and $R^8$ are each as defined above are intially hydrolysed in the presence of a base and in a solvent and subsequently carefully acidified (EP-528 156, WO 96/36868, WO 97/01535).

The malonic esters of the formula (VI)

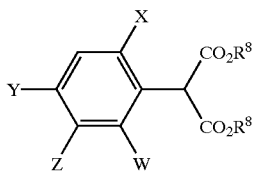

(VI)

in which

W, X, Y, Z and $R^8$ are each as defined above are novel.

They can be prepared by generally known methods of organic chemistry (cf., for example, Tetrahedron Lett. 27, 2763 (1986) and Organikum, VEB Deutscher Verlag der Wissenschaften, Berlin 1977, p. 587 ff.).

Some of the hydrazines of the formula (VII)

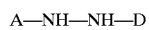

A—NH—NH—D       (VII), in which

A and D are each as defined above required as starting materials for the process (D) according to the invention are known, and/or they can be prepared by methods known from the literature (cf., for example, Liebigs Ann. Chem. 585, 6 (1954); Reaktionen der organischeni Synthese, C. Ferri, p. 212, 513; Georg Thieme Verlag Stuttgart, 1978; Liebigs Ann. Clem. 443, 242 (1925); Chem. Ber. 98, 2551 (1965), EP-508 126).

The carbonyl compounds of the formula (VIII)

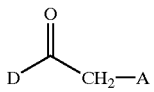

(VIII)

in which

A and D are each as defined above or their silyl enol ethers of the formula (VIIIa)

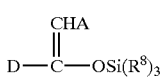

(VIIIa)

in which

A, D and $R^8$ are each as defined above required as starting materials for the process (E) according to the invention are commercially available, generally known compounds or compounds which are obtainable by known processes.

The preparation of the ketene acid chlorides of the formula (V), required as starting materials for carrying out the process (F) according to the invention has already been described above. The thioamides of the formula (IX)

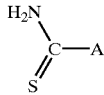

(IX)

in which
A is as defined above
required for carrying out the process (F) according to the invention are compounds which are generally known in organic chemistry.

The compounds of the formula (X)

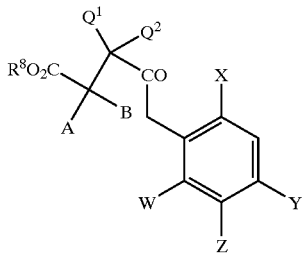

(X)

in which
A, B, $Q^1$, $Q^2$, W, X, Y, Z and $R^8$ are each as defined above
required as starting materials in the above process (G) are novel.

They can be prepared by methods known in principle.

The compounds of the formula (X) are obtained, for example, when compounds of the formula (XXXVIII)

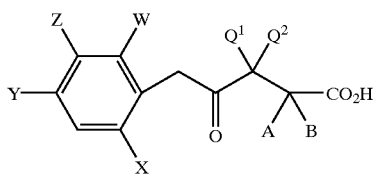

(XXXVIII)

in which
W, X, Y, Z, A, B, $Q^1$ and $Q^2$ are each as defined above
are esterified (cf., for example, Organikurh, 15th edition, Berlin, 1977, page 499) or alkylated (see Preparation Example).

The compounds of the formula (XXXVIII)

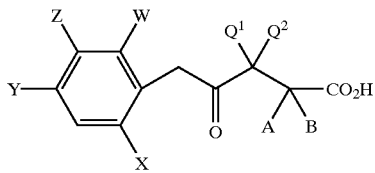

(XXXVIII)

in which
A, B, $Q^1$, $Q^2$, W, X, Y and Z are each as defined above are novel but can be prepared by methods known in principle (see Preparation Example).

The 5-aryl-4-ketocarboxylic acids of the formula (XXXVIII) are obtained, for example, when 2-phenyl-3-oxo-adipic esters of the formula (XXXIX)

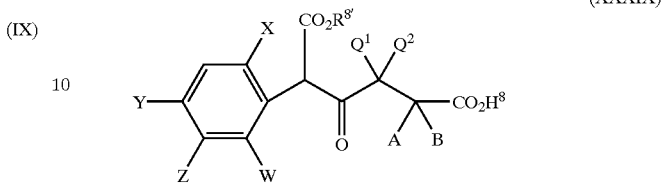

(XXXIX)

in which
A, B, $D^1$, $D^2$, W, X, Y and Z are each as defined above and $R^8$ and $R^{8'}$ each represent alkyl (in particular $C_1$–$C_8$-alkyl)
are decarboxylated, if appropriate in the presence of a diluent and if appropriate in the presence of a base or acid (cf., for example, Organikum, 15th edition, Berlin, 1977, pages 519 to 521).

The compounds of the formula (XXXIX)

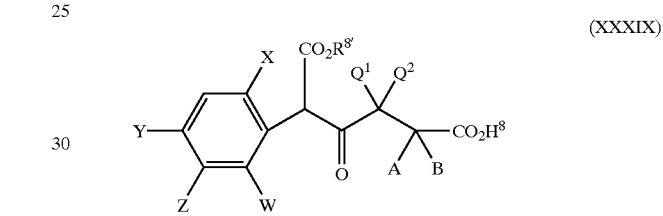

(XXXIX)

in which
A, B, $Q^1$, $Q^2$, W, X, Y, Z, $R^8$, $R^{8'}$ are each as defined above
are novel.

The compounds of the formula (XXXIX) are obtained, for example,
when dicarboxylic monoester chlorides of the formula (XL),

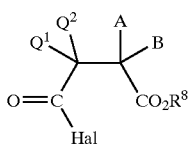

(XL)

in which
A, B, $Q^1$, $Q^2$ and $R^8$ are each as defined above and
Hal represents chlorine or bromine
or carboxylic anhydrides of the formula (XLI-A)

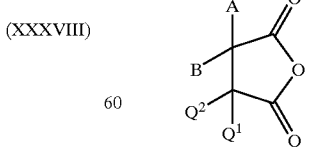

(XLI-A)

in which
A, B, $Q^1$ and $Q^2$ are each as defined above
are acylated with a phenyl acetic ester of the formula (XXXII)

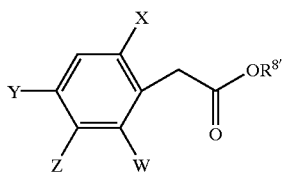
(XXXII)

in which

W, X, Y, Z and $R^{8'}$ are each as defined above in the presence of a diluent and in the presence of a base (cf., for example, M. S. Chambers, E. J. Thomas, D. J. Winiams, J. Chem. Soc. Chem. Commun., (1987), 1228, cf. also the Preparation Examples).

Some of the compounds of the formulae (XL) and (XLI-A) are known or commercially available compounds of organic chemistry, and/or they can be prepared in a simple manner by methods known in principle.

The compounds of the formula (XI)

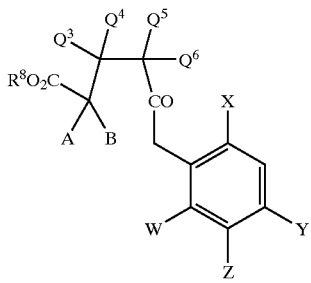
(XI)

in which

A, B, $Q^3$, $Q^4$, $Q^5$, $Q^6$, W, X, Y, Z and $R^8$ are each as defined above required as starting materials in the above process (H) are novel.

They can be prepared by methods known in principle.

The 6-aryl-5-ketocarboxylic esters of the formula (XI) are obtained, for example, when 6-aryl-5-ketocarboxylic acids of the formula (XLII)

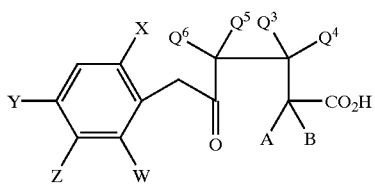
(XLII)

in which

A, B, $Q^3$, $Q^4$, $Q^5$, $Q^6$, W, X, Y and Z are each as defined above are esterified (cf., for example, Organikum, 15th edition, Berlin, 1977, page 499).

The compounds of the formula (XLII)

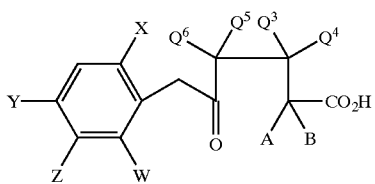
(XLII)

in which

A, B, $Q^3$, $Q^4$, $Q^5$, $Q^6$, V, X, Y and Z are each as defined above are novel. They can be prepared by methods known in principle, for example by hydrolysing and decarboxylating substituted 2-phenyl-3-oxo-heptanedioic esters of the formula (XLIII)

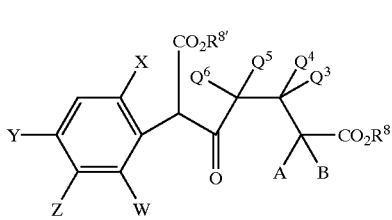
(XLIII)

in which

A, B, $Q^3$, $Q^4$, $Q^5$, $Q^6$, W, X, Y and Z are each as defined above and $R^8$ and $R^{8'}$ each represent alkyl (preferably $C_1$–$C_6$-alkyl), if appropriate in the presence of a diluent and if appropriate in the presence of a base or acid (cf., for example, Organikum, 15th edition, Berlin, 1977, page 519 to 521) (see also Preparation Example).

The compounds of the formula (XLIII)

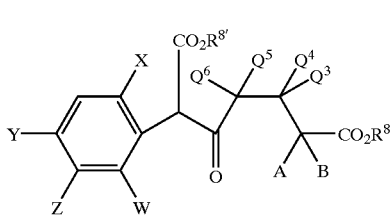
(XLIII)

in which

A, B, $Q^3$, $Q^4$, $Q^5$, $Q^6$, W, X, Y, Z, $R^8$ and $R^8$ are each as defined above are novel. They can be obtained, for example, when dicarboxylic esters of the formula (XLIV),

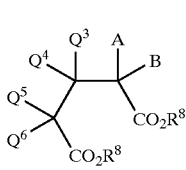
(XLIV)

in which

A, B, $Q^3$, $Q^4$, $Q^5$, $Q^6$ and $R^8$ are each as defined above are condensed with a substituted phenylacetic ester of the formula (XXXII)

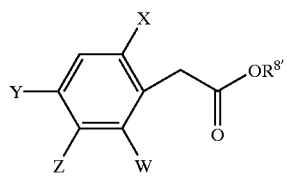

(XXXII)

in which

W, X, Y, Z und R$^{8'}$ are each as defined above in the presence of a diluent and in the presence of a base (see also preparation example).

Some of the compounds of the formula (XLIV) are known, and/or they can be prepared by known processes.

Instead of the compounds of the formula (XLIV), it is also possible to employ the corresponding anhydrides. The reaction is then carried out as in the preparation of the compounds of the formula (X), where anhydrides of the formula (XLI-B) are employed as starting materials. Some compounds of the formula (XLI-B) are known, or commercially available, compounds.

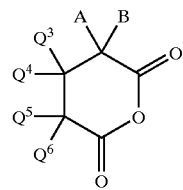

(XLI-B)

The compounds of the formula (XXCXII) have already been described under the precursors for the process (B).

Compounds of the formula (XXXII) are also obtained, for example, by reacting substituted 1,1,1-trichloro-2-phenylethanes of the formula (XLV)

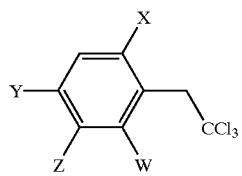

(XLV)

in which

W, X, Y and Z are each as defined above initially with alkoxides (for example alkali metal alkoxides such as sodium methoxide or sodium ethoxide) in the presence of a diluent (for example the alcohol derived from the alkoxide) at temperatures between 0° C. and 150° C., preferably between 20° C. and 120° C., and subsequently with an acid (preferably an inorganic acid such as, for example, sulphuric acid) at temperatures between –20° C. and 150° C., preferably between 0° C. and 100° C. (cf. DE 3 314 249).

The compounds of the formula (XLV) are novel; they can be prepared by processes known in principle.

The compounds of the formula (XLV) are obtained, for example, when anilines of the formula (XLVI)

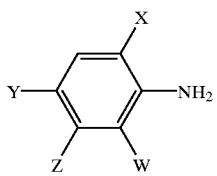

(XLVI)

in which

W, X, Y and Z are each as defined above are reacted with vinylidene chloride (CH$_2$=CCl$_2$) in the presence of an alkyl nitrite of the formula (XLVII)

$$R^{21}\text{—ONO} \quad\quad\quad\quad (XLVII)$$

in which

R$^{21}$ represents alkyl, preferably C$_1$–C$_6$-alkyl, in the presence of copper(II) chloride and, if appropriate, in the presence of a diluent (for example an aliphatic nitrile such as acetonitrile), at a temperature of from –20° C. to 80° C., preferably from 0° C. to 60° C.

The compounds of the formula (XLVII) are known compounds of organic chemistry. Copper(II) chloride and vinylidene chloride have been known for a long time and are commercially available.

Some of the anilines of the formula (XLVI) are novel.

The anilines of the formula (XLVI) are obtained, for example, when anilines of the formula (XLVI-a)

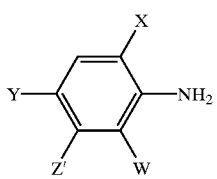

(XLVI-a)

in which

W, X and Y are each as defined above and

Z' represents chlorine or bromine, preferably bromine, are reacted with boronic acids of the formula (XII)

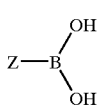

(XII)

in which

Z is as defined above in the presence of a solvent, a base and a catalyst (preferably a palladium complex, such as, for example, tetrakis(triphenylphosphine)palladium.

The anilines of the formula (XLVI-a) are known compounds, or they can generally be prepared by known methods.

Some of the compounds of the formulae (I-1'-a) to (I-8'-a) in which A, B, D, Q$^1$, Q$^2$, Q$^3$, Q$^4$, Q$^5$, Q$^6$, W, X and Y are each as defined above and Z' represents chlorine and bromine, preferably represents bromine, and which are required as starting materials in the above process (1) are known (WO 96/35 664, WO 97/02 243 and WO 98/05 638) or they can be prepared by the processes described therein or by processes (A) to (H).

Some of the boronic acids of the formula (XII)

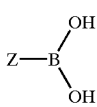
(XII)

in which
Z is as defined above
are commercially available, or they can be prepared in a simple manner by generally known processes.

The acyl halides of the formula (XIII), carboxylic anhydrides of the formula (XIV), chloroformic esters or chloroformic thioesters of the formula (XV), chloromonothioformic esters or chlorodithioformic esters of the formula (XVI), sulphonyl chlorides of the formula (XVII), phosphorus compounds of the formula (XVIII) and metal hydroxides, metal alkoxides or amines of the formulae (XIX) and (XX) and isocyanates of the formula (XXI) and carbamoyl chlorides of the formula (XXII) furthermore required as starting materials for carrying out the processes (J), (K), (L), (M), (N), (O) and (P) according to the invention are generally known compounds of organic or inorganic chemistry.

Moreover, the compounds of the formulae (VII), (VIII), (IX), (XIII) to (XXIII), (XXVI), (XXVIII), (XXX), (XXXVI), (XL), (XLI) and (XLVI) are known from the patent applications cited at the outset, and/or they can be prepared by the methods given therein.

The process (A) is characterized in that compounds of the formula (II) in which A, B, D, W, X, Y, Z and $R^8$ are each as defined above are subjected to an intramolecular condensation in the presence of a base.

Suitable diluents for the process (A) according to the invention are all inert organic solvents. Preference is given to using hydrocarbons, such as toluene and xylene, furthermore ethers, such as dibutyl ether, tetrahydrofuran, dioxane, glycol dimethyl ether and diglycol dimethyl ether, moreover polar solvents, such as dimethyl sulphoxide, sulpholane, dimethylformamide and N-methyl-pyrrolidone, and also alcohols, such as methanol, ethanol, propanol, iso-propanol, butanol, iso-butanol and tert-butanol.

Suitable bases (deprotonating agents) for carrying out the process (A) according to the invention are all customary proton acceptors. Preference is given to using alkali metal and alkaline earth metal oxides, hydroxides and carbonates, such as sodium hydroxide, potassium hydroxide, magnesium oxide, calcium oxide, sodium carbonate, potassium carbonate and calcium carbonate, which can also be employed in the presence of phase-transfer catalysts, such as, for example, triethylbenzylammonium chloride, tetrabutylammonium bromide, Ado,en 464 (=methyltrialkyl $(C_8-C_{10})$ammonium chloride) or TDA 1 (=tris (methoxyethoxyethyl)-amine). Alkali metals such as sodium and potassium can also be used. Furthermore, alkali metal and alkaline earth metal amides and hydrides, such as sodium amide, sodium hydride and calcium hydride, and additionally also alkali metal alkoxides, such as sodium methoxide, sodium ethoxide and potassium tert-butoxide can be employed.

When carrying out the process (A) according to the invention, the reaction temperatures can be varied within a relatively wide range. In general, the reaction is carried out at temperatures between 0° C. and 250° C., preferably between 50° C. and 150° C.

The process (A) according to the invention is generally carried out under atmospheric pressure.

When carrying out the process (A) according to the invention, the reaction components of the formula (II) and the deprotonating bases are generally employed in approximately double-equimolar amounts. However, it is also possible to use a larger excess (up to 3 mol) of one component or the other.

The process (B) is characterized in that compounds of the formula (III) in which A, B, W, X, Y, Z and $R^8$ are each as defined above are subjected to an intramolecular condensation in the presence of a diluent and in the presence of a base.

Suitable diluents for the process (B) according to the invention are all inert organic solvents. Preference is given to using hydrocarbons, such as toluene and xylene, furthermore ethers, such as dibutyl ether, tetrahydrofuran, dioxane, glycol dimethyl ether and diglycol dimethyl ether, moreover polar solvents, such as dimethyl sulphoxide, sulpholane, dimethylformamide and N-methyl-pyrrolidone, and also alcohols, such as methanol, ethanol, propanol, iso-propanol, butanol, iso-butanol and tert-butanol.

Suitable bases (deprotonating agents) for carrying out the process (B) according to the invention are all customary proton acceptors. Preference is given to using alkali metal and alkaline earth metal oxides, hydroxides and carbonates, such as sodium hydroxide, potassium hydroxide, magnesium oxide, calcium oxide, sodium carbonate, potassium carbonate and calcium carbonate, which can also be employed in the presence of phase-transfer catalysts, such as, for example, triethylbenzylammonium chloride, tetrabutylammonium bromide, Adogen 464 (=methyltrialkyl $(C_8-C_{10})$ammonium chloride) or TDA 1 (=tris (methoxyethoxyethyl)-amine). Alkali metals such as sodium and potassium can also be used. Furthermore, alkali metal and alkaline earth metal amides and hydrides, such as sodium amide, sodium hydride and calcium hydride, and additionally also alkali metal alkoxides, such as sodium methoxide, sodium ethoxide and potassium tert-butoxide, can be employed.

When carrying out the process (B) according to the invention, the reaction temperatures can be varied within a relatively wide range. In general, the reaction is carried out at temperatures between 0° C. and 250° C., preferably between 50° C. and 150° C.

The process (B) according to the invention is generally carried out under atmospheric pressure.

When carrying out the process (B) according to the invention, the reaction components of the formula (III) and the deprotonating bases are generally employed in approximately equimolar amounts. However, it is also possible to use a relatively large excess (up to 3 mol) of one component or the other.

The process (C) is characterized in that compounds of the formula (IV) in which A, B, W, X, Y, Z and $R^8$ are each as defined above are cyclized intramolecularly in the presence of an acid and, if appropriate, in the presence of a diluent.

Suitable diluents for the process (C) according to the invention are all inert organic solvents. Preference is given to using hydrocarbons, such as toluene and xylene, furthermore halogenated hydrocarbons such as dichloromethane, chloroform, ethylene chloride, chlorobenzene, dichlorobenzene, moreover polar solvents, such as dimethyl sulphoxide, sulpholane, dimethyl formamide and N-methyl-pyrrolidone. Furthermore, it is possible to employ alcohols such as methanol, ethanol, propanol, iso-propanol, butanol, isobutanol, tert-butanol.

If appropriate, the acid used can also serve as diluent.

Suitable acids for the process (C) according to the invention are all customary inorganic and organic acids, such as, for example, hydrohalic acids, sulphuric acid, alkyl, aryl and haloalkylsulphonic acids, in particular halogenated alkylcarboxylic acids, such as, for example, trifluoroacetic acid.

When carrying out the process (C) according to the invention, the reaction temperatures can be varied within a relatively wide range. In general, the reaction is carried out at temperatures between 0° C. and 250° C., preferably between 50° C. and 150° C.

The process (C) according to the invention is generally carried out under atmospheric pressure.

When carrying out the process (C) according to the invention, the reaction components of the formula (IV) and the acid are employed, for example, in equimolar amounts. However, it is also possible, if appropriate, to use the acid as solvent or as catalyst.

The processes (D-α) and (D-β) are characterized in that compounds of the formula (V) or (VI) in which W, X, Y, Z, $R^8$ and Hal are each as defined above are reacted with compounds of the formula (VII) in which A and D are each as defined above, if appropriate in the presence of a base and if appropriate in the presence of a diluent.

Suitable diluents for the processes (D-α) and (D-β) according to the invention are all inert organic solvents. Preference is given to using hydrocarbons, such as toluene and xylene, furthermore ethers, such as dibutyl ether, tetrahydrofuran, dioxane, glycol dimethyl ether and diglycol dimethyl ether, moreover polar solvents, such as dimethyl sulphoxide, sulpholane, dimethylformamide and N-methyl-pyrrolidone, and also, only in the case where compounds of the formula (VI) are employed, alcohols such as methanol, ethanol, propanol, iso-propanol, butanol, iso-butanol and tert-butanol.

When compounds of the formula (V) are employed, suitable bases are inorganic bases, in particular alkali metal or alkaline earth metal carbonates such as sodium carbonate, potassium carbonate or calcium carbonate, and also organic bases, such as, for example, pyridine or triethylamine, and when compounds of the formula (VI) are employed, alkali metal and alkaline earth metal oxides, hydroxides and carbonates, such as sodium hydroxide, potassium hydroxide, magnesium hydroxide, calcium oxide, sodium carbonate, potassium carbonate and calcium carbonate, which can also be employed in the presence of phase-transfer catalysts, such as, for example, triethylbenzylammonium chloride, tetrabutylammonium bromide, Adogen 464 (=methyltrialkyl ($C_8$–$C_{10}$)-ammonium chloride) or TDA 1 (=tris (methoxyethoxyethyl)-amine), furthermore alkali metals, such as sodium or potassium, alkali metal amides and hydrides and alkaline earth metal amides and hydrides, such as sodium amide, sodium hydride and calcium hydride, and additionally alkali metal alkoxides, such as sodium methoxide and potassium tert-butoxide.

When carrying out the processes (D-α) and (D-β) according to the invention, the reaction temperatures can be varied within a relatively wide range. In general, the reaction is carried out at temperatures between −20° C. and 250° C., preferably between 0° C. and 150° C.

The processes (D-α) and (D-β) according to the invention are generally carried out under atmospheric pressure.

When carrying out the processes (D-α) and (D-β) according to the invention, the reaction components of the formulae (V) and (VII) or (VI) and (VII) and the deprotonating bases which are employed if appropriate are generally employed in approximately equimolar amounts. However, it is also possible to use a relatively large excess (up to 3 mol) of one component or the other.

The process (E) according to the invention is characterized in that carbonyl compounds of the formula (VIII) or enol ethers thereof of the formula (VIII-a) are reacted with ketene acid halides of the formula (V) in the presence of a diluent and, if appropriate, in the presence of an acid acceptor.

Suitable diluents for the process (E) according to the invention are all inert organic solvents. Preference is given to using hydrocarbons, such as toluene and xylene, furthermore ethers, such as dibutyl ether, glycol dimethyl ether and diglycol dimethyl ether, moreover polar solvents, such as dimethyl sulphoxide, sulpholane, dimethylformamide or N-methyl-pyrrolidone.

Suitable acid acceptors for carrying out the process variant E) according to the invention are all customary acid acceptors.

Preference is given to using tertiary amines, such as triethylamine, pyridine, diazabicyclooctane (DABCO), diazabicycloundecane (DBU), diazabicyclononene (DBN), Hüing base and N,N-dimethyl-aniline.

When carrying out the process variant E) according to the invention, the reaction temperatures can be varied within a relatively wide range. Advantageously, the reaction is carried out at temperatures between 0° C. and 250° C., preferably between 50° C. and 220° C.

The process (E) according to the invention is advantageously carried out under atmospheric pressure.

When carrying out the process (E) according to the invention, the reaction components of the formulae (VIII) and (V) in which A, D, W, X, Y and Z are each as defined above and Hal represents halogen, and, if appropriate, the acid acceptors, are generally employed in approximately equimolar amounts. However, it is also possible to use a relatively large excess (up to 5 mol) of one component or the other.

The process (F) according to the invention is characterized in that thioamides of the formula (IX) are reacted with ketene acid halides of the formula (V) in the presence of a diluent and, if appropriate, in the presence of an acid acceptor.

Suitable diluents for the process variant F) according to the invention are all inert organic solvents. Preference is given to using hydrocarbons, such as toluene and xylene, furthermore ethers, such as dibutyl ether, glycol dimethyl ether and diglycol dimethyl ether, moreover polar solvents, such as dimethyl sulphoxide, sulpholane, dimethylformamide and N-methyl-pyrrolidone.

Suitable acid acceptors for carrying out the process (F) according to the invention are all customary acid acceptors.

Preference is given to using tertiary amines, such as triethylamine, pyridine, diazabicyclooctane (DABCO), diazabicycloundecane (DBU), diazabicyclononene (DBN), Hünig base and N,N-dimethyl-aniline.

When carrying out the process (F) according to the invention, the reaction temperatures can be varied within a relatively wide range. Advantageously, the reaction is carried out at temperatures between 0° C. and 250° C., preferably between 20° C. and 220° C.

The process (F) according to the invention is advantageously carried out under atmospheric pressure.

When carrying out the process (F) according to the invention, the reaction components of the formulae (IX) and (V) in which A, W, X, Y and Z are each as defined above and Hal represents halogen, and, if appropriate, the acid acceptors, are generally employed in approximately equimolar amounts. However, it is also possible to use a relatively large excess (up to 5 mol) of one component or the other.

The process (G) is characterized in that compounds of the formula (X) in which A, B, $Q^1$, $Q^2$, W, Y, Z and $R^8$ are each as defined above are subjected to an intramolecular condensation in the presence of a base.

Suitable diluents for the process (G) according to the invention are all organic solvents which are inert towards the reaction participants. Preference is given to using hydrocarbons, such as toluene and xylene, furthermore ethers, such as dibutyl ether, tetrahydrofuran, dioxane, glycol dimethyl ether and diglycol dimethyl ether, moreover polar solvents, such as dimethyl sulphoxide, sulpholane, dimethylformamide and N-methyl-pyrrolidone. It is furthermore possible to use alcohols, such as methanol, ethanol, propanol, iso-propanol, butanol, isobutanol, tert-butanol.

Suitable bases (deprotonating agents) for carrying out the process (G) according to the invention are all customary proton acceptors. Preference is given to using alkali metal and alkaline earth metal oxides, hydroxides and carbonates, such as sodium hydroxide, potassium hydroxide, magnesium oxide, calcium oxide, sodium carbonate, potassium carbonate and calcium carbonate, which can also be employed in the presence of phase-transfer catalysts, such as, for example, triethylbenzylammonium chloride, tetrabutylammonium bromide, Adogen 464 (methyltrialkyl ($C_8$–$C_{10}$)ammonium chloride) or TDA 1 (tris(methoxyethoxyethyl)amine). Alkali metals such as sodium or potassium can also be used. Furthermore, alkali metal and alkaline earth metal amides and hydrides, such as sodium amide, sodium hydride and calcium hydride, and additionally also alkali metal alkoxides, such as sodium methoxide, sodium ethoxide and potassium tert-butoxide, can be employed.

When carrying the process (G) according to the invention, the reaction temperatures can be varied within a relatively wide range. In general, the reaction is carried out at temperatures between –75° C. and 250° C., preferably between –50° C. and 150° C.

The process (G) according to the invention is generally carried out under atmospheric pressure.

When carrying out the process (G) according to the invention, the reaction components of the formula (X) and the deprotonating bases are generally employed in approximately equimolar amounts. However, it is also possible to use a relatively large excess (up to 3 mol) of one component or the other.

The process (H) is characterized in that compounds of the formula (XI) in which A, B, $Q^3$, $Q^4$, $Q^5$, $Q^6$, W, X, Y, Z and $R^8$ are each as defined above are subjected to an intramolecular condensation in the presence of bases.

Suitable diluents for the process (H) according to the invention are all organic solvents which are inert towards the reaction participants. Preference is given to using hydrocarbons, such as toluene and xylene, furthermore ethers, such as dibutyl ether, tetrahydrofuran, dioxane, glycol dimethyl ether and diglycol dimethyl ether, moreover polar solvents, such as dimethyl sulphoxide, sulpholane, dimethylformamide and N-methyl-pyrrolidone. Alcohols, such as methanol, ethanol, propanol, iso-propanol, butanol, isobutanol and tert-butanol can also be used.

Suitable bases (deprotonating agents) for carrying out the process (H) according to the invention are all customary proton acceptors. Preference is given to using alkali metal and alkaline earth metal oxides, hydroxides and carbonates, such as sodium hydroxide, potassium hydroxide, magnesium oxide, calcium oxide, sodium carbonate, potassium carbonate and calcium carbonate, which can also be employed in the presence of phase-transfer catalysts, such as, for example, triethylbenzylammonium chloride, tetrabutylammonium bromide, Adogen 464 (methyltrialkyl ($C_8$–$C_{10}$)ammonium chloride) or TDA 1 (tris(methoxyethoxyethyl)-amine). Alkali metals such as sodium and potassium can also be used. Furthermore, alkali metal and alkaline earth metal amides and hydrides, such as sodium amide, sodium hydride and calcium hydride, and additionally also alkali metal alkoxides, such as sodium methoxide, sodium ethoxide and potassium tert-butoxide, can be employed.

When carrying the process (H) according to the invention, the reaction temperatures can be varied within a relatively wide range. In general, the reaction is carried out at temperatures between 0° C. and 250° C., preferably between 50° C. and 150° C.

The process (H) according to the invention is generally carried out under atmospheric pressure.

When carrying out the process (H) according to the invention, the reaction components of the formula (XII) and the deprotonating bases are generally employed in approximately equimolar amounts. However, it is also possible to use a relatively large excess up to 3 mol) of one component or the other.

For carrying out the process (I) according to the invention, palladium(0) complexes are suitable as catalysts. Tetrakis-(triphenylphosphine)palladium, for example, is preferred. Palladium(II) compounds, for example $PdCl_2$, may also be used if appropriate.

Suitable acid acceptors for carrying out the process (I) according to the invention are inorganic or organic bases These preferably include alkaline earth metal or alkali metal hydroxides, acetates, carbonates or bicarbonates, such as, for example, sodium hydroxide, potassium hydroxide, barium hydroxide or ammonium hydroxide, sodium acetate, potassium acetate, calcium acetate or ammonium acetate, sodium carbonate, potassium carbonate or ammonium carbonate, sodium bicarbonate or potassium bicarbonate, alkali metal fluorides, such as, for example caesium fluoride, and also tertiary amines, such as trimethylamine, triethylamine, tributylamine, N,N-dimethylaniline, N,N-dimethylbenzylamine, pyridine, N-methylpiperidine, N-methylmorpholine, N,N-dimethylaminopyridine, diazabicyclooctane (DABCO), diazabicyclononene (DBN) or diazabicycloundecene (DBU).

Suitable diluents for carrying out the process (I) according to the invention are water, organic solvents and any mixtures thereof. Examples include: aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, methylene chloride, chloroform, carbon tetrachloride, dichloroethane, trichloroethane or tetrachloroethylene; ethers, such as diethyl ether, diisopropyl ether, methyl t-butyl ether, methyl t-amyl ether, dioxane, tetrahydrofuran, 1,2-dimethoxyethane, 1,2-diethoxyethane, diethylenie glycol dimethyl ether or anisole; alcohols, such as methanol, ethanol, n- or i-propanol, n-, iso-, sec- or tert-butanol, ethanediol, propane-1,2-diol, ethoxyethanol, methoxyethanol, diethylene glycol monomethyl ether, diethylene glycol monoethyl ether; water.

The reaction temperature in the process (I) according to the invention can be varied within a relatively wide range. In general, the reaction is carried out at temperatures between 0° C. and +140° C., preferably between 50° C. and +100° C.

When carrying out the process (I) according to the invention, boronic acid of the formula (XII) in which Z is as defined above and compounds of the formulae (I-1-a) to (I-8-a) in which A, B, D, $Q^1$, $Q^2$, $Q^3$, $Q^4$, $Q^5$, $Q^6$, W, X, Y and Z are each as defined above are employed in a molar ratio of from 1:1 to 3:1, preferably from 1:1 to 2:1. In general, 0.005 to 0.5 mol, preferably 0.01 mol to 0.1 mol, of catalyst is employed per mole of the compounds of the formulae (I-1-a) to (I-8-a). The base is usually employed in excess.

The process (J-α) is characterized in that compounds of the formulae (I-1-a) to (I-8-a) are in each case reacted with carbonyl halides of the formula (XIII), if appropriate in the presence of a diluent and if appropriate in the presence of an acid binder.

Suitable diluents for the process (J-α) according to the invention are all solvents which are inert towards the acyl halides. Preference is given to using hydrocarbons, such as benzine, benzene, toluene, xylene and tetralin, furthermore halogenated hydrocarbons, such as methylene chloride, chloroform, carbon tetrachloride, chlorobenzene and o-dichlorobenzene, moreover ketones, such as acetone and methyl isopropyl ketone, furthermore ethers, such as diethyl ether, tetrahydrofuran and dioxane, additionally carboxylic esters, such as ethyl acetate, and also strongly polar solvents, such as dimethyl sulphoxide and sulpholane. The hydrolytic stability of the acyl halide permitting, the reaction can also be carried out in the presence of water.

Suitable acid binders for the reaction according to the process (J-α) according to the invention are all customary acid acceptors. Preference is given to using tertiary amines, such as triethylamine, pyridine, diazabicyclooctane (DABCO), diazabicycloundecene (DBU), diazabicyclononene (DBN), Hünig base and N,N-dimethyl-aniline, furthermore alkaline earth metal oxides, such as magnesium oxide and calcium oxide, moreover alkali metal and alkaline earth metal carbonates, such as sodium carbonate, potassium carbonate and calcium carbonate, and also alkali metal hydroxides such as sodium hydroxide and potassium hydroxide.

The reaction temperatures in the process (J-α) according to the invention can be varied within a relatively wide range. In general, the reaction is carried out at temperatures between −20° C. and +150° C., preferably between 0° C. and 100° C.

When carrying out the process (J-α) according to the invention, the starting materials of the formulae (I-1-a) to (I-8-a) and the carbonyl halide of the formula (XIII) are generally in each case employed in approximately equivalent amounts. However, it is also possible to employ a relatively large excess (up to 5 mol) of the carbonyl halide. Work-up is carried out by customary methods.

The process (J-β) is characterized in that compounds of the formulae (I-1-a) to (I-8-a) are reacted with carboxylic anhydrides of the formula (XIV), if appropriate in the presence of a diluent and if appropriate in the presence of an acid binder.

Preferred diluents for the process (J-β) according to the invention are those diluents which are also preferred when acyl halides are used. Otherwise, it is also possible for a carboxylic anhydride employed in excess to act simultaneously as a diluent.

In the process (J-β), acid binders which are added, if appropriate, are preferably those acid binders which are also preferred when acyl halides are used.

In the process (J-β) according to the invention, the reaction temperatures can be varied within a relatively wide range. In general, the reaction is carried out at temperatures between −20° C. and +150° C., preferably between 0° C. and 100° C.

When carrying out the process (J-β) according to the invention, the starting materials of the formulae (I-1-a) to (I-8-a) and the carboxylic anhydride of the formula (XIV) are generally each employed in approximately equivalent amounts. However, it is also possible to use a relatively large excess (up to 5 mol) of the carboxylic anhydride. Work-up is carried out by customary methods.

In general, the adopted procedure is to remove diluent and excess carboxylic anhydride and also the carboxylic acid formed by distillation or by washing with an organic solvent or with water.

The process (K) is characterized in that compounds of the formulae (I-1-a) to (I-8-a) are in each case reacted with chloroformic esters or chloroformic thiol esters of the formula (XV), if appropriate in the presence of a diluent and if appropriate in the presence of an acid binder.

Suitable acid binders for the reaction according to the process (K) according to the invention are all customary acid acceptors. Preference is given to using tertiary amines, such as triethylamine, pyridine, DABCO, DBU, DBA, Hünig base and N,N-dimethyl-aniline, furthermore alkaline earth metal oxides, such as magnesium oxide and calcium oxide, moreover alkali metal carbonates and alkaline earth metal carbonates, such as sodium carbonate, potassium carbonate and calcium carbonate, and also alkali metal hydroxides such as sodium hydroxide and potassium hydroxide.

Suitable diluents for the process (K) according to the invention are all solvents which are inert towards the chloroformic esters or chloroformic thiol esters. Preference is given to using hydrocarbons, such as benzine, benzene, toluene, xylene and tetralin, furthermore halogenated hydrocarbons, such as methylene chloride, chloroform, carbon tetrachloride, chlorobenzene and o-dichlorobenzene, moreover ketones, such as acetone and methyl isopropyl ketone, furthermore ethers, such as diethyl ether, tetrahydrofuran and dioxane, additionally carboxylic esters, such as ethyl acetate, and also strongly polar solvents, such as dimethyl sulphoxide and sulpholane.

When carrying out the process (K) according to the invention the reaction temperatures can be varied within a relatively wide range. If the reaction is carried out in the presence of a diluent and an acid binder, the reaction temperatures are generally between −20° C. and +100° C., preferably between 0° C. and 50° C.

The process (K) according to the invention is generally carried out under atmospheric pressure.

When carrying out the process (K) according to the invention, the starting materials of the formulae (I-1-a) to (I-8-a) and the appropriate chloroformic ester or chloroformic thiol ester of the formula (XV) are generally in each case employed in approximately equivalent amounts. However, it is also possible to employ a relatively large excess (up to 2 mol) of one component or the other. Work-up is carried out by customary methods. In general, precipitated salts are removed and the reaction mixture that remains is concentrated by stripping off the diluent.

The process (L) according to the invention is characterized in that compounds of the formulae (I-1-a) to (I-8-a) are in each case reacted with compounds of the formula (XVI) in the presence of a diluent and, if appropriate, in the presence of an acid binder.

In the preparation process (L), approximately 1 mol of chloromonothioformic ester or chlorodithioformic ester of the formula (XVI) is reacted per mole of starting material of the formulae (I-1-a) to (I-8-a), at from 0 to 120° C., preferably from 20 to 60° C.

Suitable diluents which are added if appropriate are all inert polar organic solvents, such as ethers, amides, sulphones, sulphoxides, but also halogenoalkanes.

Preference is given to using dimethyl sulphoxide, tetrahydrofuran, dimethylformamide or methylene chloride.

If, in a preferred embodiment, the enolate salt of the compounds (I-1-a) to (I-8-a) is prepared by addition of strong deprotonating agents, such as, for example, sodium hydride or potassium tert-butoxide, it is not necessary to add further acid binders.

If acid binders are employed, these are customary inorganic or organic bases, for example sodium hydroxide, sodium carbonate, potassium carbonate, pyridine, triethylamine.

The reaction can be carried out at atmospheric pressure or under elevated pressure and is preferably carried out at atmospheric pressure. Work-up is carried out by customary methods.

The process (M) according to the invention is characterized in that compounds of the formulae (I-1-a) to (I-8-a) are in each case reacted with sulphonyl chlorides of the formula (XVII), if appropriate in the presence of a diluent and if appropriate in the presence of an acid binder.

In the preparation process (M), approximately 1 mol of sulphonyl chloride of the formula (XVII) is reacted per mole of starting material of the formula (I-1-a) to (I-8-a), at from −20 to 150° C., preferably at from 20 to 70° C.

Suitable diluents which are added if appropriate are all inert polar organic solvents, such as ethers, amides, nitriles, sulphones, sulphoxides or halogenated hydrocarbons, such as methylene chloride.

Preference is given to using dimethyl sulphoxide, tetrahydrofuran, dimethlyl-formamide, methylene chloride.

If, in a preferred embodiment, the enolate salt of the compounds (I-1-a) to (I-8-a) is prepared by addition of strong deprotonating agents (such as, for example, sodium hydride or potassium tert-butoxide), it is not necessary to add further acid binders.

If acid binders are employed, these are customary inorganic or organic bases, for example sodium hydroxide, sodium carbonate, potassium carbonate, pyridine, triethylamine.

The reaction can be carried out at atmospheric pressure or under elevated pressure and is preferably carried out at atmospheric pressure. Work-up is carried out by customary methods.

The process (N) according to the invention is characterized in that compounds of the formulae (I-1-a) to (I-8-a) are in each case reacted with phosphorus compounds of the formula (XVIII), if appropriate in the presence of a diluent and if appropriate in the presence of an acid binder.

In the preparation process (N), 1 to 2, preferably 1 to 1.3, mol of the phosphorus compound of the formula (XVIII) are reacted per mole of the compounds (I-1-a) to (I-8-a) at temperatures between −40° C. and 150° C., preferably between −10 and 110° C., to give compounds of the formulae (I-1-e) to (I-8-e).

Suitable solvents which are added if appropriate are all inert polar organic solvents, such as ethers, amides, nitriles, alcohols, sulphides, sulphones, sulphoxides, etc.

Preference is given to using acetonitrile, dimethyl sulphoxide, tetrahydrofuran, dimethylformamide, methylene chloride.

Suitable acid binders which are added if appropriate are customary inorganic or organic bases such as hydroxides, carbonates or amines. Examples include sodium hydroxide, sodium carbonate, potassium carbonate, pyridine, triethylamine.

The reaction can be carried out at atmospheric pressure or under elevated pressure and is preferably carried out at atmospheric pressure. Work-up is carried out by customary methods of organic chemistry. The resulting end products are preferably purified by crystallization, chromatographic purification or by so-called "incipient distillation", i.e. removal of the volatile components under reduced pressure.

The process (O) is characterized in that compounds of the formulae (I-1-a) to (I-8-a) are reacted with metal hydroxides or metal alkoxides of the formula (XIX) or amines of the formula (XX), if appropriate in the presence of a diluent.

Preferred diluents for the process (O) according to the invention are ethers, such as tetrahydrofuran, dioxane, diethyl ether, or else alcohols, such as methanol, ethanol, isopropanol, but also water.

The process (O) according to the invention is generally carried out under atmospheric pressure.

The reaction temperatures are generally between −20° C. and 100° C., preferably between 0° C. and 50° C.

The process (P) according to the invention is characterized in that compounds of the formulae (I-1-a) to (I-8-a) are in each case reacted with (P-α) compounds of the formula (XXI), if appropriate in the presence of a diluent and if appropriate in the presence of a catalyst, or (Pβ) with compounds of the formula (XXII), if appropriate in the presence of a diluent and if appropriate in the presence of an acid binder.

In the preparation process (P-α), approximately 1 mol of isocyanate of the formula (XXI) is reacted per mole of starting material of the formulae (I-1-a) to (I-8-a), at from 0 to 100° C., preferably at from 20 to 50° C.

Suitable diluents which are added if appropriate are all inert organic solvents, such as ethers, amides, nitriles, sulphioties, sulphoxides.

If appropriate, catalysts may be added to accelerate the reaction. Very advantageously, the catalysts which are employed are organotin compounds, such as, for example, dibutyltin dilaurate. The reaction is preferably carried out at atmospheric pressure.

In the preparation process (P-β), approximately 1 mol of carbamoyl chloride of the formula (XXII) is reacted per mole of starting material of the formulae (I-1-a) to (I-8-a), at from −20 to 150° C., preferably from 0 to 70° C.

Suitable diluents which are added if appropriate are all inert polar organic solvents, such as ethers, amides, sulphones, sulphoxides or halogenated hydrocarbons.

Preference is given to using dimethyl sulphoxide, tetrahydrofuran, dimethylformamide or methylene chloride.

If, in a preferred embodiment, the enolate salt of the compounds (I-1-a) to (I-8-a) is prepared by addition of strong deprotonating agents (such as, for example, sodium hydride or potassium tert-butoxide), it is not necessary to add further acid binders.

If acid binders are employed, these are customary inorganic or organic bases, for example sodium hydroxide, sodium carbonate, potassium carbonate, triethylamine or pyridine.

The reaction can be carried out at atmospheric pressure or under elevated pressure and is preferably carried out at atmospheric pressure. Work-up is carried out by customary methods.

The active compounds are suitable for controlling animal pests, preferably arthropods and nematodes, in particular insects and arachnids, which are encountered in agriculture, in forestry, in the protection of stored products and of materials, and in the hygiene field. They are active against normally sensitive and resistant species and against all or some stages of development. The abovementioned pests include:

From the order of the Isopoda, for example, *Oniscus asellus, Armadillidium vulgare* and *Porcelhio scaber*. From the order of the Diplopoda, for example, *Blaniulus guttulatus*. From the order of the Clilopoda, for example, *Geophilus carpophagus* and Scutigera spec. From the order of the Symphyla, for example, *Scutigerella immaculata*. From the order of the Thysanura, for example, *Lepisma saccharina*. From the order of the Collembola, for example, *Onychiurus armatus*. From the order of the Orthoptera, for example, *Blatta orientalis, Periplaneta americana, Leucophaea maderae, Blattella germanica, Acheta domesticus*, Gryllotalpa spp., *Locusta migratoria* migratoriodes, *Melanoplus differentialis* and *Schistocerca gregaria*.

From the order of the Dermaptera, for example, *Forficula auricularia*. From the order of the Isoptera, for example, Reticulitermes spp.

From the order of the Anoplura, for example, *Phylloxera vastatrix*, Pemphigus spp., *Pediculus humanus corporis*, Haematopinus spp. and Linognathus spp. From the order of the Mallophaga, for example, Trichodectes spp. and Damalinea spp. From the order of the Thysanoptera, for example, *Frankliniella occidentalis, Hercinothrips femoralis, Thrips palmi,* and *Thrips tabaci*. From the order of the Heteroptera, for example, Eurygaster spp., *Dysdercus intermedius, Piesma quadrata, Cimex lectularius, Rhodnius prolixus* and Triatoma spp.

From the order of the Homoptera, for example, *Aleurodes brassicae, Bemisia tabaci, Trialeurodes vaporariorum, Aphis gossypii, Brevicoryne brassicac, Cryptomyzus ribis, Aphis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Spodoptera exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana.*

From the order of the Coleoptera, for example, *Anobium punctatum, Rhizopertha dominica, Acanthoscelides obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varive stis,* Atomaria spp., *Oryzaephilus surinamensis, Antho nomus* spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., *Cono derus* spp., *Melolontha melolontha, Amphimallon solsti tialis* and *Costelytra zealandica.*

From the order of the Hymenoptera, for example, Diprion sppi, Hoplocampa spp., Lasius spp., *Monomorium pharaonis* and Vespa spp.

From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Liriomyza spp., Stomoxys spp., Oestrus spp., Hypoderma spp., Tabanus spp., Tannia spp., *Bibio hortulanus,* Oscinella frit, Phorbia spp., *Pegomyia hyoscyami, Ceratitis capitata, Dacus oleae* and *Tipula paludosa.*

From the order of the Siphonaptera, for example, *Xenopsylla cheopis* and Ceratophyllus spp. From the order of the Arachnida, for example, *Scorpio maurus* and *Latrodectus mactans.*

From the order of the Acarina, for example, *Acarus siro,* Argas spp., Ornithodoros spp., *Dermanyssus gallinae, Eriophyes ribis, Phyiiocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp.

The active compounds according to the invention have high insecticidal and acaricidal activity after foliar and soil application.

They can be employed particularly successfully against insects which are harmful to plants, such as, for example, against the larvae of the mustard beetle (Phaedon cochleariae) or against the larvae of the green rice leafhopper (Nephotettix cincticeps) and against the larvae of the green peach aphid (Myzus persicae).

The active compounds according to the invention can furthermore be used as defoliants, desiccants, haulm killers and, especially, as weedkillers. By weeds, in the broadest sense, there are to be understood all plants which grow in locations where they are undesired. Whether the substances according to the invention act as total or selective herbicides depends essentially on the amount used.

The dosages of the active compounds according to the invention necessary for combating weeds are between 0.001 and 10 kg/ha, preferably between 0.005 and 5 kg/ha.

The active compounds according to the invention can be used, for example, in connection with the following plants:

Dicotyledonous weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamiurn, Veronica, Abutilon, Emex, Datura, Viola, Galeopsis, Papaver, Centaurea, Trifolium, Ranunculus and Taraxacum.

Dicotyledonous cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledonous weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cycnodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledonous cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hop fields, on ornamental and sports lawns and meadow areas and for the selective combating of weeds in annual cultures.

The active compounds according to the invention are particularly suitable for selectively controlling monocotyledonous weeds in dicotyledonous crops by the pre-and post-emergence method. For example, they can be employed very successfully for controlling harmful grasses in cotton or sugar beet.

The active compounds can be converted into the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable, in the main, aromatics, such as xylene, toluene or alkylnaphthalenies, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol, as well as their ethers and esters, ketones, such as acetone, methyl ethyl ketone, methyl isobutyl ketone or cyclohexanone, strongly polar solvents, such as dimethylformamide and dimethyl sulphoxide, as well as water.

As solid carriers the following are suitable:

for example, ammonium salts and ground natural minerals, such as kaolins, clays, talc, chalk, quartz, attapulgite, montmorillonite or diatomaceous earth, and ground synthetic minerals, such as highly disperse silica, alumina and silicates; as solid carriers for granules there are suitable, for example, crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable, for example, non-ionic and anionic emulsifiers, such as polyoxyethylene fatty acid esters, polyoxyethylene fatty alcohol ethers, for example alkylaryl polyglycol ethers, alkyl sulphonates, alkyl sulphates, aryl sulphonates as well as albumen hydrolysis products; as dispersing agents there are suitable, for example, lignin-sulphite waste liquors and methylcellulose.

Tackifiers such as carboxymethylcellulose and natural and synthetic polymers in the form of powders, granules or latexes, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95% by weight of active compound, preferably between 0.5 and 90%, and additionally preferably extenders and/or surfactants.

The active compound according to the invention can be present in its commercially available formulations and in the use forms prepared from these formulations as a mixture with other active compounds, such as insecticides, baits, sterilizing agents, acaricides, nematicides, fungicides, growth-regulating substances or herbicides. The insecticides include, for example, phosphoric acid esters, carbamates, carboxylic acid esters, chlorinated hydrocarbons, phenylureas, substances produced by microorganisms, and the like.

Particularly favourable mixing partners are, for example, the following:

Fungicides:

2-aminobutane; 2-anilino-4-methyl-6-cyclopropyl-pyrimidine; 2',6'-dibromo-2-methyl-4'-trifluoromethoxy-4'-trifluoro-methyl-1,3-thiazole-5-carboxanilide; 2,6-dichloro-N-(4-trifluoromethylbenzyl)-benzamide; (E)-2-methoxyimino-N-methyl-2-(2-phenoxy-phenyl)-acetamide; 8-hydroxyquinoline sulphate; methyl (E)-2-{2-[6-(2-cyanophenoxy)-pyrimidin-4-yloxy]-phenyl}-3-methoxyacrylate; methyl (E)-methoximino[alpha-(o-tolyloxy)-o-tolyl]acetate; 2-phenylphenol (OPP), aldimorph, ampropylfos, anilazine, azaconazole, benalaxyl, benodanil, benomyl, binapacryl, biphenyl, bitertanol, blasticidin-S, bromuconazole, bupirimate, buthiobate, calcium polysulphide, captafol, captan, carbendazim, carboxin, quinomethionate, chloroneb, chloropicrin, chlorothalonil, chilozolinate, cufraneb, cymoxanil, cypro-conazole, cyprofuram, dichlorophen, diclobutrazol, diclofluanid, diclomezin, dicloran, diethofencarb, difenoconazole, dimethirimol, dimethomorph, diniconazole, dinocap, diphenylatmine, dipyrithion, ditalimfos, ditlianon, dodine, drazoxolon, edifenphos, epoxyconazole, ethirimol, etridiazole, fenarimol, fenbuconazole, fenfuram, fenitropan, fenpiclonil, fenpropidin, fenpropimorph, fentin acetate, fentin hydroxide, ferbam, ferimzone, fluazinam, fludioxonil, fluoromide, fluquinconazole, flusilazole, flusulfamide, flutolanil, flutriafol, folpet, fosetyl-aluminium, fthalide, fuberidazole, furalaxyl, furmecyclox, guazatine, hexachlorobenzene, hexaconazole, hymexazol, imazalil, imibenconazole, iminoctadine, iprobenfos (IBP), iprodione, isoprothiolane, kasugamycin, copper preparations such as copper hydroxide, copper naphthenate, copper oxychloride, copper sulphate, copper oxide, oxine-copper and Bordeaux mixture, mancopper, mancozeb, maneb, mepanipyrim, mepronil, metalaxyl, metconazole, methasulfocarb, methfuroxam, metiram, metsulfovax, myclobutanil, nickel dimethyldithiocarbamate, nitrothal-isopropyl, nuarimol, ofurace, oxadixyl, oxamocarb, oxycarboxin, pefurazoate, penconazole, pencycuron, phosdiphen, phthalide, pimaricin, piperalin, polycarbamate, polyoxin, probenazole, prochloraz, procymidone, proparmocarb, propiconazole, propineb, pyrazophos, pyrifenox, pyrimethanil, pyroquilon, quintozene (PCNB), sulphur and sulphur preparations, tebuconazole, tecloftalam, tecnazene, tetraconazole, thiabendazole, thicyofen, thiophanate-methyl, thiram, tolclophos-methyl, tolylfluanid, triadimefon, triadimenol, triazoxide, trichiamide, tricyclazole, tridemorph, triflumizole, triforine, triticonazole, validamycin A, vinclozolin, zineb, ziram Bactericides:

bronopol, dichlorophen, nitrapyrin, nickel dimethyldithiocarbamate, kasugamycin, octhilinon, furancarboxylic acid, oxytetracyclin, probenazol, streptomycin, tecloftalam, copper sulphate and other copper preparations.

Insecticides/Acaricides/Nematicides:

abamectin, AC 303 630, acephate, acrinathrin, alanycarb, aldicarb, alphamethrin, amitraz, avermectin, AZ 60541, azadirachtin, azinphos A, azinphos M, azocyclotin, Bacillus thuringiensis, bendiocarb, benfuracarb, bensultap, betacyfluthrin, bifenthrin, BPMC, brofenprox, bromophos A, bufencarb, buprofezin, butocarboxim, butylpyridaben, cadusafos, carbaryl, carbofuran, carbophenothion, carbosulfan, cartap, CGA 157 419, CGA 184699, chloethocarb, chlorethoxyfos, chlorfenvinphos, chlorfluazuron, chlomephos, chlorpyrifos, chlorpyrifos M, cis-resmethrin, clocythrin, clofentezine, cyanophos, cycloprothrin, cyfluthrin, cyhalothrin, cylexatin, cypermethrin, cyromazine, deltamethrin, demeton M, demeton S, demeton-S-methyl, diafenthiuron, diazinon, dichlofenthion, dichlorvos, dicliphos, dicrotophos, diethion, diflubenzuron, dimethoate, dimnethylvinphos, dioxathion, disulfoton, edifenphos, emamectin, esfenvalerate, ethiofencarb, etlion, ethofenprox, ethoprophos, etrimphos, fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, flucycloxuron, flucythrinate, flufenoxuron, flufenprox, fluvalinate, fonophos, formothion, fosthiazate, fubfenprox, furathiocarb, HCH, heptenophos, hexaflumuron, hexythiazox, imidacloprid, iprobenfos, isazophos, isofenphos, isoprocarb, isoxathion, ivermectin, lambda-cyhalothrin, lufenuron, malathion, mecarbam, mevinphos, mesulfenphlos, metaldehyde, methacrifos, methamidophos, methidathion, methiocarb, methomyl, metolcarb, milbemectin, monocrotophos, moxidectin, naled, NC 184, NI 25, nitenipyram, omethoate, oxamyl, oxydemethon M, oxydeprofos, parathion A, parathion M, permithrin, phenthoate, phorate, phosalone, phosmet, phosphamidon, phoxim, pirimicarb, pirimiphos M, pirimiphos A, profenofos, promecarb, propaphos, propoxur, prothiofos, prothoate, pymetrozin, pyrachlophos, pyridaphenthion, pyresmethrin, pyrethrum, pyridaben, pyrimidifen, pyriproxifen, quinalphos, RH 5992, salithion, sebufos, silafluofen, sulfotep, suiprofos, tebufenozid, tebufenpyrad, tebupirimiphos, teflubenzuron, tefluthrin, temephos, terbam, terbufos, tetrachlorvinphos, thiafenox, thiodicarb, thiofanox, thiomethon, thionazin, thuringiensin, tralomethrin, triarathen, triazophos, triazuron, trichlorfon, triflumuron, trimethacarb, vamidothion, XMC, xylylcarb, YI 5301/5302, zetametlirin:

Herbicides:

for example anilides, such as, for example, diflufenican and propanil; arylcarboxylic acids such as, for example, dichloropicolinic acid, dicamba and picloram; aryloxyalkanoic acids, such as, for example, 2,4 D, 2,4 DB, 2,4 DP, fluroxypyr, MCPA, MCPP and triclopyr; aryloxyphenoxy-alkanoic acid esters, such as, for example, diclofop-methyl, fenoxaprop-ethyl, fluazifop-butyl, haloxyfop-methyl and quizalofop-ethyl; azinones, such as, for example, chloridazon and norflurazon; carbamates, such as, for example, chlorpropham, desmedipham, phenmedipham and propham; chloroacetanilides, such as, for example, alachlor, acetochlor, butachlor, metazachlor, metolachlor, pretilachlor and propachlor; dinitroanilines, such as, for example, oryzalin, pendimethalin and trifluralin; diphenyl ethers, such as, for example, acifluorfen, bifenox, fluoroglycofen, fomesafen, halosafen, lactofen and oxyfluorfen; ureas, such as, for example, chlortoluron, diuron, fluometuron, isoproturon, linuron and methabenzthiazuron; hydroxylamines, such as, for example, alloxydim, clethodim, cycloxydim, sethoxydim and tralkoxydim; imidazolinones, such as, for example, imazethapyr, imazamethabenz, imazapyr and imazaquin; nitriles, such as, for example, bromoxynil, dichlobenil and ioxynil; oxyacetamides, such as, for example, mefenacet; sulfonylureas, such as, for example, amindosulfuron, bensulfuron-methyl, chlorimuron-ethyl, chlorsulfuron, cinosulfuron, metsulfuron-methyl, nicosulfuron, primisulfuron, pyrazosulfuron-ethyl, thifenlsulfuron-methyl, triasulfuron and tribenuron-methyl; thiocarbamates, such as, for example, butylate, cycloate, di-allate, EPTC, esprocarb, molinate, prosulfocarb, thiobencarb and triallate; triazines, such as, for example, atrazine, cyanazine, simazine, simetryn, terbutryn and terbutylazine; triazinones, such as, for example, hexazinone, metamitron and metribuzin; others, such as, for example, aminotriazole, benfuresate, bentazone, cinmethylin, clomazone, clopyralid, difenzoquat, dithiopyr, ethofumesate, fluorochloridone, glufosinate, glyphosate, isoxaben, pyridate, quinchlorac, quinmerac, sulphosate and tridiphane.

The active compound according to the invention can furthermore be present in its commercially available formulations and in the use forms, prepared from these formulations, as a mixture with synergistic agents. Synergistic agents are compounds which increase the action of the active compounds without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are used in a customary manner appropriate for the use forms.

When used against hygiene pests and pests of stored products, the active compound has outstanding residual action on wood and clay and by a good stability to alkali on limed substrates.

The active compounds according to the invention act not only against plant, hygiene and stored product pests, but also in the veterinary medicine sector against animal parasites (ectoparasites), such as hard ticks, soft ticks, mange nites, leaf mites, flies (biting and licking), parasitic fly larvae, lice, hair lice, feather lice and fleas. These parasites include:

From the order of the Anoplurida, for example, Haematopinus spp., Linognathus spp., Pediculus spp., Phtirus spp. and Solenopotes spp.

From the order of the Mallophagida and the suborders Amblycerina and Ischnocerina, for example, Trimenopon spp., Menopon spp., Trinoton spp., Bovicola spp., Werneckiella spp., Lepikentron spp., Damalina spp., Trichodectes spp. and Felicola spp.

From the order of the Diptera and the suborders Nematocerina and Brachycerina, for example, Aedes spp., Anopheles spp., Culex spp., Simulium spp., Eusimulium spp., Phlebotomus spp., Lutzomyia spp., Culicoides spp., Chrysops spp., Hybomitra spp., Atylotus spp., Tabanus spp., Haematopota spp., Philipomyia spp., Braula spp., Musca spp., Hydrotaea spp., Stomoxys spp., Haematobia spp., Morellia spp., Fannia spp., Glossina spp., Calliphora spp., Lucilia spp., Chrysomyia spp., Wohlfahrtia spp., Sarcophaga spp., Oestrus spp., Hypoderma spp., Gasterophilus spp., Hippobosca spp., Lipoptena spp. and Melophagus spp.

From the order of the Siphonapterida, for example, Pulex spp., Ctenocephalides spp., Xenopsylla spp. and Ceratophyllus spp.

From the order of the Heteropterida, for example, Cimex spp., Triatoma spp., Rhodnius spp. and Panstrongylus spp.

From the order of the Blattarida, for example, *Blatta orientalis, Periplaneta americana, Blattela germanica* and Supella spp.

From the subclass of the Acaria (Acarida) and the orders of the Meta- and Mesostigmiiata, for example, Argas spp., Omithodorus spp., Otabius spp., Ixodes spp., Amblyonmma spp., Boophilus spp., Dermacentor spp., Haemophysalis spp., Hyalomma spp., Rhipicephalus spp., Dermanyssus spp., Raillietia spp., Pneumonyssus spp., Sternostoma spp. and Varroa spp.

From the order of the Actinedida (Prostigmata) und Acaridida (Astigmata), for example, Acarapis spp., Cheyletiella spp., Ornithocheyletia spp., Myobia spp., Psorergates spp., Demodex spp., Trombicula spp., Listrophorus spp., Acarus spp., Tyrophagus spp., Caloglyphus spp., Hypodectes spp., Pterolichus spp., Psoroptes spp., Chorioptes spp., Otodectes spp., Sarcoptes spp., Notoedres spp., Knemidocoptes spp., Cytodites spp. and Laminosioptes spp.

The active compounds of the formula (I) according to the invention are also suitable for controlling arthropods which infest agricultural productive livestock, such as, for example, cattle, sheep, goats, horses, pigs, donkeys, camels, buffalo, rabbits, chickens, turkeys, ducks, geese and bees, other pets, such as, for example, dogs, cats, caged birds and aquarium fish, and also so-called test animals, such as, for example, hamsters, guinea pigs, rats and mice. By controlling these arthropods, cases of death and reduction in productivity (for meat, milk, wool, hides, eggs, honey etc.) should be diminished, so that more economic and easier animal husbandry is possible by use of the active compounds according to the invention.

The active compounds according to the invention are used in the veterinary sector in a known manner by enteral administration in the formn of, for example, tablets, capsules, potions, drenches, granules, pastes, boluses, the feed-througlh process and suppositories, by parenteral administration, such as, for example, by injection (intramuscular, subcutaneous, intravenous, intraperitoneal and the like), implants, by nasal administration, by dermal use in the form, for example, of dipping or bathing, spraying, pouring on and spotting on, washing and powderilng, and also with the aid of moulded articles containing the active compound, such as collars, ear marks, tail marks, limb bands, halters, marking devices and the like.

When used for cattle, poultry, pets and the like, the active compounds of the formula (I) can be used as formulations (for example powders, emulsions, free-flowing compositions), which comprise the active compounds in an amount of 1 to 80% by weight, directly or after 100 to 10000-fold dilution, or they can be used as a chemical bath.

It has furthermore been found that the compounds of the formula (I) according to the invention also have a strong insecticidal action against insects which destroy industrial materials.

The following insects may be mentioned as examples and as preferred—but without limitation:

Beetles, such as

Hylotrupes bajulus, Chlorophorus phosis, Anobium punctatum, Xestobium rufovillosum, Ptilinus pecticomis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis, Xyleborus spec., Tryptodendron spec., Apate monachus, Bostrychus capucins, Heterobostrychus brunneus, Sinoxylon spec., Dinoderus minutus.

Hymenopterons, such as

Sirex juvencus, Urocerus gigas, Urocerus gigas taignus, Urocerus augur

Termites, such as

Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadenisis, Coptotermes formosanus.

Bristletails, such as

Lepisma saccharina.

Industrial materials in the present connection are to be understood as meaning non-living materials, such as, preferably, plastics, adhesives, sizes, papers and cards, leather, wood and processed wood products and coating compositions.

Wood and processed wood products are materials to be protected, especially preferably, from insect infestation.

Wood and processed wood products which can be protected by the agents according to the invention or mixtures comprising these are to be understood as meaning, for example: building timber, wooden beams, railway sleepers, bridge components, boat jetties, wooden vehicles, boxes, pallets, containers, telegraph poles, wood panelling, wooden windows and doors, plywood, chipboard, joinery or wooden products which are used quite generally in house building or in building joinery.

The active compounds can be used as such, in the form of concentrates or in generally customary formulations, such as powders, granules, solutions, suspensions, emulsions or pastes.

The formulations mentioned can be prepared in a manner known per se, for example by mixing the active compounds with at least one solvent or diluent, emulsifier, dispersing agent and/or binder or fixing agent, a water repellant, if appropriate siccatives and UV stabilizers and if appropriate dyestuffs and pigments, and also other processing auxiliaries.

The insecticidal compositions or concentrates used for the preservation of wood and wood-derived timber products comprise the active compound according to the invention in a concentration of 0.0001 to 95% by weight, in particular 0.001 to 60% by weight.

The amount of the compositions or concentrates employed depends on the nature and occurrence of the insects and on the medium. The optimum amount employed can be determined for the use in each case by a series of tests. In general, however, it is sufficient to employ 0.0001 to 20% by weight, preferably 0.001 to 10% by weight, of the active compound, based on the material to be preserved.

Solvents and/or diluents which are used are an organic chemical solvent or solvent mixture and/or an oily or oil-like organic chemical solvent or solvent mixture of low volatility and/or a polar organic chemical solvent or solvent mixture and/or water, and if appropriate an emulsifier and/or wetting agent.

Organic chemical solvents which are preferably used are oily or oil-like solvents having an evaporation number above 35 and a flash point above 30° C., preferably above 45° C. Substances which are used as such oily or oil-like water-insoluble solvents of low volatility are appropriate mineral oils or aromatic fractions thereof, or solvent mixtures containing mineral oils, preferably white spirit, petroleum and/or alkylbenzene.

Mineral oils having a boiling range from 170 to 220° C., white spirit having a boiling range from 170 to 220° C., spindle oil having a boiling range from 250 to 350° C., petroleum and aromatics having a boiling range from 160 to 280° C., terpentine oil and the like, are advantageously employed.

In a preferred embodiment, liquid aliphatic hydrocarbons having a boiling range from 180 to 210° C. or high-boiling mixtures of aromatic and aliphatic hydrocarbons having a boiling range from 180 to 220° C. and/or spindle oil and/or monochloronaphthalene, preferably α-monochloronaphthalene, are used.

The organic oily or oil-like solvents of low volatility which have an evaporation number above 35 and a flash point above 30° C., preferably above 45° C., can be replaced in part by organic chemical solvents of high or medium volatility, providing that the solvent mixture likewise has an evaporation number above 35 and a flash point above 30° C., preferably above 45° C., and that the insecticide/fungicide mixture is soluble or emulsifiable in this solvent mixture.

According to a preferred embodiment, some of the organic chemical solvent or solvent mixture is replaced by an aliphatic polar organic chemical solvent or solvent mixture. Aliphatic organic chemical solvents containing hydroxyl and/or ester and/or ether groups, such as, for example, glycol ethers, esters or the like, are preferably used.

Organic chemical binders which are used in the context of the present invention are the synthetic resins and/or binding drying oils which are known per se, are water-dilutable and/or are soluble or dispersible or emulsifiable in the organic chemical solvents employed, in particular binders consisting of or comprising an acrylate resin, a vinyl resin, for example polyvinyl acetate, polyester resin, polycondensation or polyaddition resin, polyurethane resin, alkyd resin or modified alkyd resin, phenolic resin, hydrocarbon resin, such as indene-cumarone resin, silicone resin, drying vegetable oils and/or drying oils and/or physically drying binders based on a natural and/or synthetic resin.

The synthetic resin used as the binder can be employed in the form of an emulsion, dispersion or solution. Bitumen or bituminous substances can also be used as binders in an amount of up to 10% by weight. Dyestuffs, pigments, water-repelling agents, odour correctants and inhibitors or anticorrosive agents and the like which are known per se can additionally be employed.

It is preferred according to the invention for the composition or concentrate to comprise, as the organic chemical binder, at least one alkyd resin or modified alkyd resin and/or one drying vegetable oil. Alkyd resins having an oil content of more than 45% by weight, preferably 50 to 68% by weight, are preferably used according to the invention.

All or some of the binder mentioned can be replaced by a fixing agent (mixture) or a plasticizer (mixture). These additives are intended to prevent evaporation of the active compounds and crystallization or precipitation. They preferably replace 0.01 to 30% of the binder (based on 100% of the binder employed).

The plasticizers originate from the chemical classes of phthalic acid esters, such as dibutyl, dioctyl or benzyl butyl phthalate, phosphoric acid esters, such as tributyl phosphate, adipic acid esters, such as di-(2-ethylhexyl) adipate, stearates, such as butyl stearate or amyl stearate, oleates, such as butyl oleate, glycerol ethers or higher molecular weight glycol ethers, glycerol esters and p-toluenesulphonic acid esters.

Fixing agents are based chemically on polyvinyl alkyl ethers, such as, for example, polyvinyl methyl ether or ketones, such as benzophenone or ethylenebenzophenone.

Possible solvents or diluents are, in particular, also water, if appropriate as a mixture with one or more of the above-mentioned organic chemical solvents or diluents, emulsifiers and dispersing agents.

Particularly effective preservation of wood is achieved by impregnation processes on a large industrial scale, for example vacuum, double vacuum or pressure processes.

The ready-to-use compositions can also comprise other insecticides, if appropriate, and also one or more fungicides, if appropriate.

Possible additional mixing partners are, preferably, the insecticides and fungicides mentioned in WO 94/29 268. The compounds mentioned in this document are an explicit constituent of the present application.

Especially preferred mixing partners which may be mentioned are insecticides, such as chlorpyriphos, phoxim, silafluofin, alphamethrin, cyfluthrin, cypermethrin, deltamethrin, permethrin, imidacloprid, NI-25, flufenoxuron, hexaflumuron and triflumuron, and also fungicides, such as epoxyconazole, hexaconazole, azaconazole, propiconazole, tebuconazole, cyproconazole, metconazole, imazalil, dichlorfluanid, tolylfluanid, 3-iodo-2-propinyl-butyl carbamate, N-octyl-isothiazolin-3-one and 4,5-dichloro-N-octylisothiazolin-3-one.

The preparation and the use of the active compounds according to the invention is illustrated by the examples below.

EXAMPLE I-1a-1

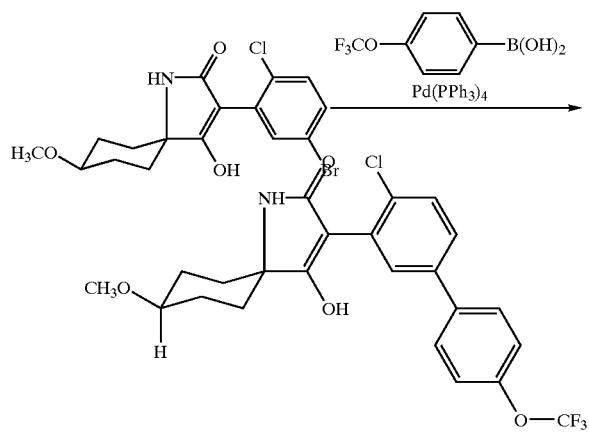

1.6 g of 4-trifluoromethoxyphenylboronic acid and 0.29 g of tetrakis(triphenylphosphile)palladium are added to 1.93 g of the bromine compound shown above in 20 ml of 1,2-dimethoxyethane at 20° C. The mixture is stirred for 15 minutes at 20° C., 15 ml of a 20% sodium carbonate solution are added and the mixture is stirred for one day at 80° C. The solution is filtered and extracted with ethyl acetate. The aqueous phase is acidified with concentrated hydrochloric acid at 0 to 10° C., concentrated to dryness in vacuo and the residue is chromatographed on silica gel using methylene chloride/ethyl acetate (3:1) as the mobile solvent.

Yield: 0.40 g (17% of theory); m.p.: 143° C.

EXAMPLE I-1a-14

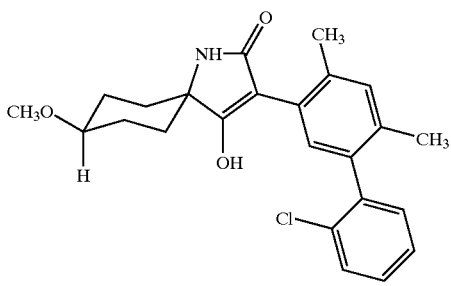

4.42 g of the compound according to Example (II-10) in 9 ml of absolute dimethyl formamide (DMF) are added dropwise to 2.6 g of potassium tert.-butylate in 7 ml of absolute DMF at 80° C. and the mixture is stirred at this temperature until the reaction is complete (as monitored by thin-layer chromatography (TLC)). After cooling, 90 ml of ice water are added and the mixture is acidified at 0° C. to 10° C. with concentrated hydrochloric acid to a pH of 2. The mixture is filtered off, washed with ice water, dried and boiled out with methyl-tert.-butyl ether (MTBE)/n-hexane.

Yield: 2.81 g (68% of theory), m.p: 204° C.

By the methods of Examples I-1-a-1 and I-1-a-14, and in accordance with the general procedures for preparing compounds of the formula I-1-a, the following compounds were prepared:

At reflux, 0.4 ml of isobutyryl chloride is added to 1 g of the compound of Example (I-1-a-16) and 0.5 ml of triethylamine in 30 ml of ethyl acetate (EA), and the mixture is stirred until the reaction has ended (monitored by TLC). The mixture is concentrated and purified by silica gel chromatography.

Mobile phase methylene chloride/EA 10/1

Yield 0.15 g (11% of theory), m.p.: 201° C.

By the method of Example (I-1-b-1), and in accordance until the general procedures for preparing compounds of the formula (I-1-b), the following compounds were prepared:

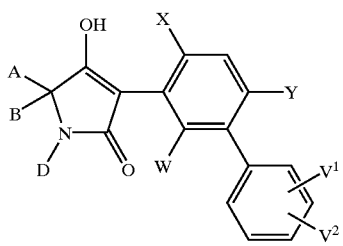

| Ex. No. | W | S | Y | V¹ | V² | D | A | B | m.p. (° C.) | Isomer |
|---|---|---|---|---|---|---|---|---|---|---|
| I-1-a-2* | CH₃ | CH₃ | H | H | H | H | — | —(CH₂)₂—CHCH₃—(CH₂)₂— | >240 | β |
| I-1-a-3* | CH₃ | CH₃ | H | 4-Cl | H | H | — | —(CH₂)₂—CHCH₃—(CH₂)₂— | >240 | β |
| I-1-a-4* | CH₃ | OCH₃ | H | 4-Cl | H | H | — | —(CH₂)₂—CHOCH₃—(CH₂)₂— | >240 | β |
| I-1-a-5* | CH₃ | CH₃ | CH₃ | 4-Cl | H | H | — | —(CH₂)₂—CHOCH₃—(CH₂)₂— | >240 | β |
| I-1-a-6* | CH₃ | CH₃ | CH₃ | H | H | H | — | —(CH₂)₂—CHOCH₃—(CH₂)₂— | >240 | β |
| I-1-a-7* | CH₃ | CH₃ | H | 4-Cl | H | H | — | —CH₂—O—(CH₂)₃— | >250 | — |
| I-1-a-8* | CH₃ | CH₃ | H | H | H | H | — | —CH₂—O—(CH₂)₃— | >240 | — |
| I-1-a-9* | H | Cl | H | 4-Cl | H | H | — | —(CH₂)₂—CHOCH₃—(CH₂)₂— | >240 | β |
| I-1-a-10* | H | Cl | H | H | H | H | — | —(CH₂)₂—CHOCH₃—(CH₂)₂— | >240 | β |
| I-1-a-11* | H | CH₃ | CH₃ | H | H | H | — | —(CH₂)₂—CHOCH₂H₅—(CH₂)₂— | >240 | β |
| I-1-a-12* | H | Cl | OCH₃ | 4-Cl | H | H | — | —(CH₂)₂—CHOCH₃—(CH₂)₂— | >240 | β |
| I-1-a-13* | H | Cl | OCH₃ | H | H | H | — | —(CH₂)₂—CHOCH₃—(CH₂)₂— | 134 | β |
| I-1-a-14 | H | CH₃ | CH₃ | 2-Cl | H | H | — | —(CH₂)₂—CHOCH₃—(CH₂)₂— | 204 | β |
| I-1-a-15 | CH₃ | CH₃ | H | 4-Cl | H | H | — | —(CH₂)₂—O—(CH₂)₂— | 156 | — |
| I-1-a-16* | H | CH₃ | H | 4-Cl | H | H | — | —(CH₂)₂—CHOCH₃—(CH2)₂— | 185 | β |
| I-1-a-17 | H | CH₃ | H | 4-Cl | H | H | — | —CH₂—CHCH₃—O—(CH₂)₂— | >245 | β |
| I-1-a-18 | H | CH₃ | H | 4-Cl | H | H | —CH₃ | CH₃ | 222 | — |
| I-1-a-19 | CH₃ | CH₃ | H | 4-Cl | H | H | — | —CH₂—CHCH₃—O—(CH₂)₂ | 185 | β |
| I-1-a-20 | CH₃ | CH₃ | H | 4-Cl | H | H | — | —(CH₂)₂—O—(CH₂)₂— | >250 | — |
| I-1-a-21 | H | CH₃ | H | 4-Cl | H | H | — | —CH₂—O—(CH₂)₃— | >240 | — |
| I-1-a-22 | H | CH₃ | H | 4-Cl | H | H | — | —(CH₂)₂—O—(CH₂)₂— | >240 | — |
| I-1-a-23 | H | CH₃ | CH₃ | 4-Cl | H | H | — | —CH₂—CHCH₃—O—(CH₂)₂— | 208 | β |
| I-1-a-24 | H | C₂H₅ | H | 4-Cl | H | H | — | —(CH₂)₂—CHOCH₃—(CH₂)₂— | 138 | β |
| I-1-a-25 | H | CH₃ | CH₃ | 4-Cl | H | H | — | —(CH₂)₂—CHOCH₃—(CH₂)₂— | 238 | β |
| I-1-a-26 | H | CH₃ | CH₃ | 4-Cl | H | H | — | —(CH₂)₂—O—(CH₂)₂ | >250 | — |
| I-1-a-27 | H | CH₃ | CH₃ | 4-Cl | H | H | — | —CH₂—O—(CH₂)₃— | >235 | — |

*prepared via Suzuki coupling by the method of Ex. I-1-a-1

EXAMPLE I-1-b-1

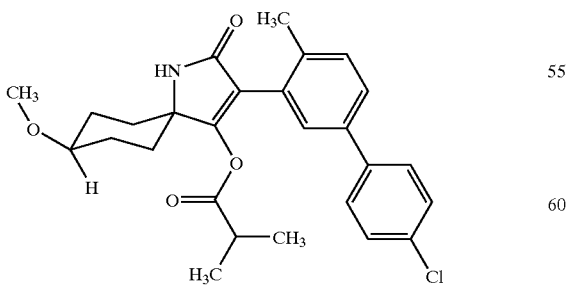

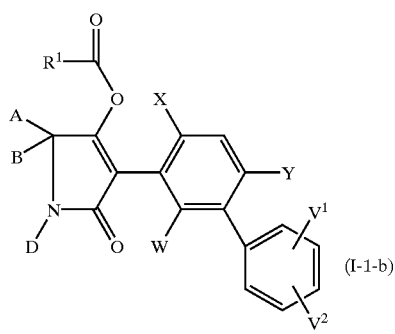

(I-1-b)

| Ex. No. | W | X | Y | V¹ | V² | D | A | B | R¹ | m.p. (° C.) | Isomer |
|---|---|---|---|---|---|---|---|---|---|---|---|
| I-1-b-2 | H | CH₃ | H | 4-Cl | H | H | CH₂—CHCH₃—O—(CH₂)₂— | | i-C₃H₇ | >230 | β |

EXAMPLE I-1-c-1

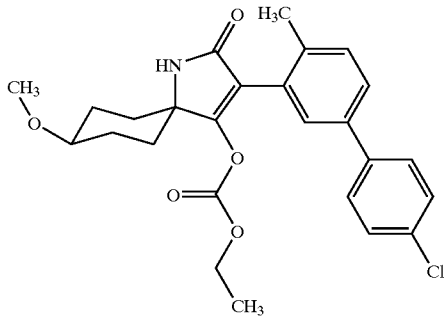

At 0° C., 0.35 g of ethyl chloroformate is added to 1 g of the compound of Example (I-1-a-16) and 0.5 ml of triethylamine in 30 ml of methylene chloride, and the mixture is stirred at 20° C. for one day. The mixture is concentrated and the residue is purified by silica gel chromatography.

Mobile phases methylene chloride/EA 10/1

Yield 0.12 g, m.p.: 194° C.

By the method of Example (I-1-c-1), and in accordance with the general procedures for preparing compounds of the formula (I-1-c), the following compounds were prepared:

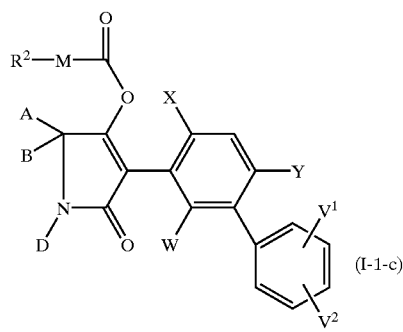

(I-1-c)

| Ex. No. | W | X | Y | V¹ | V² | D | A | B | M | R² | m.p. (° C.) | Isomer |
|---|---|---|---|---|---|---|---|---|---|---|---|---|
| I-1-c-2 | H | CH₃ | H | Cl | H | H | —CH₂—CHCH₃—O—(CH₂)₂— | | O | C₂H₅ | 187 | β |
| I-1-c-3 | H | CH₃ | H | Cl | H | H | —CH₂—O—(CH₂)₃— | | O | C₂H₅ | >240 | — |
| I-1-c-4 | H | CH₃ | H | Cl | H | H | —(CH₂)₂—CHOCH₃—(CH₂)₂— | | O | i-C₄H₉ | 168 | β |
| I-1-c-5 | H | CH₃ | H | Cl | H | H | CH₃ | CH₃ | O | C₂H₅ | 149 | — |

EXAMPLE II-1

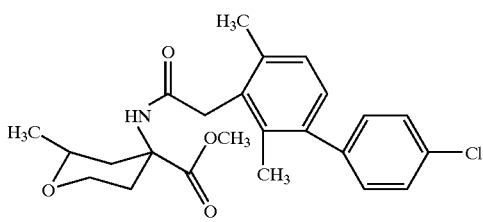

5 g of the compound of Example (XXVII-5) and 7.6 ml of thionyl chloride are heated at 80° C. until evolution of gas has ceased. Excess thionyl chloride is removed and the residue is taken up in 20 ml of acetonitrile (solution 1).

4.61 g of the compound

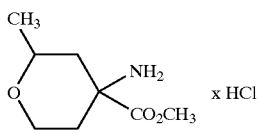

are initially charged in 20 ml of acetonitrile, 6.1 g of ground potassium carbonate are added, solution 1 is added dropwise at 0–10° C. and the mixture is stirred at room temperature for 1 hour. The mixture is poured into 250 ml of ice-water and extracted with methylene chloride, and the extract is washed with 0.5N HCl and concentrated. The residue is chromatographed over silica gel (mobile phase methylene chloride/EA 3/1), yield 5 g, m.p.: 91° C.

By the method of Example II-1, and in accordance with the general procedures for preparing the compounds of the formula (II), the following examples of the formula (II) are obtained

EXAMPLE (I-2-a-1)

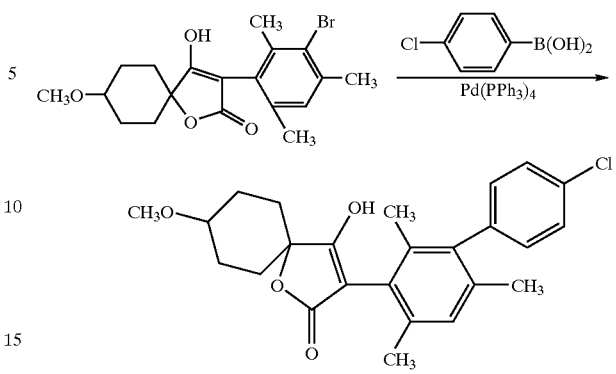

19.5 ml of 20% strength sodium carbonate solution are added, to 1.55 g of the bromine compound shown above, obtainable in accordance with the examples of WO 97/36868, 0.73 g of 4-chlorophenylboronic acid and 0.27 g of tetrakis(triphenylphosphine)palladium in 20 ml of dimethoxyethane, and the mixture is stirred at 80° C. for 4 hours. The mixture is admixed with 1 N NaOH and extracted twice with ether. The alkaline phase is filtered and acidified using dilute hydrochloric acid. The mixture is filtered off with suction and dried. Yield 0.36 g, m.p. 260–263° C.

By the method of Example I-2-a-1, and/or in accordance with the general procedures for preparing the compounds of the formula (I-2-a), the following examples of the formula (I-2-a) are obtained

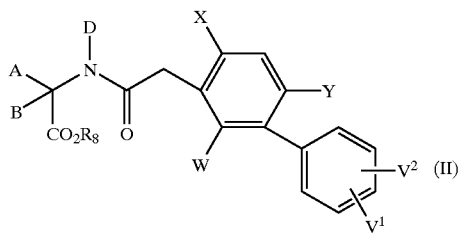

| Ex. No. | W | X | Y | $V^1$ | $V^2$ | D | A | B | $R^8$ | m.p. (° C.) | Isomer |
|---|---|---|---|---|---|---|---|---|---|---|---|
| II-2 | H | $CH_3$ | H | 4-Cl | H | H | —$CH_2$—O—$(CH_2)_2$— | | $CH_3$ | 125 | — |
| II-3 | H | $CH_3$ | $CH_3$ | 4-Cl | H | H | —$CH_2$—$CHCH_3$—O—$(CH_2)_2$— | | $CH_3$ | 76 | β |
| II-4 | H | $CH_3$ | H | 4-Cl | H | H | —$(CH_2)_2$—O—$(CH_2)_2$— | | $CH_3$ | 179 | — |
| II-5 | $CH_3$ | $CH_3$ | $CH_3$ | 4-Cl | H | H | —$(CH_2)_2$—$CHOCH_3$—$(CH_2)_2$— | | $CH_3$ | 186 | β |
| II-6 | $CH_3$ | $CH_3$ | $CH_3$ | 4-Cl | H | H | —$CH_2$—O—$(CH_2)_3$— | | $CH_3$ | 169 | — |
| II-7 | $CH_3$ | $CH_3$ | $CH_3$ | 4-Cl | H | H | —$(CH_2)_2$—$CHOC_2H_5$—$(CH_2)_2$— | | $CH_3$ | 194 | β |
| II-8 | $CH_3$ | $CH_3$ | H | 4-Cl | H | H | —$CH_2$—O—$(CH_2)_3$— | | $CH_3$ | 123 | — |
| II-9 | H | $CH_2H_5$ | H | 4-Cl | H | H | —$(CH_2)_2$—$CHOCH_3$—$(CH_2)_2$— | | $CH_3$ | 109 | β |
| II-10 | H | $CH_3$ | $CH_3$ | 2-Cl | H | H | —$(CH_2)_2$—$CHOCH_3$—$(CH_2)_2$— | | $CH_3$ | 121 | β |
| II-11 | $CH_3$ | $CH_3$ | H | 4-Cl | H | H | —$(CH_2)_2$—O—$(CH_2)_2$— | | $CH_3$ | 165 | — |
| II-12 | H | $CH_3$ | H | 4-Cl | H | H | —$(CH_2)_2$—$CHOCH_3$—$(CH_2)_2$— | | $CH_3$ | 139 | β |
| II-13 | H | $CH_3$ | H | 4-Cl | H | H | —$(CH_2)_2$—O—$(CH_2)_2$— | | $CH_3$ | 185 | — |
| II-14 | H | $CH_3$ | H | 4-Cl | H | H | —$CH_2$—$CHCH_3$—O—$(CH_2)_2$— | | $CH_3$ | 145 | β |
| II-15 | H | $CH_3$ | H | 4-Cl | H | H | $CH_3$ | $CH_3$ | $CH_3$ | 154 | — |
| II-16 | H | $CH_3$ | $CH_3$ | 4-Cl | H | H | —$(CH_2)_2$—$CHOCH_3$—$(CH_2)_2$— | | $CH_3$ | 76 | β |
| II-17 | H | $CH_3$ | $CH_3$ | 4-Cl | H | H | —$(CH_2)_2$—O—$(CH_2)_2$— | | $CH_3$ | 137 | — |
| II-18 | H | $CH_3$ | $CH_3$ | 4-Cl | H | H | —$CH_2$—O—$(CH_2)_3$— | | $CH_3$ | 166 | — |

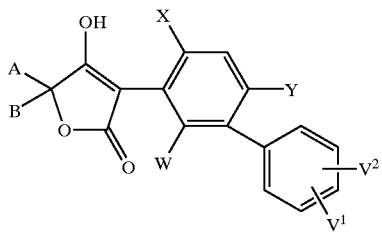

(I-2-a)

| Ex. No. | W | X | Y | V¹ | V² | A | B | m.p. (° C.) |
|---|---|---|---|---|---|---|---|---|
| I-2-a-2 | CH₃ | CH₃ | H | 4-Cl | H | —(CH₂)₂—CHOCH₃—(CH₂)₂— | | 243–245 |
| I-2-a-3 | H | Cl | H | 4-Cl | H | —(CH₂)₂—CHOCH₃—(CH₂)₂— | | 1) |

1) $^1$H NMR (300 MHz, d₆-DMSO): δ = 3.27, 3.29 (2s, 3H, OC$\underline{H}_3$), 7.51–7.71 (m, 7H, Ar $\underline{H}$) 12.6 (brd, 1H, OH).

EXAMPLE I-2-b-1

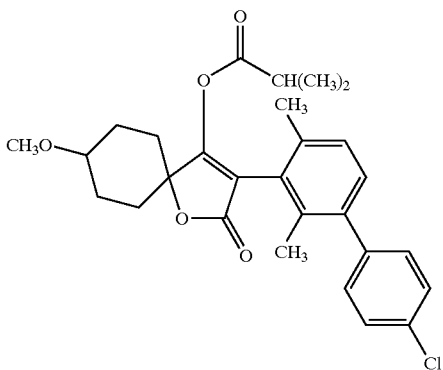

0.125 g (0.3 mmol) of the compound I-2-a-2 is initially charged in absolute methylene chloride and then admixed with 0.04 g (0.36 mmol) of triethylamine, and 0.04 g (0.36 mmol) of isobutyryl chloride is added dropwise at 0–10° C. The mixture is stirred overnight and subsequently washed once with 10% strength citric acid and once with 10% strength aqueous sodium carbonate solution, and the organic phase is dried and concentrated.

Yield: 0.1 g of an oil $^1$H NMR (300 MHz, CDCl₃): δ=2.06, 2.07 (2s, 3H, Ar CH₃), 2.24, 2.25 (2s, 3H, Ar CH₃), 2.61 (m, 1H, C$\underline{H}$(CH₃)₂), 3.35, 3.40 (2s, 3H, OCH₃), 7.09 (s, 2H, ArH), 7.16, 7.19 (AA', BB', 1H, Ar—H), 7.35, 7.37 (AA', BB', 2H, ArH).

EXAMPLE I-2-c-1

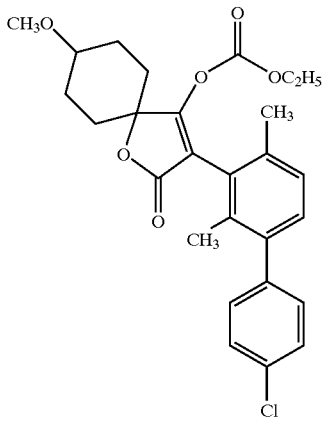

Preparation by the method of Example I-2-b-1 by reacting the compound of Example I-2-a-2 with ethyl chloroformate. Oil.

$^1$H NMR (300 MHz, CDCl₃): δ=1.10, (t, 3H, O—CH₂CH₃), 2.08, (2s, 3H, Ar CH₃), 2.24, 2.25 (2s, 3H, Ar C$\underline{H}_3$), 3.36, 3.40 (2s, 3H, OCH₃), 7.11 (2s, 2H, ArH), 7.18 7.21 (AA', BB', 2H, ArH), 7.35, 7.38 (AA', BB', 2H, ArH).

EXAMPLE I-3-a-1

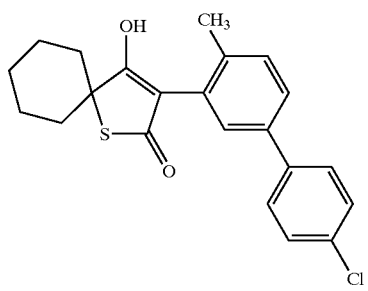

44 g of the compound of Example IV-1 and 92 ml of trifluoroacetic acid in 210 ml of toluene are heated under reflux overnight. The mixture is concentrated and the residue is taken up in 600 ml of water and 200 ml of MTBE. The pH is adjusted to 14 by addition of NaOH, and the mixture is then extracted twice with MTBE. The aqueous phase is added dropwise to 1 l of HCl. The mixture is stirred for 2 hours, extracted with methylene chloride and concentrated. For purification, the residue is stirred with approximately 200 ml of MTBE/cyclohexane 8/1, filtered off with suction and dried. Yield 5.9 g, m.p. 232–235° C.

By the method of Example (I-3a-1) and/or in accordance with the general procedures for preparing, the compounds of the formula (I-3-a), the following, compounds are obtained (I-3-a)

| Ex. No. | W | X | Y | V¹ | V² | A | B | m.p. (° C.) |
|---|---|---|---|---|---|---|---|---|
| I-3-a-2 | H | CH | CH₃ | 4-Cl | H | —(CH₂)₅— | | 245–247 |
| I-3-a-3 | CH₃ | CH₃ | CH₃ | 4-Cl | H | —(CH₂)₅— | | 248–250 |

EXAMPLE I-3-b-1

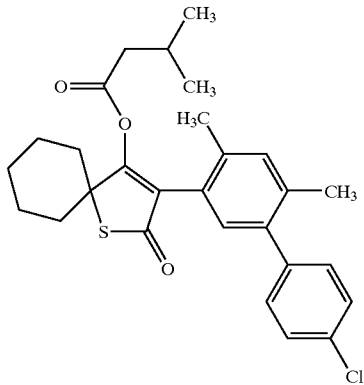

Preparation by the method of Example I-2-b-1, by reacting the compound of Example I-3-a-2 with isovaleryl chloride.

¹H NMR (400 MHz, d₆-DMSO): δ=0.9 (d, 6H, CH—C$\underline{H}_3$); 1.2–2.0 (m, 10H, cyclohexyl-H); 2.1, 2.2 (s, 6H, 2×ArCH₃); 6.85–7.5 (m, 6H, ArH) ppm.

EXAMPLE I-3-c-1

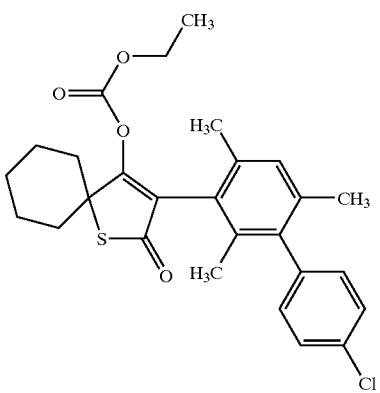

Preparation by the method of Example I-2c-1, by reaction of the compound of Example I-3-a-3 with ethyl chloroformate. Oil.

¹H NMR (400 MHz, d₆-DMSO): δ=0.95 (t, 3H, CH₂CH₃); 1.3–1.9 (m, 10H, cyclohexyl-H); 1.9 (s, 3H, ArCH₃); 2.1 (s, 6H, 2×Ar—CH₃); 4.0 (q, 2H, OCH₂); 7.0–7.5 (m, 5H, Ar—H) ppm.

By the method of Example (I-3-c-1), and/or in accordance with the general procedures for preparing the compounds of the formula (I-3-c), the following compounds are obtained (I-3-c)

| Ex. No. | W | X | Y | V¹ | V² | A | B | M | R² | m.p. (° C.) |
|---|---|---|---|---|---|---|---|---|---|---|
| I-3-c-2 | H | CH₃ | CH₃ | 4-Cl | H | —(CH₂)₅— | | O | C₂H₅ | oil |

EXAMPLE IV-1

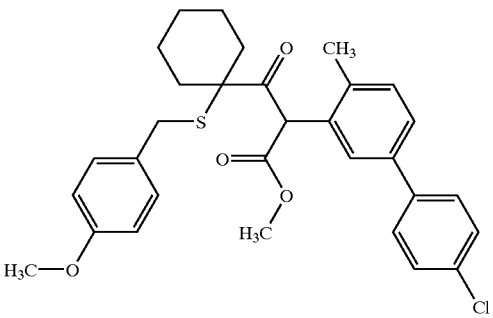

A: 15 g (53.5 mmol) of the compound

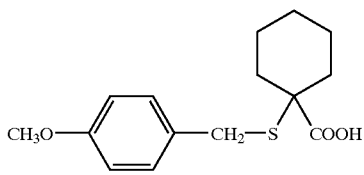

are converted into the corresponding acyl chloride in a customary manner using 9.63 g (80.3 mmol) of thionyl chloride, and dissolved in 30 ml of tetrahydrofuran (THF).

B: At 0° C., 27 g (87.5 mmol) of the compound of Example XXXII-2 are added dropwise to 45.8 ml (96.3 mmol, 1.1 eq) of lithium diisopropylamide (LDA) solution in 100 ml of THF, the mixture is stirred at this temperature for 30 minutes are the solution prepared under A is then added dropwise. Without cooling, stirring is continued for 1 hour. 300 ml of MTBE and a few drops of water are then added, and the mixture is washed twice with in each case 300 ml of 10% strength NH$_4$Cl solution and concentrated. Yield 44 g. Oil.

$^1$H NMR (400 MHz, d$_6$-DMSO): δ=1.2–2.0 (m, 10H, cyclohexyl-H); 2.25 (s, 3H, Ar—CH$_3$); 3.1 (dd, 2H, SCH$_2$); 3.6–3.7 (s, 6H, 2×OCH$_3$); 6.7–7.7 (m, 12H, Ar—H) ppm.

EXAMPLE I-7-a-1

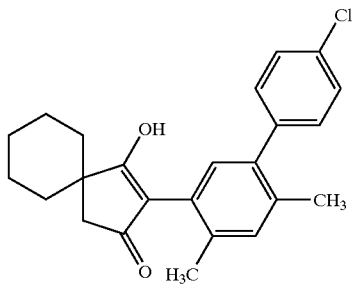

5.3 g (12.8 mmol) of the compound of Example X-1 are initially charged in 20 ml of DMF, admixed with 2.2 g (19.2 mmol, 1.5 eq) of potassium tert-butoxide and heated at 80° C. for 1 hour (monitored by TLC).

The mixture is then slowly added to approximately 0.6 l of 1 N HCl (with ice-cooling), filtered off with suction and dried. Yield 4.85 g, m.p. 224–226° C.

By the method of Example (I-7-a-1), and/or in accordance with the general procedures for preparing the compounds of the formula (I-7-a), the following compounds are obtained.

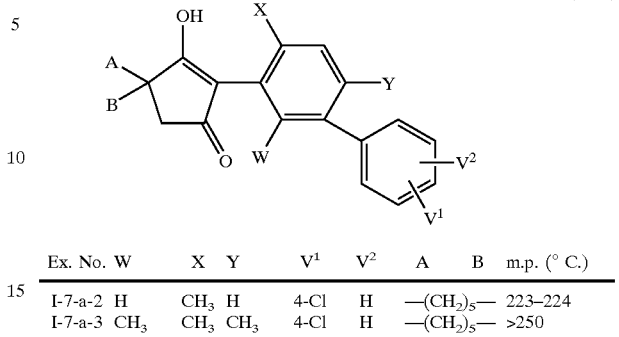

(I-7-a)

| Ex. No. | W | X | Y | V$^1$ | V$^2$ | A | B | m.p. (° C.) |
|---|---|---|---|---|---|---|---|---|
| I-7-a-2 | H | CH$_3$ | H | 4-Cl | H | —(CH$_2$)$_5$— | | 223–224 |
| I-7-a-3 | CH$_3$ | CH$_3$ | CH$_3$ | 4-Cl | H | —(CH$_2$)$_5$— | | >250 |

EXAMPLE I-7-b-1

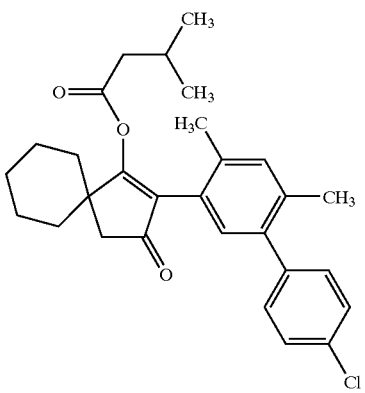

Preparation by the method of Example (I-2-b-1) by reacting the compound of Example (I-7-a-1) with isovalery chloride. Yield 1.26 g of an oil.

$^1$NMR (400 MHz, d$_6$-DMSO): δ=0.95 (d, 6H, 2×CH—CH3); 1.2–1.8 (m, 10H, cyclohexyl-H); 2.1, 2.2 (s, 6H, 2×Ar—CH$_3$); 6.8–7.5 (m, 6H, Ar—H) ppm.

EXAMPLE I-7-c-1

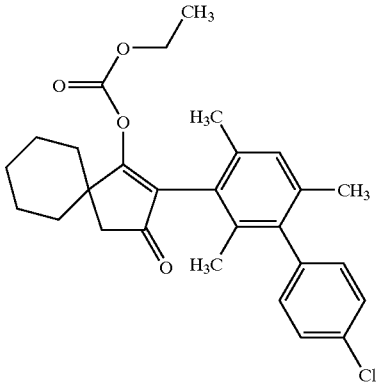

Preparation by the method of Example (I-2-c-1) by reacting the compound of Example (I-7-a-3) with ethyl chloroformate. Yield 1.3 g. Wax.

$^1$H NMR (400 MHz, d$_6$-DMSO): 1.2 (t, 3H, CH$_2$CH$_3$); 1.3–1.8 (m, 10H, cyclohexyl); 1.65, 1.9, 2.05 (s, 3×3H, Ar—CH$_3$); 3.05 (bs, 2H, cyclophenyl CH$_2$); 4.2 (q, 2H, OCH$_2$); 7.0–7.5 (m, 5H, Ar—H).

By the method of Example (I-7-c-1) and/or in accordance with the general procedures for preparing the compounds of the formula (I-7-c), the following compounds are obtained

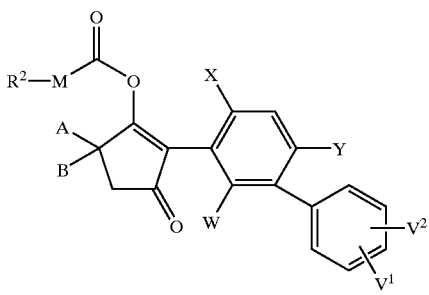

(I-7-c)

| Ex. No. | W | X | Y | V$^1$ | V$^2$ | A | B | M | R$^2$ | m.p. (° C.) |
|---|---|---|---|---|---|---|---|---|---|---|
| I-7-c-2 | H | CH$_3$ | CH$_3$ | 4-Cl | H | —(CH$_2$)$_2$— | | O | C$_2$H$_5$ | oil |

EXAMPLE X-1

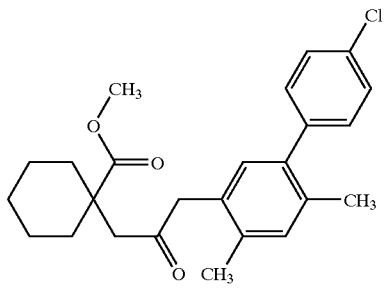

24 g of crude product of the compound of Example (XXXVIII-1) are heated under reflux in 140 ml of acetone with 8.2 g of potassium carbonate and 25.4 g of methyl iodide for 16 hours. The mixture is filtered and concentrated and the residue is purified over silica gel: mobile phase, methylene chloride/petroleum ether 2/1, finally pure methylene chloride. Yield 5.6 g.

$^1$H NMR (400 MHz, d$_6$-DMSO): δ=1.2–1.8 (m, 10H, cyclohexyl H); 2.1, 2.2 (s, 6H, 2×Ar—CH$_3$); 2.9, 3.8 (s, 4H, 2×COCH$_2$); 3.5 (s, 3H, OCH$_3$); 6.95–7.5 (s, 6H, Ar—H),

EXAMPLE XXXVIII-1

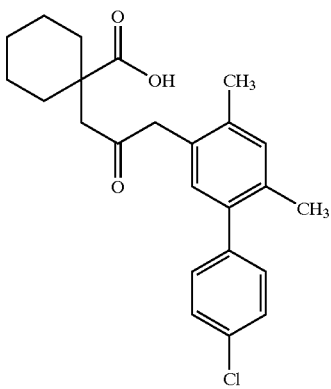

At −15° C., a solution of 17.9 g of the compound of Example XXXII-1 is added dropwise to a solution of 30 ml of LDA solution (2 M, 1.1 eq) in 60 ml of THF, and the mixture is stirred at 0° C. for 1 hour. At −15° C., a solution of 6.1 g of the compound of Example XLI-1 in 10 ml of THF is then added dropwise. The mixture is stirred at room temperature for 2 hours, 100 ml of water and 24 g of ammonium chloride are added and the mixture is acidified using conc. HCl. The intermediate is extracted with ether. The extract is concentrated and the residue is heated with 60 g of KOH in 220 ml of water for 2 days. After cooling, the mixture is acidified using conc. HCl and extracted with ether. The crude product is reacted further without any purification. Yield 24 g.

EXAMPLE XLI-1

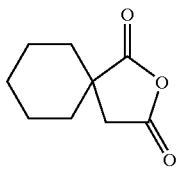

100 of the compound

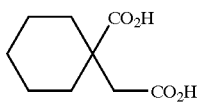

in 500 ml of acetic anhydride are heated under refluxed overnight. The mixture is concentrated, the residue is dissolved in a little methylene chloride and admixed with n-hexane. The mixture is left in a fridge overnight, filtered off with suction and dried. Yield 74.8 g.

EXAMPLE I-8-a-1

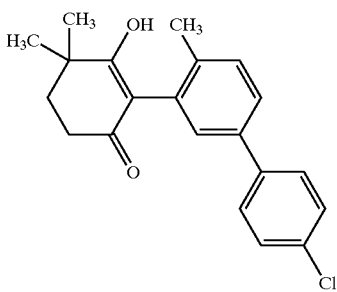

0.95 g of potassium tert-butoxide is added to 2.1 g of the compound of Example (XI-1) in 10 ml of DMF, and the mixture is heated at 80° C. for 2 hours. With ice-cooling, the mixture is slowly poured into approximately 1 of 1 N HCl, and the precipitate is filtered off suction.

$^1$H NMR, (400 MHz, $d_6$-DMSO): δ=1.1 (s, 6H, C—CH$_3$); 1.85 (m, 2H, COCH$_2$C$\underline{H}_2$); 2.0 (s, 3H, ArCH$_3$); 2.65 (m, 2H, COC$\underline{H}_2$CH$_2$); 7.1–7.6 (m, 7H, Ar—H) ppm.

By the method of Example I-8-a-1, and/or in accordance with the general procedures for preparing the compounds of the formula (I-8-a), the following compounds are obtained

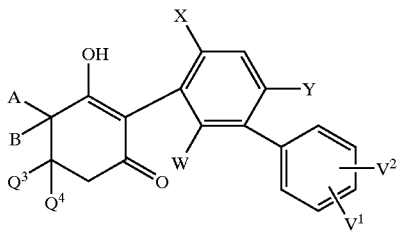

(I-8-a)

| Ex. No. | W | X | Y | V$^1$ | V$^2$ | A | B | Q$^3$ | Q$^4$ | m.p. (° C.) |
|---|---|---|---|---|---|---|---|---|---|---|
| I-8-a-2 | H | CH$_3$ | CH$_3$ | 4-Cl | H | H | H | CH$_3$ | CH$_3$ | 223–225 |
| I-8-a-3 | H | CH$_3$ | CH$_3$ | 4-Cl | H | CH$_3$ | CH$_3$ | H | H | resin |
| I-8-a-4 | H | CH$_3$ | H | 4-Cl | H | H | H | CH$_3$ | CH$_3$ | resin |
| I-8-a-5 | CH$_3$ | CH$_3$ | CH$_3$ | 4-Cl | H | H | H | CH$_3$ | CH$_3$ | >250 |

EXAMPLE I-8-b-1

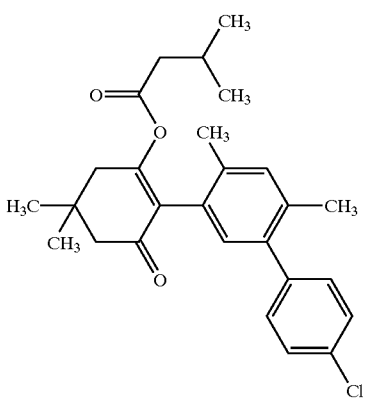

Preparation by the method of Example (I-2-b-1), by reacting the compound of Example l-8-a-2 with isovaleryl chloride. Oil. $^1$-H NMR (400 MHz, $d_6$-DMSO): 1.1 (δ, 6H, 2×CHC$\underline{H}_3$); 1.1 (s, 6H, 2×CCH$_3$); 1.65 (m, 1H, C$\underline{H}$CH$_3$); 2.0, 2.2 (s, 6H, ArCH$_3$); 6.7–7.5 (m, 6H, Ar—H) ppm.

EXAMPLE I-8-c-1

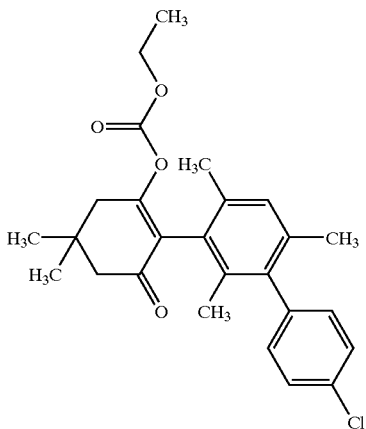

Preparation by the method of Example (I-2-c-1) by reacting the compound of (I-8-a-5) with ethyl chloroformate.

$^1$H NMR (400 MHz, $d_6$-DMSO): δ=1.1 (t,3H, CH$_2$C$\underline{H}_3$); 1.14 1.18 (s,2×3H, C—CH$_3$); 1.9 2.0 2.1 (s, 3×3H, ArCH$_3$); 2.45 2.7 (d,2×2H, cyclohexyl-CH$_2$); 4.1 (q,2H, OCH$_2$); 7.0–7.5 (m,5H, Ar—H) ppm.

By the method of Example (I-8-c-1), and/or in accordance with the general procedures for preparing the compounds of the formula (I-8-c), the following compounds are obtained

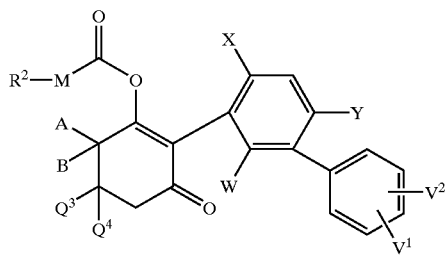

(I-8-c)

| Ex. No. | W | X | Y | V¹ | V² | A | B | Q³ | Q⁴ | M | R² | m.p. (° C.) |
|---|---|---|---|---|---|---|---|---|---|---|---|---|
| I-8-c-2 | H | CH$_3$ | CH$_3$ | 4-Cl | H | H | H | CH$_3$ | CH$_3$ | O | C$_2$H$_5$ | oil |

EXAMPLE XI-1

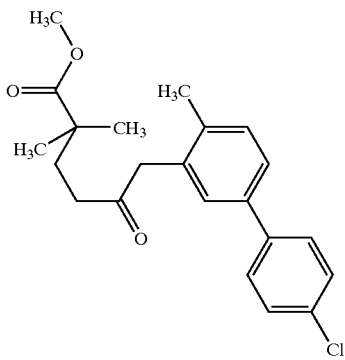

38.2 g of the compound of Example XLII-1, 14.6 g of potassium carbonate and 45.25 g of methyl iodide 250 ml of acetone are heated under reflux for 16 hours. The mixture is filtered, the filtrate is concentrated and the residue is purified over silica gel (mobile phase methylene chloride/petroleum ether 2/1, finally pure methylene chloride). Yield 2.1 g of an oil.

$^1$H NMR (400 MHz, d$_6$-DMSO): 1.1 (s, 6H, 2×CCH$_3$); 1.7 (m, 2H, COCH$_2$CH$_2$); 2.15 (s, 3H, ArCH$_3$); 2.55 (m, 2H, COCH$_2$CH$_2$); 3.55 (s, 3H, OCH$_3$); 7.2–7.7 (m, 7H, Ar—H) ppm.

EXAMPLE XLII-1

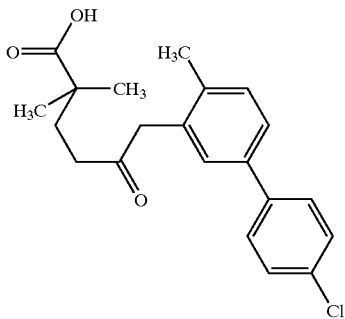

At −15° C., a solution of 34 g of the compound of Example XXXII-2 in 30 ml of THF is added dropwise to a solution of 60 ml of LDA solution (2 molar, 1.1 eq) in 120 ml of THF, and the mixture is stirred at 0° C. for 1 hour. At −15° C., a solution of 10.3 g of 2,2-dimethylglutaric anhydride in 20 ml of THF is then added dropwise. The mixture is stirred at room temperature for 2 hours, 180 ml of water and 48 g of ammonium chloride are then added, the mixture is acidified using concentrated HCl and the intermediate is extracted with ether. The ether is removed and the residue is heated under reflux with 120 ml of KOH in 400 ml of water for 2 days.

After cooling, the mixture is acidified using concentrated HCl and extracted with ether. The crude product which remains after the ether has been removed is reacted further without any purification. Yield 38.4 g of an oil.

EXAMPLE XXIV-1

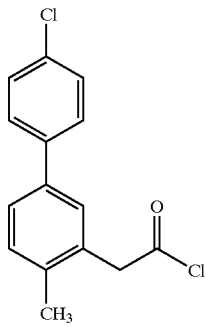

65.2 g of the compound of Example XXVII-2 in 55 ml of thionyl chloride are heated at 70° C. until evolution of gas has ceased. Excess thionyl chloride is removed and the residue is distilled under high vacuum. Yield: 32 g, m.p. 46° C.

By the method of Example (XXIV-1) and/or in accordance with the general procedures for preparing compounds of the formula (XXIV), the following compounds of the formula (XXIV) are obtained (XXIV)

| Ex. No. | W | X | Y | V$^1$ | V$^2$ | m.p. (° C.) |
|---|---|---|---|---|---|---|
| XXIV-2 | H | CH$_3$ | H | 4-Cl | H | * |
| XXIV-3 | CH$_3$ | CH$_3$ | CH$_3$ | 4-Cl | H | * |
| XXIV-4 | H | CH$_3$ | CH$_3$ | 2-Cl | H | * |

* The compounds were employed without any further purification for preparing compounds of the formula (II) or (III).

EXAMPLE XXVII-1

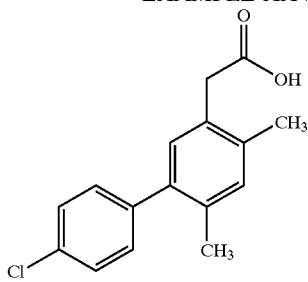

3.04 g of LiOH in 280 ml of water are added dropwise to 35 g of the compound of Ex. XXXII-1 ml 280 ml of THF, 10 ml of ethanol are added and the mixture is stirred at room temperature overnight. The mixture is then concentrated, the residue is admixed with water and extracted with MTBE. The aqueous phase is acidified using concentrated HCl. The mixture is filtered off with suction and the filter residue is washed with hexane. Yield: 21 g, m.p. 133° C.

By the method of Example (XXVII-1), and/or in accordance with the general procedures for preparing compounds of the formula (XXVII), the following compounds of the formula (XXVII) are obtained.

EXAMPLE XXXII-1

Variant A 54 g of the compound of Example XLV-1 are added to 31 g of KOH in 1 l of methanol, and the mixture is stirred at room temperature overnight. The mixture is filtered off with suction and the filter residue is washed with methanol. The filtrate is concentrated, and the residue is admixed with water and extracted with methylene chloride. The organic phase is concentrated. Yield 10 g.

Variant B 96 g of methyl 3-bromo-4,6-dimethylphenylacetate, 65 g of 4-chlorophenylboronic acid and 1.5 g of bis (triphenylphosphine)palladium(II) chloride in 1 of dimethoxyethane and 700 ml of 1 M Na$_2$CO$_3$ solution are heated under reflux overnight. The mixture is partitioned between water and EA, and the organic phase is washed with saturated ammonium chloride solution, water and saturated sodium chloride solution and concentrated. Yield 61 g.

$^1$H NMR (400 MHz, CDCl$_3$): δ=2.21, 2.31 (2s, 6H, Ar—CH$_3$); 3.63 (s, 2H, CH$_2$); 3.69 (s, 3H, OCH$_3$); 7.03–7.1 (2s, 2H, Ar—H); 7.25, 7.38 (AA', BB', 4H, Ar—H) ppm.

By the method of Example (XXXII-1), variant B, and/or in accordance with the general procedures for preparing compounds of the formula (XXXII), the following compounds of the formula (XXXII) are obtained (XXVII)

| Ex. No. | W | X | Y | V$^1$ | V$^2$ | m.p. ° C. |
|---|---|---|---|---|---|---|
| XXVII-2 | H | CH$_3$ | H | 4-Cl | H | 137 |
| XXVII-3 | CH$_3$ | CH$_3$ | CH$_3$ | 4-Cl | H | 138 |
| XXVII-4 | H | CH$_3$ | CH$_3$ | 2-Cl | H | 134 |
| XXVII-5 | CH$_3$ | CH$_3$ | H | 4-Cl | H | 153 |

(XXXII)

| Ex. No. | W | X | Y | V$^1$ | V$^2$ | R$^8$ | m.p. ° C. |
|---|---|---|---|---|---|---|---|
| XXXII-2 | H | CH$_3$ | H | 4-Cl | H | CH$_3$ | oil |
| XXXII-3 | CH$_3$ | CH$_3$ | CH$_3$ | 4-Cl | H | CH$_3$ | 68 |
| XXXII-4 | H | CH$_3$ | CH$_3$ | 2-Cl | H | CH$_3$ | oil |
| XXXII-5 | CH$_3$ | CH$_3$ | H | 4-Cl | H | CH$_3$ | oil |

EXAMPLE XLV-1

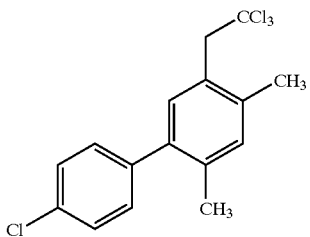

29.5 g of anhydrous copper(II) chloride are introduced into a solution of 33 g of isopentyl nitrite in 120 ml of acetonitrile. The mixture is admixed with 271 g of dichloroethane (vinylidene chloride) and subsequently with 43 g of the compound of Example XLVI-1 dissolved in acetonitrile, and the mixture is stirred at room temperature until evolution of gas has ceased. The mixture is then poured into 800 ml of ice-cooled 20% strength hydrochloric acid and extracted repeatedly with MTBE. The organic phase is washed with 20% strength HCl and concentrated.

Yield 19 g. The product was directly reacted further, without any purification.

EXAMPLE XLVI-1

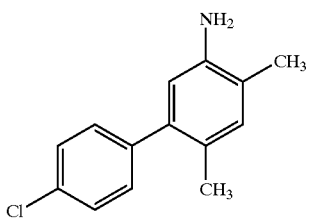

is obtained starting from 3-bromo-4,6-dimethylaniline and 4-chlorophenylboronic acid by Suzuki coupling, which is carried out as in Example XXXII-1, variant B.

Yield 12 g.

$^1$H NMR (400 MHz, CDCl$_3$): δ=2.12 (s, 3H, Ar—C$\underline{H}_3$), 2.18 (s, 3H, Ar—C$\underline{H}_3$), 3.35 (brd, 2H, NH$_2$), 6.53 (s, 1H, Ar—H), 6.94 (s, 1H, Ar—H), 7.23 (AA',BB', 2H, Ar—H), 7.35 (AA',BB', 2H, Ar—H).

EXAMPLE XLVI-1

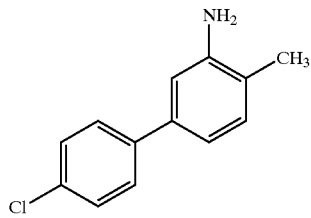

is obtained by the same method starting from 3-bromo-6-methylaniline. M.p. 184° C.

EXAMPLE

Myzus Test

Solvent: 1 part by weight of dimethylformamide
Emulsifier: 1 part by weight of alkylaryl polyglycol ether To produce a suitable preparation of active compound, 1 part by weigh of active compound is mixed with the stated amounts of solvent and emulsifier, and the concentrate is diluted with water to the desired concentration.

Cabbage leaves (*Brassica oleracea*) which are heavily infested by peach aphids (*Myzus persicae*) are treated by being dipped into the preparation of active compound of the desired concentration.

After the desired period of time, the kill in % is determined. 100% means that all aphids have been killed; 0% means that none of the aphids have been killed.

In this test, for example, the following compound of the Preparation Examples shows good efficacy:

TABLE

| | plant-damaging insects |  |
| --- | --- | --- |
| | Myzus test | |
| Active compounds | Concentration of active compound in % | Degree of kill in % after 6 days |

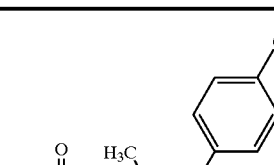

Ex. I-1-a-3    0.1    98

TABLE-continued plant-damaging insects
Myzus test

| Active compounds | Concentration of active compound in % | Degree of kill in % after 6 days |
|---|---|---|
| Ex. I-1-a-2 | 0.1 | 95 |
| Ex. I-1-a-6 | 0.1 | 100 |
| Ex. I-1-a-7 | 0.1 | 98 |

EXAMPLE

*Phaedon larvae* Test

Solvent: 7 parts by weight of dimethylformamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration.

Cabbage leaves (*Brassica oleracea*) are treated by being dipped into the preparation of active compound of the desired concentration and populated with larvae of the mustard beetle (*Phaedon cochleariae*) while the leaves are still moist After the desired period of time, the kill in % is determined. 100% means that all beetle larvae have been killed; 0% means that none of the beetle larvae have been killed.

In this test, for example, the following compounds of the Preparation Examples show good efficacy:

TABLE plant-damaging insects

*Phaedon larvae* test

| Active compound | Concentration of active compound in % | Degree of kill in % after 7 days |
|---|---|---|
| Ex. I-1-a-3 | 0.1 | 100 |
| Ex. I-1-a-2 | 0.1 | 100 |
| Ex. I-1-a-5 | 0.1 | 100 |
| Ex. I-1-a-6 | 0.1 | 100 |

TABLE-continued plant-damaging insects
*Phaedon larvae* test

| Active compound | Concentration of active compound in % | Degree of kill in % after 7 days |
| --- | --- | --- |
| Ex. I-1-a-7 | 0.1 | 100 |
| Ex. I-1-a-13 | 0.1 | 100 |

EXAMPLE

*Spodoptera frugiperda* Test

Solvent: 7 parts by weight of dimethylformamide

Emulsifier: 1 part by weight of alkylaryl polyglycol ether

To produce a suitable preparation of active compound, 1 part by weight of active compound is mixed with the stated amounts of solvent and emulsifier, and the concentrate is diluted with water to the desired concentration.

Cabbage leaves (*Brassica oleracea*) are treated by being dipped into the preparation of active compound of the desired concentration and are populated with caterpillars of the army worm (*Spodoptera frugiperda*) while the leaves are still moist.

After the desired period of time, the kill in % is determined. 100% means that all caterpillars have been killed; 0% means that none of the caterpillars have been killed.

In this test, for example, the following compounds of the Preparation Examples show good efficacy:

TABLE plant-damaging insects
*Spodoptera frugiperda* test

| Active compound | Concentration of active compound in % | Degree of kill in % after 7 days |
| --- | --- | --- |
| Ex. I-1-a-3 | 0.1 | 100 |

TABLE-continued plant-damaging insects
*Spodoptera frugiperda* test

| Active compound | Concentration of active compound in % | Degree of kill in % after 7 days |
|---|---|---|
| Ex. I-1-a-5 | 0.1 | 100 |
| Ex. I-1-a-6 | 0.1 | 100 |
| Ex. I-1-a-7 | 0.1 | 100 |

EXAMPLE

Tetranychus Test (OP-resistant/dip Treatment)

Solvent: 7 parts by weight of dimethylformamide

Emulsifier: 1 part by weight of alkylaryl polyglycol ether

To produce a suitable preparation of active compound, 1 part by weight of active compound is mixed with the stated amounts of solvent and emulsifier, and the concentrate is diluted with water to the desired concentration.

Bean plants (*Phaseolus vulgaris*) which are heavily infested by all stages of the greenhouse red spidermite (*Tetranychus urticae*) are dipped into a preparation of active compound of the desired concentration.

After the desired period of time, the effect in % is determined. 100% means that all spidermites have been killed; 0% means that none of the spidermites have been killed.

In this test, for example, the following compounds of the Preparation Examples show good efficacy:

TABLE plant-damaging insects
Tetranychus test (OP-resistant/dip treatment)

| Active compound | Concentration of active compound in % | Degree of kill in % after 7 days |
|---|---|---|
| Ex. I-1-a-3 | 0.1 | 100 |

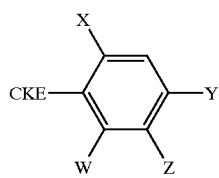

What is claimed is:

1. A compound of the formula (I)

$$\text{(I)}$$

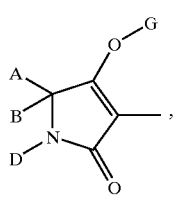

in which

X represents halogen, alkyl, alkoxy, alkenyloxy, alkylthio, alkylsulphinyl, alkylsulphonyl, halogenoalkyl, halogenoalkoxy, halogenoalkenyloxy, nitro, cyano or in each case optionally substituted phenyl, phenoxy, phenylthio, phenylalkoxy or phenylalkylthio, Z represents in each case optionally substituted cycloalkyl, aryl or hetaryl, W and Y independently of one another each represent hydrogen, halogen, alkyl, alkoxy, alkenyloxy, halogenoalkyl, halogenoalkoxy, halogenoalkenyloxy, nitro or cyano, CKE represents $$\text{(1)}$$

in which

A represents hydrogen, in each case optionally halogen-substituted alkyl, alkenyl, alkoxyalkyl, polyalkoxyalkyl, alkyl-thioalkyl, saturated or unsaturated, optionally substituted cycloalkyl in which optionally at least one ring atom is replaced by a heteroatom, or in each case optionally halogen-, alkyl-, halogenoalkyl-, alkoxy-, halogenoalkoxy-, cyano- or nitro-substituted aryl, arylalkyl or hetaryl, B represents hydrogen, alkyl or alkoxyalkyl, or A and B together with the carbon atom to which they are attached represent a saturated or unsaturated unsubstituted or substituted cycle which optionally contains at least one heteroatom, D represents hydrogen or an optionally substituted radical selected from the series consisting of alkyl, alkenyl, alkinyl, alkoxyalkyl, polyalkoxyalkyl, alkylthioalkyl, saturated or unsaturated cycloalkyl in which one or more ring members are optionally replaced by heteroatoms, arylalkyl, aryl, hetarylalkyl or hetaryl or A and D together with the atoms to which they are attached represent a saturated or unsaturated ring which is unsubstituted or substituted in the A,D moiety G represents hydrogen.

2. A compound of the formula (I) according to claim 1 in which

X represents halogen, $C_1$–$C_6$-alkyl, $C_1$–$C_6$-halogenoalkyl, $C_1$–$C_6$-alkoxy, $C_3$–$C_6$-alkenyloxy, $C_1$–$C_6$-alkylthio, $C_1$–$C_6$-alkylsulphinyl, $C_1$–$C_6$-alkylsulphonyl, $C_1$–$C_6$-halogenoalkoxy, $C_3$–$C_6$-halogenoalkenyloxy, nitro, cyano or in each case optionally halogen-, $C_1$–$C_6$-alkyl-, $C_1$–$C_6$-alkoxy-, $C_1$–$C_4$-halogenoalkyl-, $C_1$–$C_4$-halogenoalkoxy-, nitro- or cyano-substituted phenyl, phenoxy, phenylthio, benzyloxy or benzylthio, Z represents one of the radicals

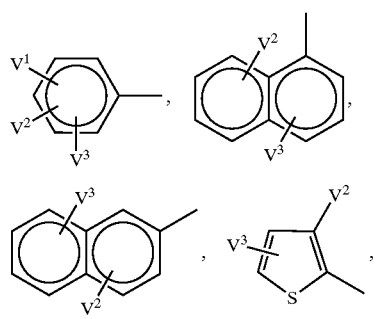

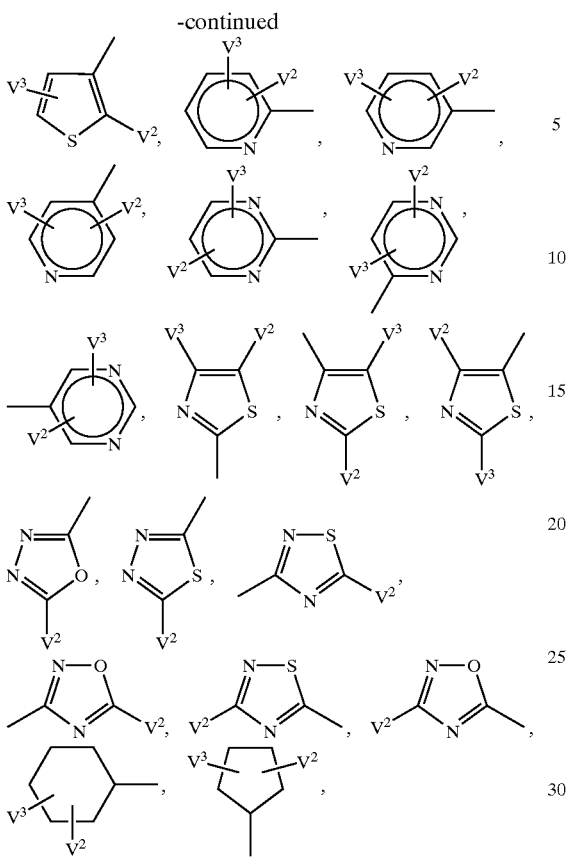

wherein

V[1] represents hydrogen, halogen, $C_1-C_{12}$-alkyl, $C_1-C_6$-alkoxy, $C_1-C_6$-alkylthio, $C_1-C_6$-alkylsulphinyl, $C_1-C_6$-alkylsulphonyl, $C_1-C_4$-halogenoalkyl, $C_1-C_4$-halogenoalkoxy, nitro, cyano or phenyl, phenoxy, phenoxy-$C_1-C_4$-alkyl, phenyl-$C_1-C_4$-alkoxy, phenylthio-$C_1-C_4$-alkyl or phenyl-$C_1-C_4$-alkylthio, each of which is optionally mono- or poly-substituted by halogen, $C_1-C_6$-alkyl, $C_1-C_6$-alkoxy, $C_1-C_4$-halogenoalkyl, $C_1-C_4$halogenoalkoxy, nitro or cyano, V[2] and V[3] independently of one another each represent hydrogen, halogen, $C_1-C_6$-alkyl, $C_1-C_6$-alkoxy, $C_1-C_4$-halogenoalkyl or $C_1-C_4$-halogeno-alkoxy, W and Y independently of one another each represent hydrogen, halogen, $C_1-C_6$-alkyl, $C_1-C_6$-halogenoalkyl, $C_1-C_6$-alkoxy, $C_1-C_6$-halogenoalkoxy, nitro or cyano, CKE represents

(1)

wherein

A represents hydrogen or in each case optionally halogen-substituted $C_1-C_{12}$-alkyl, $C_3-C_8$-alkenyl, $C_1-C_{10}$-alkoxy-$C_1-C_8$-alkyl, poly-$C_1-C_8$-alkoxy-$C_1-C_8$-alkyl, $C_1-C_{10}$-alkylthio-$C_1-C_6$-alkyl, optionally halogen-, $C_1-C_6$-alkyl- or $C_1-C_6$-alkoxy-substituted $C_3-C_8$-cycloalkyl in which optionally one or two not directly adjacent ring members are replaced by oxygen and/or sulphur or represents in each case optionally halogen-, $C_1-C_6$-alkyl-, $C_1-C_6$-halogenoalkyl-, $C_1-C_6$-alkoxy-, $C_1-C_6$-halogenoalkoxy-, cyano- or nitro-substituted $C_6$- or $C_{10}$-aryl, hetaryl having 5 or 6 ring atoms or $C_6$- or $C_{10}$-aryl-$C_1-C_6$-alkyl, B represents hydrogen, $C_1-C_{12}$-alkyl or $C_1-C_8$-alkoxy-$C_1-C_6$-alkyl or A, B and the carbon atom to which they are attached represent saturated $C_3-C_{10}$-cycloalkyl or unsaturated $C_5-C_{10}$-cycloalkyl in which optionally one ring member is replaced by oxygen or sulphur and which are optionally mono- or disubstituted by $C_1-C_8$-alkyl, $C_3-C_{10}$-cycloalkyl, $C_1-C_8$-halogenoalkyl, $C_1-C_8$-alkoxy, $C_1-C_8$-alkylthio, halogen or phenyl or A, B and the carbon atom to which they are attached represent $C_3-C_6$-cycloalkyl which is substituted by an alkylenediyl group which optionally contains one or two not directly adjacent oxygen and/or sulphur atoms, or by an alkylenedioxyl group or by an alkylenedithioyl group which, together with the carbon atom to which it is attached, forms a further five- to eight-membered ring, or A, B and the carbon atom to which they are attached represent $C_3-C_8$-cycloalkyl or $C_5-C_8$-cycloalkenyl, in which two substituents together with the carbon atoms to which they are attached represent in each case optionally $C_1-C_6$-alkyl-, $C_1-C_6$-alkoxy- or halogen-substituted $C_2-C_6$-alkanediyl, $C_2-C_6$-alkenediyl or $C_4-C_6$-alkanedienediyl in which optionally one methylene group is replaced by oxygen or sulphur, D represents hydrogen, in each case optionally halogen-substituted $C_1-C_{12}$-alkyl, $C_3-C_8$-alkenyl, $C_3-C_8$-alkinyl, $C_1-C_{10}$-alkoxy-$C_2-C_8$-alkyl, poly-$C_1-C_8$-alkoxy-$C_2-C_8$-alkyl, $C_1-C_{10}$-alkylthio-$C_2-C_8$-alkyl, optionally halogen-, $C_1-C_4$-alkyl-, $C_1-C_4$-alkoxy- or $C_1-C_4$-halogenoalkyl-substituted $C_3-C_8$-cycloalkyl in which optionally one ring member is replaced by oxygen or sulphur or in each case optionally halogen-, $C_1-C_6$-alkyl-, $C_1-C_6$-halogenoalkyl-, $C_1-C_6$-alkoxy-, $C_1-C_6$-halogenoalkoxy-, cyano- or nitro-substituted phenyl, hetaryl having 5 or 6 ring atoms, phenyl-$C_1-C_6$-alkyl or hetaryl-$C_1-C_6$-alkyl having 5 or 6 ring atoms, or A and D together represent in each case optionally substituted $C_3-C_6$-alkane-diyl or $C_3-C_6$-alkenediyl in which optionally one methylene group is replaced by oxygen or sulphur, possible substituents in each case being:

halogen, hydroxyl, mercapto or in each case optionally halogen-substituted $C_1-C_{10}$-alkyl, $C_1-C_6$-alkoxy, $C_1-C_6$-alkylthio, $C_3-C_7$-cycloalkyl, phenyl or benzyloxy, or a further $C_3-C_6$-alkanediyl group, $C_3-C_6$-alkenediyl group or a butadienyl group which is optionally substituted by $C_1-C_6$-alkyl or in which optionally two adjacent substituents together with the carbon atoms to which they are attached form a further saturated or unsaturated ring having 5 or 6 ring atoms (in the case of the compound of the formula (I-1), A and D, together with the atoms to which they are attached, then represent, for example, the groups AD-1 to AD-10 mentioned further below) which ring may contain oxygen or sulphur, or which may optionally contain one of the groups below

131

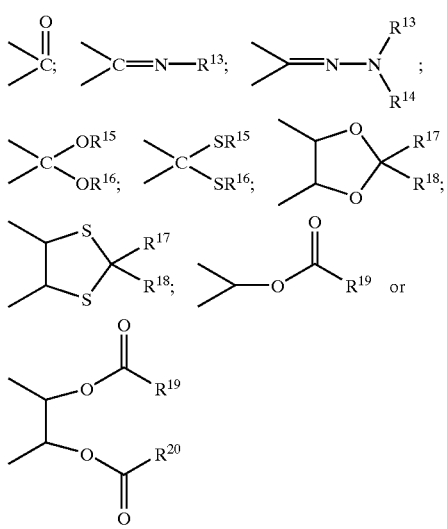

G represents hydrogen,

R$^{13}$ represents hydrogen, represents in each case optionally halogen-substituted C$_1$–C$_8$-alkyl or C$_1$–C$_8$-alkoxy, represents optionally halogen-, C$_1$–C$_4$-alkyl- or C$_1$–C$_4$-alkoxy-substituted C$_3$–C$_8$-cycloalkyl in which optionally one methylene group is replaced by oxygen or sulphur, or represents in each case optionally halogen-, C$_1$–C$_6$-alkyl-, C$_1$–C$_6$-alkoxy-, C$_1$–C$_4$-halogenoalkyl-, C$_1$–C$_4$-halogenoalkoxy-, nitro- or cyano-substituted phenyl, phenyl-C$_1$–C$_4$-alkyl or phenyl-C$_1$–C$_4$-alkoxy, R$^{14}$ represents hydrogen or C$_1$–C$_8$-alkyl, or R$^{13}$ and R$^{14}$ together represent C$_4$–C$_6$-alkanediyl, R$^{15}$ and R$^{16}$ are identical or different and each represent C$_1$–C$_6$-alkyl, or R$^{15}$ and R$^{16}$ together represent a C$_2$–C$_4$-alkanediyl radical which is optionally substituted by C$_1$–C$_6$-alkyl, C$_1$–C$_6$-halogenoalkyl or by optionally halogen-, C$_1$–C$_6$-alkyl-, C$_1$–C$_4$-halogenoalkyl-, C$_1$–C$_6$-alkoxy-, C$_1$–C$_4$-halogenoalkoxy-, nitro- or cyano-substituted phenyl, R$^{17}$ and R$^{18}$ independently of one another each represent hydrogen, represent optionally halogen-substituted C$_1$–C$_8$-alkyl or represent optionally halogen-, C$_1$–C$_6$-alkyl-, C$_1$–C$_6$-alkoxy-, C$_1$–C$_4$-halogeno-alkyl-, C$_1$–C$_4$-halogenoalkoxy-, nitro- or cyano-substituted phenyl, or R$^{17}$ and R$^{18}$ together with the carbon atom to which they are attached represent a carbonyl group or represent optionally halogen-, C$_1$–C$_4$-alkyl- or C$_1$–C$_4$-alkoxy-substituted C$_5$–C$_7$-cycloalkyl in which optionally one methylene group is replaced by oxygen or sulphur and R$^{19}$ and R$^{20}$ independently of one another each represent C$_1$–C$_{10}$-alkyl, C$_2$–C$_{10}$-alkenyl, C$_1$–C$_{10}$-alkoxy, C$_1$–C$_{10}$-alkylamino, C$_3$–C$_{10}$-alkenylamino, di-(C$_1$–C$_{10}$-alkyl)amino or di-(C$_3$–C$_{10}$-alkenyl)amino.

3. A compound of the formula (I) according to claim 1 in which

X represents fluorine, chlorine, bromine, C$_1$–C$_4$-alkyl, C$_1$–C$_4$-alkoxy, C$_3$–C$_4$-alkenyloxy, C$_1$–C$_4$-halogenoalkyl, C$_1$–C$_4$-halogenoalkoxy, C$_3$–C$_4$-halogenoalkenyloxy, nitro or cyano,

132

Z represents one of the radicals

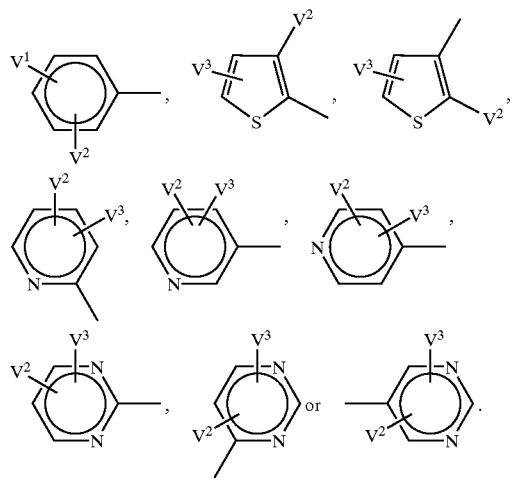

wherein

V$^1$ represents hydrogen, fluorine, chlorine, bromine, C$_1$–C$_6$-alkyl, C$_1$–C$_4$-alkoxy, C$_1$–C$_2$-halogenoalkyl, C$_1$–C$_2$-halogenoalkoxy, nitro, cyano or phenyl, phenoxy, phenoxy-C$_1$–C$_2$-alkyl, phenyl-C$_1$–C$_2$-alkoxy, phenylthio-C$_1$–C$_2$-alkyl or phenyl-C$_1$–C$_2$-alkylthio, each of which is optionally mono- or disubstituted by fluorine, chlorine, bromine, C$_1$–C$_4$-alkyl, C$_1$–C$_4$-alkoxy, C$_1$–C$_2$-halogenoalkyl, C$_1$–C$_2$-halogenoalkoxy, nitro or cyano, V$^2$ and V$^3$ independently of one another each represent hydrogen, fluorine, chlorine, bromine, C$_1$–C$_4$-alkyl, C$_1$–C$_4$-alkoxy, C$_1$–C$_2$-halogenoalkyl or C$_1$–C$_2$-halogenoalkoxy, W and Y independently of one another each represent hydrogen, fluorine, chlorine, bromine, C$_1$–C$_4$-alkyl, C$_1$–C$_4$-halogenoalkyl, C$_1$–C$_4$-alkoxy or C$_1$–C$_4$-halogenoalkoxy, CKE represents

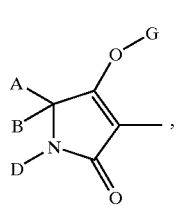

(1)

wherein

A represents hydrogen or represents in each case optionally fluorine- or chlorine-substituted C$_1$–C$_{10}$-alkyl, C$_1$–C$_8$-alkoxy-C$_1$–C$_6$-alkyl, optionally fluorine-, chlorine-, C$_1$–C$_4$-alkyl- or C$_1$–C$_4$-alkoxy-substituted C$_3$–C$_7$-cycloalkyl in which optionally one ring member is replaced by oxygen or sulphur or in each case optionally fluorine-, chlorine-, bromine-, C$_1$–C$_4$-alkyl-, C$_1$–C$_4$-halogenoalkyl-, C$_1$–C$_4$-alkoxy- or C$_1$–C$_4$-halogenoalkoxy-substituted phenyl, furanyl, pyridyl, imidazolyl, triazolyl, pyrazolyl, pyrimidyl, thiazolyl, thienyl or phenyl-C$_1$–C$_4$-alkyl, B represents hydrogen or C$_1$–C$_6$-alkyl, or A, B and the carbon atom to which they are attached represent saturated or unsaturated C$_5$–C$_7$-cycloalkyl in which optionally one ring member is replaced by oxygen or sulphur and which is optionally monosubstituted by $C_1$–$C_6$-alkyl, $C_5$–$C_8$-cycloalkyl, $C_1$–$C_3$-halogenoalkyl, $C_1$–$C_6$-alkoxy, fluorine, chlorine or phenyl, or A, B and the carbon atom to which they are attached represent $C_5$–$C_6$-cycloalkyl which is substituted by an alkylenediyl group which optionally contains one or two not directly adjacent oxygen or sulphur atoms or by an alkylenedioxyl group or by an alkylenedithiol group which, together with the carbon atom to which it is attached, forms a further five- or six-membered ring, or A, B and the carbon atom to which they are attached represent $C_3$–$C_6$-cycloalkyl or $C_5$–$C_6$-cycloalkenyl in which two substituents together with the carbon atoms to which they are attached represent in each case optionally $C_1$–$C_5$-alkyl-, $C_1$–$C_5$-alkoxy-, fluorine-, chlorine- or bromine-substituted $C_2$–$C_4$-alkanediyl or $C_2$–$C_4$-alkenediyl, in which optionally one methylene group is replaced by oxygen or sulphur, or represent butadienediyl, D represents hydrogen, represents in each case optionally fluorine- or chlorine-substituted $C_1$–$C_{10}$-alkyl, $C_3$–$C_6$-alkenyl, $C_1$–$C_8$-alkoxy-$C_2$–$C_6$-alkyl or $C_1$–$C_8$-alkylthio–$C_2$–$C_6$-alkyl, represents optionally fluorine-, chloro-, $C_1$–$C_4$-alkyl-, $C_1$–$C_4$-alkoxy- or $C_1$–$C_2$-halogeno-alkyl-substituted $C_3$–$C_7$-cycloalkyl in which optionally one methylene group is replaced by oxygen or sulphur or A and D together represent optionally substituted $C_3$–$C_5$-alkanediyl in which one methylene group may be replaced by a carbonyl group, oxygen or sulphur, possible substituents being hydroxyl, $C_1$–$C_6$-alkyl or $C_1$–$C_4$-alkoxy, or A and D (in the case of the compounds of the formula (I-1)) together with the atoms to which they are attached represent one of the groups AD-1 to AD-10:

AD-1

AD-2

AD-3

AD-4

AD-5

AD-6

AD-7

AD-8

AD-9

AD-10

G represents hydrogen.

4. A compound of the formula (I) according to claim 1 in which
X represents fluorine, chlorine, methyl, ethyl, propyl, iso-propyl, methoxy, ethoxy, propoxy, iso-propoxy, trifluoromethyl, difluoromethoxy, trifluoromethoxy, nitro or cyano,
Z represents one of the radicals wherein
$V^1$ represents hydrogen, fluorine, chlorine, bromine, methyl, ethyl, n-propyl, iso-propyl, n-butyl, iso-butyl, tert-butyl, methoxy, ethoxy, n-propoxy, iso-propoxy, trifluoromethyl, trifluoromethoxy, nitro, cyano or phenyl which is optionally monosubstituted by fluorine, chlorine, methyl, methoxy, trifluoromethyl or trifluoromethoxy, V² and V³ independently of one another each represent hydrogen, fluorine, chlorine, methyl, ethyl, n-propyl, iso-propyl, methoxy, ethoxy, trifluoromethyl or trifluoromethoxy, W and Y independently of one another each represent hydrogen, fluorine, chlorine, methyl, ethyl, n-propyl, methoxy, ethoxy or propoxy, CKE represents (1)

wherein

A represents hydrogen or represents in each case optionally fluorine-substituted $C_1$–$C_8$-alkyl or $C_1$–$C_6$-alkoxy–$C_1$–$C_4$-alkyl, optionally fluorine-, methyl-, ethyl- or methoxy-substituted $C_3$–$C_6$-cycloalkyl in which optionally one ring member is replaced by oxygen or sulphur or represents in each case optionally fluorine-, chlorine-, bromine-, methyl-, ethyl-, n-propyl-, iso-propyl-, methoxy-, ethoxy-, trifluoromethyl-, trifluoromethoxy-, cyano- or nitro-substituted phenyl or benzyl, B represents hydrogen or $C_1$–$C_4$-alkyl, or A, B and the carbon atom to which they are attached represent saturated $C_5$–$C_6$-cycloalkyl in which optionally one ring member is replaced by oxygen or sulphur and which is optionally monosubstituted by methyl, ethyl, propyl, isopropyl, butyl, iso-butyl, sec-butyl, tert-butyl, trifluoromethyl, methoxy, ethoxy, propoxy, iso-propoxy, butoxy, iso-butoxy, sec-butoxy, tert-butoxy, fluorine or chlorine, or A, B and the carbon atom to which they are attached represent $C_5$–$C_6$-cycloalkyl or $C_5$–$C_6$-cycloalkenyl in which two substituents together with the carbon atoms to which they are attached represent $C_2$–$C_4$-alkanediyl or $C_2$–$C_4$-alkenediyl in which in each case optionally one methylene group is replaced by oxygen or sulphur, or represent butadienediyl, D represents hydrogen, represents in each case optionally fluorine- or chlorine-substituted $C_1$–$C_8$-alkyl, $C_3$–$C_4$-alkenyl, $C_1$–$C_6$-alkoxy-$C_2$–$C_4$-alkyl, $C_1$–$C_4$-alkylthio-$C_2$–$C_4$-alkyl or $C_3$–$C_6$-cycloalkyl in which optionally one methylene group is replaced by oxygen or sulphur or A and D together represent optionally substituted $C_3$–$C_4$-alkanediyl in which optionally one carbon atom is replaced by sulphur and which is optionally substituted by hydroxyl, methyl, ethyl, methoxy or ethoxy, or A and D (in the case of the compounds of the formula (I-1)) together with the atoms to which they are attached represent one of the following groups AD:

AD-1

AD-2

AD-3

AD-4

AD-6

AD-8

AD-10

G represents hydrogen.

5. A process for preparing a compound of the formula (I) according to claim 1, particularly a compound of the formula (I-1-a)

(I-1-a)

in which

A, B, D, W, X, Y and Z are each as defined in claim 1 comprising the step of:

(A) intramolecularly condensing an N-acylamino acid ester of the formula (II)

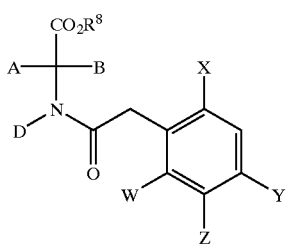

(II)

in which

A, B, D, W, X, Y and Z are each as defined above and R$^8$ represents alkyl in the presence of a diluent and in the presence of a base.

6. A compound of the formula (II)

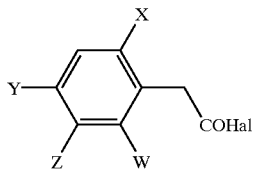

(II)

in which

A, B, D, W, X, Y and Z are each as defined in claim 1 and R$^8$ represents alkyl.

7. A compound of the formula (XXIV)

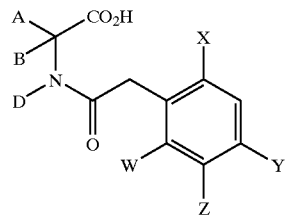

(XXIV)

in which

W, X, Y and Z are each as defined in claim 1 and Hal represents chlorine or bromine.

8. A compound of the formula (XXV)

(XXV)

in which

A, B, D, W, W, X, Y and Z are each as defined in claim 1.

9. A compound of the formula (XXIX)

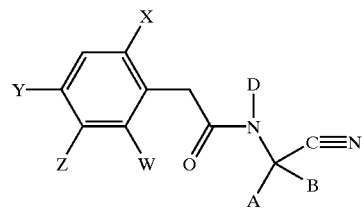

(XXIX)

in which

A, B, D, W, X, Y and Z are each as defined in claim 1.

10. A method for preparing pesticides and/or herbicides, comprising the step of mixing a compound of the formula (I) according to claim 1 with a member selected from the group consisting of an extender, a surfactant and combinations thereof.

11. Pesticides and/or herbicides, comprising at least one compound of the formula (I) according to claim 1.

12. A method for controlling pests comprising the step of allowing an effective amount of a compound of the formula (I) according to claim 1 to act on a member selected from the group consisting of said pests, a habitat of said pests and combinations thereof.

* * * * *